(12) United States Patent
Chinnaiyan et al.

(10) Patent No.: US 11,697,852 B2
(45) Date of Patent: Jul. 11, 2023

(54) SYSTEMS AND METHODS FOR DETERMINING A TREATMENT COURSE OF ACTION

(71) Applicant: The Regents of the University of Michigan, Ann Arbor, MI (US)

(72) Inventors: Arul M. Chinnaiyan, Plymouth, MI (US); Dan Robinson, Ann Arbor, MI (US); Yi-Mi Wu, Ann Arbor, MI (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 16/241,565

(22) Filed: Jan. 7, 2019

(65) Prior Publication Data
US 2019/0271045 A1 Sep. 5, 2019

Related U.S. Application Data

(62) Division of application No. 14/513,501, filed on Oct. 14, 2014, now Pat. No. 10,174,381.

(60) Provisional application No. 61/992,615, filed on May 13, 2014, provisional application No. 61/892,743, filed on Oct. 18, 2013.

(51) Int. Cl.
| | |
|---|---|
| *C12Q 1/68* | (2018.01) |
| *C12P 19/34* | (2006.01) |
| *C12Q 1/6886* | (2018.01) |
| *G01N 33/574* | (2006.01) |
| *C07K 14/705* | (2006.01) |
| *C07K 14/72* | (2006.01) |

(52) U.S. Cl.
CPC ...... *C12Q 1/6886* (2013.01); *C07K 14/70567* (2013.01); *C07K 14/721* (2013.01); *G01N 33/57415* (2013.01); *G01N 33/57442* (2013.01); *C12Q 2600/106* (2013.01); *C12Q 2600/156* (2013.01); *G01N 2333/723* (2013.01)

(58) Field of Classification Search
CPC ............ C12Q 1/6886; C12Q 2600/106; C12Q 2600/156
See application file for complete search history.

(56) References Cited

U.S. PATENT DOCUMENTS

| | | | |
|---|---|---|---|
| 10,174,381 B2 | 1/2019 | Chinnaiyan et al. | |
| 2001/0053519 A1 | 12/2001 | Fodor et al. | |
| 2003/0152959 A1 | 8/2003 | Mertz et al. | |
| 2015/0258099 A1* | 9/2015 | Hager ................ | A61K 31/4025 514/210.19 |

FOREIGN PATENT DOCUMENTS

| | | |
|---|---|---|
| WO | WO 03018746 A2 | 3/2003 |
| WO | WO 2004030621 A2 | 4/2004 |
| WO | WO 2013037972 A1 | 3/2013 |
| WO | WO 2013051678 A2 | 4/2013 |
| WO | WO 2013056178 A2 | 4/2013 |

OTHER PUBLICATIONS

Herynk, M.H. et al., "Estrogen Receptor Mutations in Human Disease" Endocrine Reviews 25(6):869-898. (Year: 2004).*
Kohler, M.F. et al., "Mutational Analysis of the Estrogen Receptor Gene in Endometrial Carcinoma" Obstet. Gynecol. vol. 86, No. 1, pp. 33-37. Jul. 1995. (Year: 1995).*
Angus et al., "ESR1 mutations: Moving towards guiding treatment decision-making in metastatic breast cancer patients." Cancer Treat Rev. Jan. 2017;52:33-40.
Ariazi et al., "Estrogen receptors as therapeutic targets in breast cancer." Curr Top Med Chem. 2006; 6(3):181-202.
Barone et al., "Estrogen receptor mutations and changes in downstream gene expression and signaling." Clin Cancer Res. May 15, 2010; 16(10):2702-8.
Bastarrachea et al., "Obesity as an adverse prognostic factor for patients receiving adjuvant chemotherapy for breast cancer." Ann Intern Med. Jan. 1, 1994; 120(1):18-25.
Billard et al., "The allele-specific probe and primer amplification assay, a new real-time PCR method for fine quantification of single-nucleotide polymorphisms in pooled DNA." Appl Environ Microbiol. Feb. 2012;78(4):1063-8.
Carlson et al., "Altered ligand binding properties and enhanced stability of a constitutively active estrogen receptor: evidence that an open pocket conformation is required for ligand interaction." Biochemistry. Dec. 2, 1997;36(48):14897-905.
Dawson et al., "Analysis of circulating tumor DNA to monitor metastatic breast cancer." N Engl J Med. Mar. 28, 2013;368(13):1199-209.
Diehl et al., "Circulating mutant DNA to assess tumor dynamics." Nat Med. Sep. 2008; 14(9):985-90.
Edwards et al. "Infiltrating ductal carcinoma of the breast: the survival impact of race." J Clin Oncol. Aug. 1998, 16(8):2693-9.
Elledge et al., "Tumor biologic factors and breast cancer prognosis among white, Hispanic, and black women in the United States." J Natl Cancer Inst. May 1994;86(9):705-12.
Ellis et al., "Lower-dose vs high-dose oral estradiol therapy of hormone receptor-positive, aromatase inhibitor-resistant advanced breast cancer: a phase 2 randomized study." JAMA. Aug. 19, 2009; 302(7):774-80.
Ellis et al., "Whole-genome analysis informs breast cancer response to aromatase inhibition." Nature. Jun. 10, 2012; 486(7403):353-60.
Feil et al., "Regulation of Cre recombinase activity by mutated estrogen receptor ligand-binding domains." Biochem Biophys Res Commun. Aug. 28, 1997; 237(3):752-7.
GenBank Locus: HUMERMCF (Nov. 8, 1994), "Human estrogen receptor mRNA, complete cds.", printed pp. 1-3.

(Continued)

*Primary Examiner* — Stephen T Kapushoc
(74) *Attorney, Agent, or Firm* — Casimir Jones, S.C.; Tanya A. Arenson

(57) ABSTRACT

The present disclosure relates to methods of determining a treatment course of action. In particular, the present disclosure relates to mutations in the gene encoding estrogen receptor and their association with responsiveness to estrogen therapies for cancer.

7 Claims, 11 Drawing Sheets

Specification includes a Sequence Listing.

(56) References Cited

OTHER PUBLICATIONS

Gorre et al., "Clinical resistance to STI-571 cancer therapy caused by BCR-ABL gene mutation or amplification." Science. Aug. 3, 2001; 293(5531):876-80.
Herynk & Fuqua, "Estrogen receptor mutations in human disease." Endocr Rev. Dec. 2004; 25(6):869-98.
Huang et al., "Identification of a negative regulatory surface within estrogen receptor alpha provides evidence in support of a role for corepressors in regulating cellular responses to agonists and antagonists." Mol Endocrinol. Aug. 2002; 16(8):1778-92.
Ingle et al., "Fulvestrant in women with advanced breast cancer after progression on prior aromatase inhibitor therapy: North Central Cancer Treatment Group Trial N0032." J Clin Oncol. Mar. 1, 2006; 24(7):1052-6.
Joseph et al., "A clinically relevant androgen receptor mutation confers resistance to second-generation antiandrogens enzalutamide and ARN-509." Cancer Discov. Sep. 2013; 3(9):1020-9.
Kan et al., "Diverse somatic mutation patterns and pathway alterations in human cancers." Nature. Aug. 12, 2010; 466(7308):869-73.
Kandoth et al., "Integrated genomic characterization of endometrial carcinoma." Nature. May 2, 2013; 497(7447):67-73.
Koboldt et al., "Comprehensive molecular portraits of human breast tumours." Nature. Oct. 4, 2012;490(7418):61-70.
Korpal et al., "An F876L mutation in androgen receptor confers genetic and phenotypic resistance to MDV3100 (enzalutamide)." Cancer Discov. Sep. 2013; 3(9):1030-43.
Lønning & Eikesdal, "Aromatase inhibition 2013: clinical state of the art and questions that remain to be solved." Endocr Relat Cancer. Jun. 24, 2013; 20(4):R183-201.
Nik-Zainal et al., "Mutational processes molding the genomes of 21 breast cancers." Cell. May 25, 2012; 149(5):979-93.
Osborne & Schiff, "Mechanisms of endocrine resistance in breast cancer." Annu Rev Med. 2011; 62:233-47.
Pearce et al., "Modulation of estrogen receptor alpha function and stability by tamoxifen and a critical amino acid (Asp-538) in helix 12." J Biol Chem. Feb. 28, 2003;278(9):7630-8.
Riggins et al., "Pathways to tamoxifen resistance." Cancer Lett. Oct. 18, 2007; 256(1):1-24.
Robinson et al., "Activating ESR1 mutations in hormone-resistant metastatic breast cancer." Nat Genet. Dec. 2013;45(12):1446-51.
Roychowdhury et al., "Personalized oncology through integrative high-throughput sequencing: a pilot study." Sci Transl Med. Nov. 30, 2011; 3(111):111ra121.
Shiau et al., "The structural basis of estrogen receptor/coactivator recognition and the antagonism of this interaction by tamoxifen." Cell. Dec. 23, 1998; 95(7):927-37.
Shrestha et al., "PAK1 is a breast cancer oncogene that coordinately activates MAPK and MET signaling." Oncogene. Jul. 19, 2012; 31(29):3397-408.
Skafar et al., "Formation of a powerful capping motif corresponding to start of "helix 12" in agonist-bound estrogen receptor-alpha contributes to increased constitutive activity of the protein." Cell Biochem Biophys. 2000; 33(1):53-62.
Swaby & Jordan, "Low-dose estrogen therapy to reverse acquired antihormonal resistance in the treatment of breast cancer." Clin Breast Cancer. Apr. 2008; 8(2):124-33.
Tapp et al., "Homogeneous scoring of single-nucleotide polymorphisms: comparison of the 5'-nuclease TaqMan assay and Molecular Beacon probes." Biotechniques. Apr. 2000;28(4):732-8.
Weis et al., "Constitutively active human estrogen receptors containing amino acid substitutions for tyrosine 537 in the receptor protein." Mol Endocrinol. Nov. 1996; 10(11):1388-98.
Welch et al., "Use of whole-genome sequencing to diagnose a cryptic fusion oncogene." JAMA. Apr. 20, 2011; 305(15):1577-84.
Wu et al., "Identification of targetable FGFR gene fusions in diverse cancers." Cancer Discov. Jun. 2013; 3(6):636-47.
Zhang et al., "An estrogen receptor mutant with strong hormone-independent activity from a metastatic breast cancer." Cancer Res. Apr. 1, 1997;57(7):1244-9.
Zhao et al., "Mutation of Leu-536 in human estrogen receptor-alpha alters the coupling between ligand binding, transcription activation, and receptor conformation." J Biol Chem. Jul. 18, 2003;278(29):27278-86.
Zhong et al., "Mutations of Tyrosine 537 in the Human Estrogen Receptor—a Selectively Alter the Receptor's Affinity for Estradiol and the Kinetics of the Interaction" Biochemistry 2002, 41, 4209-4217.
Search Report, related European Application No. 14854474.5, dated Apr. 28, 2017, 14 pages.
Office Action for CA App. No. 2927752, dated Dec. 14, 2022, 5 pages.

* cited by examiner

SEQUENCE LISTING

```
<160> NUMBER OF SEQ ID NOS: 7

<210> SEQ ID NO 1
<211> LENGTH: 51
<212> TYPE: PRT
<213> ORGANISM: Homo sapien

<400> SEQUENCE: 1

Ser Met Glu His Pro Gly Lys Leu Leu Phe Ala Leu Ser His Ile Arg
1               5                   10                  15

His Met Ser Asn Lys Gly Met Glu His Leu Tyr Ser Met Lys Cys Lys
            20                  25                  30

Asn Val Val Pro Leu Tyr Asp Leu Leu Leu Glu Met Leu Asp Ala His
        35                  40                  45

Arg Leu His
    50

<210> SEQ ID NO 2
<211> LENGTH: 51
<212> TYPE: PRT
<213> ORGANISM: Homo sapien

<400> SEQUENCE: 2

Ser Met Glu His Pro Gly Lys Leu Leu Phe Ala Leu Ser His Ile Arg
1               5                   10                  15

His Met Ser Asn Lys Gly Met Glu His Leu Tyr Ser Met Lys Cys Lys
```

```
                20                  25                  30

Asn Val Val Pro Gln Tyr Asp Leu Leu Glu Met Leu Asp Ala His
            35                  40                  45

Arg Leu His
    50

<210> SEQ ID NO 3
<211> LENGTH: 51
<212> TYPE: PRT
<213> ORGANISM: Homo sapien

<400> SEQUENCE: 3

Ser Met Glu His Pro Gly Lys Leu Leu Phe Ala Leu Ser His Ile Arg
1               5                   10                  15

His Met Ser Asn Lys Gly Met Glu His Leu Tyr Ser Met Lys Cys Lys
            20                  25                  30

Asn Val Val Pro Leu Ser Asp Leu Leu Glu Met Leu Asp Ala His
            35                  40                  45

Arg Leu His
    50

<210> SEQ ID NO 4
<211> LENGTH: 51
<212> TYPE: PRT
<213> ORGANISM: Homo sapien

<400> SEQUENCE: 4

Ser Met Glu His Pro Gly Lys Leu Leu Phe Ala Leu Ser His Ile Arg
1               5                   10                  15

His Met Ser Asn Lys Gly Met Glu His Leu Tyr Ser Met Lys Cys Lys
            20                  25                  30

Asn Val Val Pro Leu Tyr Gly Leu Leu Glu Met Leu Asp Ala His
            35                  40                  45

Arg Leu His
    50

<210> SEQ ID NO 5
<211> LENGTH: 51
<212> TYPE: PRT
<213> ORGANISM: Homo sapien

<400> SEQUENCE: 5

Ser Met Glu His Pro Gly Lys Leu Leu Phe Ala Leu Ser His Ile Arg
1               5                   10                  15

His Met Ser Asn Lys Gly Met Glu His Leu Tyr Ser Met Lys Cys Lys
            20                  25                  30

Asn Val Val Pro Leu Cys Asp Leu Leu Glu Met Leu Asp Ala His
            35                  40                  45

Arg Leu His
    50

<210> SEQ ID NO 6
<211> LENGTH: 51
<212> TYPE: PRT
<213> ORGANISM: Homo sapien

<400> SEQUENCE: 6

Ser Met Glu His Pro Gly Lys Leu Leu Phe Ala Leu Ser His Ile Arg
1               5                   10                  15
```

```
His Met Ser Asn Lys Gly Met Glu His Leu Tyr Ser Met Lys Cys Lys
            20                  25                  30

Asn Val Val Pro Leu Asn Asp Leu Leu Leu Glu Met Leu Asp Ala His
            35                  40                  45

Arg Leu His
    50

<210> SEQ ID NO 7
<211> LENGTH: 51
<212> TYPE: PRT
<213> ORGANISM: Homo sapien

<400> SEQUENCE: 7

Ser Met Glu His Pro Val Lys Leu Leu Phe Ala Leu Ser His Ile Arg
1               5                   10                  15

His Met Ser Asn Lys Gly Met Glu His Leu Tyr Ser Met Lys Cys Lys
            20                  25                  30

Asn Val Val Pro Leu Tyr Asp Leu Leu Leu Glu Ala Ala Asp Ala His
            35                  40                  45

Arg Leu His
    50
```

SYSTEMS AND METHODS FOR DETERMINING A TREATMENT COURSE OF ACTION

CROSS REFERENCE TO RELATED APPLICATIONS

The present application is a divisional of U.S. patent application Ser. No. 14/513,501, filed Oct. 14, 2014, which claims priority to U.S. Provisional Patent Application Ser. No. 61/892,743, filed Oct. 18, 2013, and U.S. Provisional Patent Application Ser. No. 61/992,615, filed May 13, 2014, the disclosures of which are herein incorporated by reference in their entirety.

STATEMENT REGARDING FEDERALLY SPONSORED RESEARCH OR DEVELOPMENT

This invention was made with government support under CA111275 and HG006508 awarded by the National Institutes of Health. The Government has certain rights in the invention.

FIELD OF THE INVENTION

The present disclosure relates to methods of determining a treatment course of action. In particular, the present disclosure relates to mutations in the gene encoding estrogen receptor and their association with responsiveness to estrogen therapies for cancer.

BACKGROUND OF THE INVENTION

Breast cancer is the second most common form of cancer among women in the U.S., and the second leading cause of cancer deaths among women. While the 1980s saw a sharp rise in the number of new cases of breast cancer, that number now appears to have stabilized. The drop in the death rate from breast cancer is probably due to the fact that more women are having mammograms. When detected early, the chances for successful treatment of breast cancer are much improved.

Breast cancer, which is highly treatable by surgery, radiation therapy, chemotherapy, and hormonal therapy, is most often curable when detected in early stages. Mammography is the most important screening modality for the early detection of breast cancer. Breast cancer is classified into a variety of sub-types, but only a few of these affect prognosis or selection of therapy. Patient management following initial suspicion of breast cancer generally includes confirmation of the diagnosis, evaluation of stage of disease, and selection of therapy. Diagnosis may be confirmed by aspiration cytology, core needle biopsy with a stereotactic or ultrasound technique for nonpalpable lesions, or incisional or excisional biopsy. At the time the tumor tissue is surgically removed, part of it is processed for determination of ER and PR levels.

Prognosis and selection of therapy are influenced by the age of the patient, stage of the disease, pathologic characteristics of the primary tumor including the presence of tumor necrosis, estrogen-receptor (ER) and progesterone-receptor (PR) levels in the tumor tissue, HER2 overexpression status and measures of proliferative capacity, as well as by menopausal status and general health. Overweight patients may have a poorer prognosis (Bastarrachea et al., Annals of Internal Medicine, 120: 18 [1994]). Prognosis may also vary by race, with blacks, and to a lesser extent Hispanics, having a poorer prognosis than whites (Elledge et al., Journal of the National Cancer Institute 86: 705 [1994]; Edwards et al., Journal of Clinical Oncology 16: 2693 [1998]). The three major treatments for breast cancer are surgery, radiation, and drug therapy. No treatment fits every patient, and often two or more are required. The choice is determined by many factors, including the age of the patient and her menopausal status, the type of cancer (e.g., ductal vs. lobular), its stage, whether the tumor is hormone-receptive or not, and its level of invasiveness.

Breast cancer treatments are defined as local or systemic. Surgery and radiation are considered local therapies because they directly treat the tumor, breast, lymph nodes, or other specific regions. Drug treatment is called systemic therapy, because its effects are wide spread. Drug therapies include classic chemotherapy drugs, hormone blocking treatment (e.g., aromatase inhibitors, selective estrogen receptor modulators, and estrogen receptor downregulators), and monoclonal antibody treatment (e.g., against HER2). They may be used separately or, most often, in different combinations.

There is a need for additional diagnostic and treatment options, particularly treatments customized to a patient's tumor.

SUMMARY OF THE INVENTION

The present disclosure relates to methods of determining a treatment course of action. In particular, the present disclosure relates to mutations in the gene encoding estrogen receptor and their association with responsiveness to estrogen therapies for cancer.

In some embodiments, the present disclosure provides a method of treating cancer, comprising: assaying a sample from a subject diagnosed with cancer for the presence of a mutation in the estrogen receptor (ESR1) gene (e.g. one or more of p.Leu536Gln, p.Tyr537Ser, p.Tyr537Cys, or p.Tyr537Asn); and determining a treatment course of action based on the presence of the mutation. In some embodiments, the method further comprises the step of administering the treatment when the mutation is present. In some embodiments, the treatment is an estrogen receptor antagonist (e.g., tamoxifen or fulvestrant). In some embodiments, the sample is, for example, tissue, blood, plasma, serum, endometrial cells, or breast cells. In some embodiments, the cancer is breast cancer or endometrial cancer. In some embodiments, the detecting comprises forming a complex between the ESR1 gene and a nucleic acid primer, probe, or pair of primers that specifically bind to the ESR1 gene. In some embodiments, the nucleic acid primer, probe, or pair of primers bind to the mutation in said ESR1 gene but not the wild type gene. In some embodiments, the ESR1 gene is assayed from circulating tumor nucleic acid. In some embodiments, the detecting comprising forming a complex between the mutant ESR1 polypeptide and an antibody that specifically binds to the variant amino acid sequence.

Further embodiments provide a method of monitoring treatment of cancer, comprising: administering a cancer therapy to a subject; assaying a sample from a subject diagnosed with cancer for the presence of a mutation in the estrogen receptor (ESR1) gene (e.g., p.Leu536Gln, p.Tyr537Ser, p.Tyr537Cys, or p.Tyr537Asn); and determining a treatment course of action based on the presence of the mutation. In some embodiments, the method further comprises the step of administering the treatment when the mutations are present. In some embodiments, the cancer therapy is an aromatase inhibitor.

Additional embodiments provide a complex comprising a nucleic acid encoding estrogen receptor (ESR1) gene comprising a mutation selected from, for example, p.Leu536Gln, p.Tyr537Ser, p.Tyr537Cys, or p.Tyr537Asn and a nucleic acid primer or probe that specifically hybridizes to a variant ESR1 nucleic acid endocing the mutant polypeptide but not the wild type nucleic acid. In some embodiments, a reaction mixture comprising a mutant ESR1 polypeptide and an antibody that specifically binds to the variant amino acid sequence is provided. In some embodiments, the present invention provides a multiplex (e.g., microarray) comprising reagents that binds to two or more variant ESR1 amino acid or nucleic acids.

In some embodiments, the present invention provides one or more nucleic acid probes or primers having 8 or more (e.g., 10 or more, 12 or more, 15 or more, 18 or more, etc.) nucleotides and that specifically bind to nucleic acids encoding a variant ESR polypeptide but not the wild type nucleic acid. In some embodiments, the present invention provides an antibody that specifically binds to variant ESR1 polypeptides but not wild type ESR1 polypeptides.

In some embodiments, the present invention provides a system comprising a computer processor and computer software configured to analyze information on the presence and absence of variant ESR1 polypeptides or amino acids encoding the polypeptides; and determine a treatment course of action based on the presence or absence of the variant gene or polypeptide.

Additional embodiments are described herein.

DEFINITIONS

Figure 1:
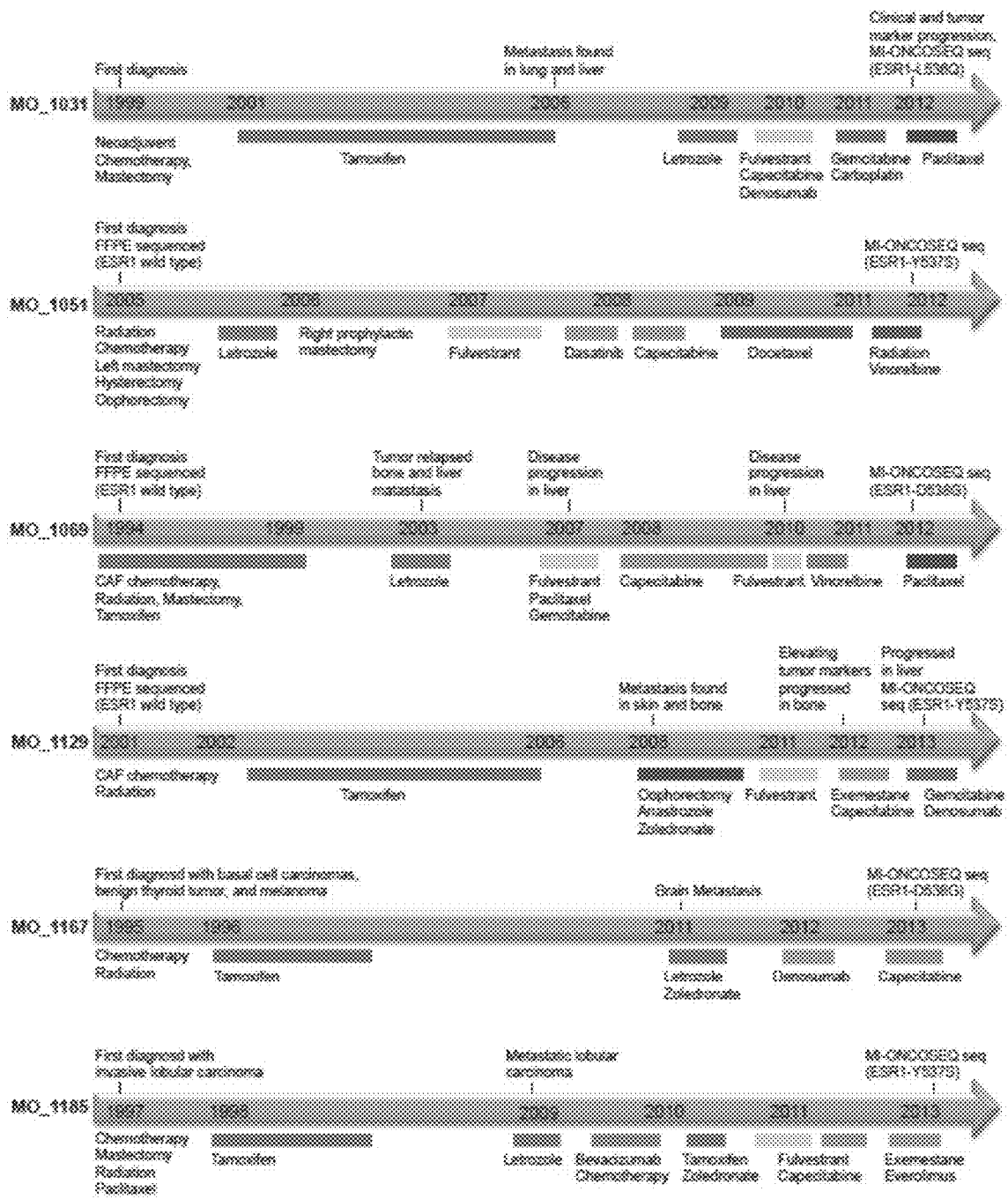
FIG. 1 shows clinical timelines of the six index ER-positive metastatic breast cancer patients harboring ESR1 mutations.

To facilitate an understanding of the present invention, a number of terms and phrases are defined below:

As used herein, the terms "detect", "detecting" or "detection" may describe either the general act of discovering or discerning or the specific observation of a detectably labeled composition.

As used herein, the term "subject" refers to any organisms that are screened using the diagnostic methods described herein. Such organisms preferably include, but are not limited to, mammals (e.g., humans).

The term "diagnosed," as used herein, refers to the recognition of a disease by its signs and symptoms, or genetic analysis, pathological analysis, histological analysis, and the like.

As used herein, the term "characterizing cancer in a subject" refers to the identification of one or more properties of a cancer sample in a subject, including but not limited to, the presence of benign, pre-cancerous or cancerous tissue, the stage of the cancer, and the subject's prognosis. Cancers may be characterized by the identification of the expression of one or more cancer marker genes, including but not limited to, the ESR1 variants disclosed herein.

As used herein, the term "characterizing cancer in a subject" refers to the identification of one or more properties of a cancer sample (e.g., including but not limited to, the presence of cancerous tissue, the presence or absence of ESR1 mutation, the presence of pre-cancerous tissue that is likely to become cancerous, and the presence of cancerous tissue that is likely to metastasize). In some embodiments, tissues are characterized by the identification of the expression of one or more cancer marker genes, including but not limited to, the cancer markers disclosed herein.

As used herein, the term "stage of cancer" refers to a qualitative or quantitative assessment of the level of advancement of a cancer. Criteria used to determine the stage of a cancer include, but are not limited to, the size of the tumor and the extent of metastases (e.g., localized or distant).

As used herein, the term "nucleic acid molecule" refers to any nucleic acid containing molecule, including but not limited to, DNA or RNA. The term encompasses sequences that include any of the known base analogs of DNA and RNA including, but not limited to, 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, N-uracil-5-oxyacetic acid methylester, uracil-5-oxyacetic acid, pseudouracil, queosine, 2-thiocytosine, and 2,6-diaminopurine.

The term "gene" refers to a nucleic acid (e.g., DNA) sequence that comprises coding sequences necessary for the production of a polypeptide, precursor, or RNA (e.g., rRNA, tRNA). The polypeptide can be encoded by a full length coding sequence or by any portion of the coding sequence so long as the desired activity or functional properties (e.g., enzymatic activity, ligand binding, signal transduction, immunogenicity, etc.) of the full-length or fragments are retained. The term also encompasses the coding region of a structural gene and the sequences located adjacent to the coding region on both the 5' and 3' ends for a distance of about 1 kb or more on either end such that the gene corresponds to the length of the full-length mRNA. Sequences located 5' of the coding region and present on the mRNA are referred to as 5' non-translated sequences. Sequences located 3' or downstream of the coding region and present on the mRNA are referred to as 3' non-translated sequences. The term "gene" encompasses both cDNA and genomic forms of a gene. A genomic form or clone of a gene contains the coding region interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

As used herein, the term "oligonucleotide," refers to a short length of single-stranded polynucleotide chain. Oligonucleotides are typically less than 200 residues long (e.g., between 15 and 100), however, as used herein, the term is also intended to encompass longer polynucleotide chains. Oligonucleotides are often referred to by their length. For example a 24 residue oligonucleotide is referred to as a "24-mer". Oligonucleotides can form secondary and tertiary structures by self-hybridizing or by hybridizing to other polynucleotides. Such structures can include, but are not limited to, duplexes, hairpins, cruciforms, bends, and triplexes.

As used herein, the terms "complementary" or "complementarity" are used in reference to polynucleotides (i.e., a sequence of nucleotides) related by the base-pairing rules. For example, the sequence "5'-A-G-T-3'," is complementary to the sequence "3'-T-C-A-5'." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The term "homology" refers to a degree of complementarity. There may be partial homology or complete homology (i.e., identity). A partially complementary sequence is a nucleic acid molecule that at least partially inhibits a completely complementary nucleic acid molecule from hybridizing to a target nucleic acid is "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a completely homologous nucleic acid molecule to a target under conditions of low stringency. This is not to say that conditions of low stringency are such that nonspecific binding is permitted; low stringency conditions require that the binding of two sequences to one another be a specific (i.e., selective) interaction. The absence of non-specific binding may be tested by the use of a second target that is substantially non-complementary (e.g., less than about 30% identity); in the absence of non-specific binding the probe will not hybridize to the second non-complementary target.

As used herein, the term "hybridization" is used in reference to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

As used herein the term "stringency" is used in reference to the conditions of temperature, ionic strength, and the presence of other compounds such as organic solvents, under which nucleic acid hybridizations are conducted. Under "low stringency conditions" a nucleic acid sequence of interest will hybridize to its exact complement, sequences with single base mismatches, closely related sequences (e.g., sequences with 90% or greater homology), and sequences having only partial homology (e.g., sequences with 50-90% homology). Under 'medium stringency conditions," a nucleic acid sequence of interest will hybridize only to its exact complement, sequences with single base mismatches, and closely relation sequences (e.g., 90% or greater homology). Under "high stringency conditions," a nucleic acid sequence of interest will hybridize only to its exact complement, and (depending on conditions such a temperature) sequences with single base mismatches. In other words, under conditions of high stringency the temperature can be raised so as to exclude hybridization to sequences with single base mismatches.

The term "isolated" when used in relation to a nucleic acid, as in "an isolated oligonucleotide" or "isolated polynucleotide" refers to a nucleic acid sequence that is identified and separated from at least one component or contaminant with which it is ordinarily associated in its natural source. Isolated nucleic acid is such present in a form or setting that is different from that in which it is found in nature. In contrast, non-isolated nucleic acids as nucleic acids such as DNA and RNA found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a given protein includes, by way of example, such nucleic acid in cells ordinarily expressing the given protein where the nucleic acid is in a chromosomal location different from that of natural cells, or is otherwise flanked by a different nucleic acid sequence than that found in nature. The isolated nucleic acid, oligonucleotide, or polynucleotide may be present in single-stranded or double-stranded form. When an isolated nucleic acid, oligonucleotide or polynucleotide is to be utilized to express a protein, the oligonucleotide or polynucleotide will contain at a minimum the sense or coding strand (i.e., the oligonucleotide or polynucleotide may be single-stranded), but may contain both the sense and anti-sense strands (i.e., the oligonucleotide or polynucleotide may be double-stranded).

As used herein, the term "purified" or "to purify" refers to the removal of components (e.g., contaminants) from a sample. For example, antibodies are purified by removal of contaminating non-immunoglobulin proteins; they are also purified by the removal of immunoglobulin that does not bind to the target molecule. The removal of non-immunoglobulin proteins and/or the removal of immunoglobulins that do not bind to the target molecule results in an increase in the percent of target-reactive immunoglobulins in the sample. In another example, recombinant polypeptides are expressed in bacterial host cells and the polypeptides are purified by the removal of host cell proteins; the percent of recombinant polypeptides is thereby increased in the sample.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues (e.g., biopsy samples), cells, and gases. Biological samples include blood products, such as plasma, serum and the like. Such examples are not however to be construed as limiting the sample types applicable to the present invention.

DETAILED DESCRIPTION OF THE INVENTION

The present disclosure relates to methods of determining a treatment course of action. In particular, the present disclosure relates to mutations in the gene encoding estrogen receptor and their association with responsiveness to estrogen therapies for cancer.

I. Diagnostic and Screening Methods

As described above, embodiments of the present invention provide diagnostic and screening methods that utilize the detection of mutations in ligand binding region of the estrogen receptor (ESR1) gene (e.g., p.Leu536Gln, p.Tyr537Ser, p.Tyr537Cys, p.Tyr537Asn, and p.Asp538Gly). Exemplary, non-limiting methods are described below.

Any patient sample suspected of containing the ESR1 gene may be tested according to methods of embodiments of the present invention. By way of non-limiting examples, the sample may be tissue (e.g., a breast, endometrial, ovarian, or uterine biopsy sample), blood, urine, or a fraction thereof (e.g., plasma, serum, cells).

In some embodiments, the patient sample is subjected to preliminary processing designed to isolate or enrich the sample for the ESR1 gens or cells that contain the gene. A variety of techniques known to those of ordinary skill in the art may be used for this purpose, including but not limited to: centrifugation; immunocapture; cell lysis; and, nucleic acid target capture (See, e.g., EP Pat. No. 1 409 727, herein incorporated by reference in its entirety).

In some embodiments, mutations in the ESR1 gene are monitored in circulating tumor DNA (See e.g., Dawson, S. J. et al. Analysis of circulating tumor DNA to monitor metastatic breast cancer. N Engl J Med 368, 1199-209 (2013); Diehl, F. et al. Nat Med 14, 985-90 (2008)).

In some embodiments, the ESR1 mutations are detected along with other markers in a multiplex or panel format. Markers are selected for their predictive value alone or in combination with the ESR1 mutations. Markers for other cancers, diseases, infections, and metabolic conditions are also contemplated for inclusion in a multiplex or panel format.

i. DNA and RNA Detection

The ESR1 mutation are detected using a variety of nucleic acid techniques known to those of ordinary skill in the art, including but not limited to: nucleic acid sequencing; nucleic acid hybridization; and, nucleic acid amplification.

1. Sequencing

A variety of nucleic acid sequencing methods are contemplated for use in the methods of the present disclosure including, for example, chain terminator (Sanger) sequencing, dye terminator sequencing, and high-throughput sequencing methods. Many of these sequencing methods are well known in the art. See, e.g., Sanger et al., Proc. Natl. Acad. Sci. USA 74:5463-5467 (1997); Maxam et al., Proc. Natl. Acad. Sci. USA 74:560-564 (1977); Drmanac, et al., Nat. Biotechnol. 16:54-58 (1998); Kato, Int. J. Clin. Exp. Med. 2:193-202 (2009); Ronaghi et al., Anal. Biochem. 242:84-89 (1996); Margulies et al., Nature 437:376-380 (2005); Ruparel et al., Proc. Natl. Acad. Sci. USA 102:5932-5937 (2005), and Harris et al., Science 320:106-109 (2008); Levene et al., Science 299:682-686 (2003); Korlach et al., Proc. Natl. Acad. Sci. USA 105:1176-1181 (2008); Branton et al., Nat. Biotechnol. 26(10):1146-53 (2008); Eid et al., Science 323:133-138 (2009); each of which is herein incorporated by reference in its entirety.

Next-generation sequencing (NGS) methods share the common feature of massively parallel, high-throughput strategies, with the goal of lower costs in comparison to older sequencing methods (see, e.g., Voelkerding et al., *Clinical Chem.*, 55: 641-658, 2009; MacLean et al., *Nature Rev. Microbiol.*, 7: 287-296; each herein incorporated by reference in their entirety). NGS methods can be broadly divided into those that typically use template amplification and those that do not. Amplification-requiring methods include pyrosequencing commercialized by Roche as the 454 technology platforms (e.g., GS 20 and GS FLX), the Solexa platform commercialized by Illumina, and the Supported Oligonucleotide Ligation and Detection (SOLiD) platform commercialized by Applied Biosystems. Non-amplification approaches, also known as single-molecule sequencing, are exemplified by the HeliScope platform commercialized by Helicos BioSciences, and emerging platforms commercialized by VisiGen, Oxford Nanopore Technologies Ltd., Life Technologies/Ion Torrent, and Pacific Biosciences, respectively.

In pyrosequencing (Voelkerding et al., *Clinical Chem.*, 55: 641-658, 2009; MacLean et al., *Nature Rev. Microbiol.*, 7: 287-296; U.S. Pat. Nos. 6,210,891; 6,258,568; each herein incorporated by reference in its entirety), template DNA is fragmented, end-repaired, ligated to adaptors, and clonally amplified in-situ by capturing single template molecules with beads bearing oligonucleotides complementary to the adaptors. Each bead bearing a single template type is compartmentalized into a water-in-oil microvesicle, and the template is clonally amplified using a technique referred to as emulsion PCR. The emulsion is disrupted after amplification and beads are deposited into individual wells of a picotitre plate functioning as a flow cell during the sequencing reactions. Ordered, iterative introduction of each of the four dNTP reagents occurs in the flow cell in the presence of sequencing enzymes and luminescent reporter such as luciferase. In the event that an appropriate dNTP is added to the 3' end of the sequencing primer, the resulting production of ATP causes a burst of luminescence within the well, which is recorded using a CCD camera. It is possible to achieve read lengths greater than or equal to 400 bases, and $10^6$ sequence reads can be achieved, resulting in up to 500 million base pairs (Mb) of sequence.

In the Solexa/Illumina platform (Voelkerding et al., *Clinical Chem.*, 55: 641-658, 2009; MacLean et al., *Nature Rev. Microbiol.*, 7: 287-296; U.S. Pat. Nos. 6,833,246; 7,115,400; 6,969,488; each herein incorporated by reference in its entirety), sequencing data are produced in the form of shorter-length reads. In this method, single-stranded fragmented DNA is end-repaired to generate 5'-phosphorylated blunt ends, followed by Klenow-mediated addition of a single A base to the 3' end of the fragments. A-addition facilitates addition of T-overhang adaptor oligonucleotides, which are subsequently used to capture the template-adaptor molecules on the surface of a flow cell that is studded with oligonucleotide anchors. The anchor is used as a PCR primer, but because of the length of the template and its proximity to other nearby anchor oligonucleotides, extension by PCR results in the "arching over" of the molecule to hybridize with an adjacent anchor oligonucleotide to form a bridge structure on the surface of the flow cell. These loops of DNA are denatured and cleaved. Forward strands are then sequenced with reversible dye terminators. The sequence of incorporated nucleotides is determined by detection of post-incorporation fluorescence, with each fluor and block removed prior to the next cycle of dNTP addition. Sequence read length ranges from 36 nucleotides to over 250 nucleotides, with overall output exceeding 1 billion nucleotide pairs per analytical run.

Sequencing nucleic acid molecules using SOLiD technology (Voelkerding et al., *Clinical Chem.*, 55: 641-658, 2009; MacLean et al., *Nature Rev. Microbiol.*, 7: 287-296; U.S. Pat. Nos. 5,912,148; 6,130,073; each herein incorporated by reference in their entirety) also involves fragmentation of the template, ligation to oligonucleotide adaptors, attachment to beads, and clonal amplification by emulsion PCR. Following this, beads bearing template are immobilized on a derivatized surface of a glass flow-cell, and a primer complementary to the adaptor oligonucleotide is annealed. However, rather than utilizing this primer for 3' extension, it is instead used to provide a 5' phosphate group for ligation to interrogation probes containing two probe-specific bases followed by 6 degenerate bases and one of four fluorescent labels. In the SOLiD system, interrogation probes have 16 possible combinations of the two bases at the 3' end of each probe, and one of four fluors at the 5' end. Fluor color, and thus identity of each probe, corresponds to specified color-space coding schemes. Multiple rounds (usually 7) of probe annealing, ligation, and fluor detection are followed by denaturation, and then a second round of sequencing using a primer that is offset by one base relative to the initial primer. In this manner, the template sequence can be computationally re-constructed, and template bases are interrogated twice, resulting in increased accuracy. Sequence read length averages 35 nucleotides, and overall output exceeds 4 billion bases per sequencing run.

In certain embodiments, nanopore sequencing (see, e.g., Astier et al., J. Am. Chem. Soc. 2006 Feb. 8; 128(5):1705-10, herein incorporated by reference) is utilized. The theory behind nanopore sequencing has to do with what occurs when a nanopore is immersed in a conducting fluid and a potential (voltage) is applied across it. Under these conditions a slight electric current due to conduction of ions through the nanopore can be observed, and the amount of current is exceedingly sensitive to the size of the nanopore. As each base of a nucleic acid passes through the nanopore, this causes a change in the magnitude of the current through the nanopore that is distinct for each of the four bases, thereby allowing the sequence of the DNA molecule to be determined.

In certain embodiments, HeliScope by Helicos BioSciences (Voelkerding et al., *Clinical Chem.*, 55: 641-658, 2009; MacLean et al., *Nature Rev. Microbiol.*, 7: 287-296; U.S. Pat. Nos. 7,169,560; 7,282,337; 7,482,120; 7,501,245; 6,818,395; 6,911,345; 7,501,245; each herein incorporated by reference in their entirety) is utilized. Template DNA is fragmented and polyadenylated at the 3' end, with the final adenosine bearing a fluorescent label. Denatured polyadenylated template fragments are ligated to poly(dT) oligonucleotides on the surface of a flow cell. Initial physical locations of captured template molecules are recorded by a CCD camera, and then label is cleaved and washed away. Sequencing is achieved by addition of polymerase and serial addition of fluorescently-labeled dNTP reagents. Incorporation events result in fluor signal corresponding to the dNTP, and signal is captured by a CCD camera before each round of dNTP addition. Sequence read length ranges from 25-50 nucleotides, with overall output exceeding 1 billion nucleotide pairs per analytical run.

The Ion Torrent technology is a method of DNA sequencing based on the detection of hydrogen ions that are released during the polymerization of DNA (see, e.g., *Science* 327 (5970): 1190 (2010); U.S. Pat. Appl. Pub. Nos. 20090026082, 20090127589, 20100301398, 20100197507, 20100188073, and 20100137143, incorporated by reference in their entireties for all purposes). A microwell contains a template DNA strand to be sequenced. Beneath the layer of microwells is a hypersensitive ISFET ion sensor. All layers are contained within a CMOS semiconductor chip, similar to that used in the electronics industry. When a dNTP is incorporated into the growing complementary strand a hydrogen ion is released, which triggers a hypersensitive ion sensor. If homopolymer repeats are present in the template sequence, multiple dNTP molecules will be incorporated in a single cycle. This leads to a corresponding number of released hydrogens and a proportionally higher electronic signal. This technology differs from other sequencing technologies in that no modified nucleotides or optics are used. The per-base accuracy of the Ion Torrent sequencer is ~99.6% for 50 base reads, with ~100 Mb to 100Gb generated per run. The read-length is 100-300 base pairs. The accuracy for homopolymer repeats of 5 repeats in length is ~98%. The benefits of ion semiconductor sequencing are rapid sequencing speed and low upfront and operating costs.

Stratos Genomics, Inc. sequencing involves the use of Xpandomers. This sequencing process typically includes providing a daughter strand produced by a template-directed synthesis. The daughter strand generally includes a plurality of subunits coupled in a sequence corresponding to a contiguous nucleotide sequence of all or a portion of a target nucleic acid in which the individual subunits comprise a tether, at least one probe or nucleobase residue, and at least one selectively cleavable bond. The selectively cleavable bond(s) is/are cleaved to yield an Xpandomer of a length longer than the plurality of the subunits of the daughter strand. The Xpandomer typically includes the tethers and reporter elements for parsing genetic information in a sequence corresponding to the contiguous nucleotide sequence of all or a portion of the target nucleic acid. Reporter elements of the Xpandomer are then detected. Additional details relating to Xpandomer-based approaches are described in, for example, U.S. Pat. Pub No. 20090035777, entitled "High Throughput Nucleic Acid Sequencing by Expansion," filed Jun. 19, 2008, which is incorporated herein in its entirety.

Other emerging single molecule sequencing methods include real-time sequencing by synthesis using a VisiGen platform (Voelkerding et al., *Clinical Chem.,* 55: 641-58, 2009; U.S. Pat. No. 7,329,492; U.S. patent application Ser. No. 11/671,956; U.S. patent application Ser. No. 11/781, 166; each herein incorporated by reference in their entirety) in which immobilized, primed DNA template is subjected to strand extension using a fluorescently-modified polymerase and florescent acceptor molecules, resulting in detectible fluorescence resonance energy transfer (FRET) upon nucleotide addition.

2. Hybridization

Illustrative non-limiting examples of nucleic acid hybridization techniques include, but are not limited to, in situ hybridization (ISH), microarray, and Southern or Northern blot. In situ hybridization (ISH) is a type of hybridization that uses a labeled complementary DNA or RNA strand as a probe to localize a specific DNA or RNA sequence in a portion or section of tissue (in situ), or, if the tissue is small enough, the entire tissue (whole mount ISH). DNA ISH can be used to determine the structure of chromosomes. RNA ISH is used to measure and localize mRNAs and other transcripts within tissue sections or whole mounts. Sample cells and tissues are usually treated to fix the target transcripts in place and to increase access of the probe. The probe hybridizes to the target sequence at elevated temperature, and then the excess probe is washed away. The probe that was labeled with either radio-, fluorescent- or antigen-labeled bases is localized and quantitated in the tissue using either autoradiography, fluorescence microscopy or immunohistochemistry, respectively. ISH can also use two or more probes, labeled with radioactivity or the other non-radioactive labels, to simultaneously detect two or more transcripts.

In some embodiments, ESR1 mutations are detected using fluorescence in situ hybridization (FISH). In some embodiments, FISH assays utilize bacterial artificial chromosomes (BACs). These have been used extensively in the human genome sequencing project (see *Nature* 409: 953-958 (2001)) and clones containing specific BACs are available through distributors that can be located through many sources, e.g., NCBI. Each BAC clone from the human genome has been given a reference name that unambiguously identifies it. These names can be used to find a corresponding GenBank sequence and to order copies of the clone from a distributor.

The present invention further provides a method of performing a FISH assay on human cells (e.g., breast or endometrial cells). Specific protocols are well known in the art and can be readily adapted for the present invention. Guidance regarding methodology may be obtained from many references including: *In situ Hybridization: Medical Applications* (eds. G. R. Coulton and J. de Belleroche), Kluwer Academic Publishers, Boston (1992); *In situ Hybridization: In Neurobiology; Advances in Methodology* (eds. J. H. Eberwine, K. L. Valentino, and J. D. Barchas), Oxford University Press Inc., England (1994); *In situ Hybridization: A Practical Approach* (ed. D. G. Wilkinson), Oxford University Press Inc., England (1992)); Kuo, et al., *Am. J. Hum. Genet.* 49:112-119 (1991); Klinger, et al., *Am. J. Hum. Genet.* 51:55-65 (1992); and Ward, et al., *Am. J. Hum. Genet.* 52:854-865 (1993)). There are also kits that are commercially available and that provide protocols for performing FISH assays (available from e.g., Oncor, Inc., Gaithersburg, Md.). Patents providing guidance on methodology include U.S. Pat. Nos. 5,225,326; 5,545,524; 6,121, 489 and 6,573,043. All of these references are hereby incorporated by reference in their entirety and may be used along with similar references in the art and with the information provided in the Examples section herein to establish procedural steps convenient for a particular laboratory.

3. Microarrays

Different kinds of biological assays are called microarrays including, but not limited to: DNA microarrays (e.g., cDNA microarrays and oligonucleotide microarrays); protein microarrays; tissue microarrays; transfection or cell microarrays; chemical compound microarrays; and, antibody microarrays. A DNA microarray, commonly known as gene chip, DNA chip, or biochip, is a collection of microscopic DNA spots attached to a solid surface (e.g., glass, plastic or silicon chip) forming an array for the purpose of expression profiling or monitoring expression levels for thousands of genes simultaneously. The affixed DNA segments are known as probes, thousands of which can be used in a single DNA microarray. Microarrays can be used to identify disease genes or transcripts (e.g., ESR1 mutations) by comparing gene expression in disease and normal cells. Microarrays can be fabricated using a variety of technologies, including but not limiting: printing with fine-pointed pins onto glass slides; photolithography using pre-made masks; photolithography using dynamic micromirror devices; ink-jet printing; or, electrochemistry on microelectrode arrays.

Southern and Northern blotting is used to detect specific DNA or RNA sequences, respectively. DNA or RNA extracted from a sample is fragmented, electrophoretically separated on a matrix gel, and transferred to a membrane filter. The filter bound DNA or RNA is subject to hybridization with a labeled probe complementary to the sequence of interest. Hybridized probe bound to the filter is detected. A variant of the procedure is the reverse Northern blot, in which the substrate nucleic acid that is affixed to the membrane is a collection of isolated DNA fragments and the probe is RNA extracted from a tissue and labeled.

4. Amplification

Nucleic acids may be amplified prior to or simultaneous with detection. Illustrative non-limiting examples of nucleic acid amplification techniques include, but are not limited to, polymerase chain reaction (PCR), reverse transcription polymerase chain reaction (RT-PCR), transcription-mediated amplification (TMA), ligase chain reaction (LCR), strand displacement amplification (SDA), and nucleic acid sequence based amplification (NASBA). Those of ordinary skill in the art will recognize that certain amplification techniques (e.g., PCR) require that RNA be reversed transcribed to DNA prior to amplification (e.g., RT-PCR), whereas other amplification techniques directly amplify RNA (e.g., TMA and NASBA).

5. Protein Detection

In some embodiments, variant ESR1 polypeptides are detected (e.g., using immunoassays or mass spectrometry).

Illustrative non-limiting examples of immunoassays include, but are not limited to: immunoprecipitation; Western blot; ELISA; immunohistochemistry; immunocytochemistry; flow cytometry; and, immuno-PCR. Polyclonal or monoclonal antibodies detectably labeled using various techniques known to those of ordinary skill in the art (e.g., colorimetric, fluorescent, chemiluminescent or radioactive) are suitable for use in the immunoassays. Immunoprecipitation is the technique of precipitating an antigen out of solution using an antibody specific to that antigen. The process can be used to identify protein complexes present in cell extracts by targeting a protein believed to be in the complex. The complexes are brought out of solution by insoluble antibody-binding proteins isolated initially from bacteria, such as Protein A and Protein G. The antibodies can also be coupled to sepharose beads that can easily be isolated out of solution. After washing, the precipitate can be analyzed using mass spectrometry, Western blotting, or any number of other methods for identifying constituents in the complex.

A Western blot, or immunoblot, is a method to detect protein in a given sample of tissue homogenate or extract. It uses gel electrophoresis to separate denatured proteins by mass. The proteins are then transferred out of the gel and onto a membrane, typically polyvinyldiflroride or nitrocellulose, where they are probed using antibodies specific to the protein of interest. As a result, researchers can examine the amount of protein in a given sample and compare levels between several groups.

An ELISA, short for Enzyme-Linked ImmunoSorbent Assay, is a biochemical technique to detect the presence of an antibody or an antigen in a sample. It utilizes a minimum of two antibodies, one of which is specific to the antigen and the other of which is coupled to an enzyme. The second antibody will cause a chromogenic or fluorogenic substrate to produce a signal. Variations of ELISA include sandwich ELISA, competitive ELISA, and ELISPOT. Because the ELISA can be performed to evaluate either the presence of antigen or the presence of antibody in a sample, it is a useful tool both for determining serum antibody concentrations and also for detecting the presence of antigen.

Immuno-polymerase chain reaction (IPCR) utilizes nucleic acid amplification techniques to increase signal generation in antibody-based immunoassays. Because no protein equivalence of PCR exists, that is, proteins cannot be replicated in the same manner that nucleic acid is replicated during PCR, the only way to increase detection sensitivity is by signal amplification. The target proteins are bound to antibodies which are directly or indirectly conjugated to oligonucleotides. Unbound antibodies are washed away and the remaining bound antibodies have their oligonucleotides amplified. Protein detection occurs via detection of amplified oligonucleotides using standard nucleic acid detection methods, including real-time methods.

Mass spectrometry has proven to be a valuable tool for the determination of molecular structures of molecules of many kinds, including biomolecules, and is widely practiced today. Purified proteins are digested with specific proteases (e.g. trypsin) and evaluated using mass spectrometry. Many alternative methods can also be used. For instance, either matrix-assisted laser desorption/ionization (MALDI) or electrospray ionization (ESI) mass spectrometric methods can be used. Furthermore, mass spectroscopy can be coupled with the use of two-dimensional gel electrophoretic separation of cellular proteins as an alternative to comprehensive pre-purification. Mass spectrometry can also be coupled with the use of peptide fingerprint database and various searching algorithms. Differences in post-translational modification, such as phosphorylation or glycosylation, can also be probed by coupling mass spectrometry with the use of various pretreatments such as with glycosylases and phosphatases. All of these methods are to be considered as part of this application.

In some embodiments, electrospray ionisation quadrupole mass spectrometry is utilized to detect ESR1 variants (See e.g., U.S. Pat. No. 8,658,396; herein incorporated by reference in its entirety).

6. Data Analysis

In some embodiments, a computer-based analysis program is used to translate the raw data generated by the detection assay (e.g., the presence, absence, or amount of a given marker or markers) into data of predictive value for a clinician. The clinician can access the predictive data using any suitable means. Thus, in some preferred embodiments, the present invention provides the further benefit that the clinician, who is not likely to be trained in genetics or molecular biology, need not understand the raw data. The data is presented directly to the clinician in its most useful form. The clinician is then able to immediately utilize the information in order to optimize the care of the subject.

The present invention contemplates any method capable of receiving, processing, and transmitting the information to and from laboratories conducting the assays, information provides, medical personal, and subjects. For example, in some embodiments of the present invention, a sample (e.g., a biopsy or a serum sample) is obtained from a subject and submitted to a profiling service (e.g., clinical lab at a medical facility, genomic profiling business, etc.), located in any part of the world (e.g., in a country different than the country where the subject resides or where the information is ultimately used) to generate raw data. Where the sample comprises a tissue or other biological sample, the subject may visit a medical center to have the sample obtained and sent to the profiling center, or subjects may collect the sample themselves (e.g., a urine sample) and directly send it to a profiling center. Where the sample comprises previously determined biological information, the information may be directly sent to the profiling service by the subject (e.g., an information card containing the information may be scanned by a computer and the data transmitted to a computer of the profiling center using an electronic communication systems). Once received by the profiling service, the sample is processed and a profile is produced (i.e., ESR1 variant data), specific for the diagnostic or prognostic information desired for the subject.

The profile data is then prepared in a format suitable for interpretation by a treating clinician. For example, rather than providing raw expression data, the prepared format may represent a diagnosis or risk assessment (e.g., presence or absence of a mutation in ESR1) for the subject, along with recommendations for particular treatment options. The data may be displayed to the clinician by any suitable method. For example, in some embodiments, the profiling service generates a report that can be printed for the clinician (e.g., at the point of care) or displayed to the clinician on a computer monitor.

In some embodiments, the information is first analyzed at the point of care or at a regional facility. The raw data is then sent to a central processing facility for further analysis and/or to convert the raw data to information useful for a clinician or patient. The central processing facility provides the advantage of privacy (all data is stored in a central facility with uniform security protocols), speed, and uniformity of data analysis. The central processing facility can then control the fate of the data following treatment of the subject. For example, using an electronic communication system, the central facility can provide data to the clinician, the subject, or researchers.

In some embodiments, the subject is able to directly access the data using the electronic communication system. The subject may chose further intervention or counseling based on the results. In some embodiments, the data is used for research use. For example, the data may be used to further optimize the inclusion or elimination of markers as useful indicators of a particular condition or stage of disease or as a companion diagnostic to determine a treatment course of action.

6. Compositions & Kits

Compositions for use in the diagnostic methods described herein include, but are not limited to, probes, amplification oligonucleotides, and the like. In some embodiments, kits include all components necessary, sufficient or useful for detecting the markers described herein (e.g., reagents, controls, instructions, etc.). The kits described herein find use in research, therapeutic, screening, and clinical applications.

The probe and antibody compositions of the present invention may also be provided in the form of an array.

In some embodiments, the present invention provides one or more nucleic acid probes or primers having 8 or more (e.g., 10 or more, 12 or more, 15 or more, 18 or more, etc.) nucleotides, and that specifically bind to nucleic acids encoding a variant ESR polypeptide but not the wild type nucleic acid. In some embodiments, the present invention provides an antibody that specifically binds to variant ESR1 polypeptides but not wild type ESR1 polypeptides.

Embodiments of the present invention provide complexes of ESR1 nucleic acids or polypeptides with nucleic acid primers or probes or antibodies. In some embodiments, the primers, probes, or antibodies bind only to the variant or mutant forms of ESR1 described herein. In some embodiments, a reaction mixture comprising a mutant ESR1 polypeptide and an antibody that specifically binds to the variant amino acid sequence is provided. In some embodiments, the present invention provides a multiplex (e.g., microarray) comprising reagents that binds to two or more variant ESR1 amino acid or nucleic acids.

III. Treatment Methods

Embodiments of the present disclosure provide methods of determining a treatment course of action and administering an anti-cancer treatment. For example, in some embodiments, subjects diagnosed with cancer (e.g., endometrial cancer or breast cancer) are screened for the presence or absence of one or more of the ESR1 mutations described herein (e.g., p.Leu536Gln, p.Tyr537Ser, p.Tyr537Cys, or p.Tyr537Asn) and the results are used to determine a treatment course of action. For example, in some embodiments, subjects identified as having one or more of the ESR1 mutations before beginning treatment or that develop during treatment are administered an estrogen receptor antagonist (e.g., tamoxifen or fulvestrant). In some embodiments, subjects not found to have the ESR1 variants are not administered an estrogen receptor antagonist.

In some embodiments, patients currently undergoing cancer treatment (e.g., with an aromatase inhibitor such as, for example, exemestane, anastrozole and letrozole) are screened for the presence or absence of one or more mutations in ESR1. In some embodiments, subjects found to have the mutations are administered an estrogen receptor antagonist in addition to or instead of the aromatase inhibitor.

In some embodiments, assays for ESR1 mutations are repeated (e.g., before, during or after anticancer treatment). In some embodiments, assays are repeated daily, weekly, monthly, annually, or less often.

EXPERIMENTAL

The following examples are provided in order to demonstrate and further illustrate certain preferred embodiments and aspects of the present invention and are not to be construed as limiting the scope thereof.

Example 1

A. Methods

Clinical Study and Specimen Collection Sequencing of clinical samples was performed under Institutional Review Board (IRB)-approved studies at the University of Michigan. Patients were enrolled and consented for integrative tumor sequencing, MI-ONCOSEQ (Michigan Oncology Sequencing Protocol, IRB# HUM00046018). Medically qualified patients 18 years or older with advanced or refractory cancer were eligible for the study. Informed consent details the risks of integrative sequencing and includes up-front genetic counseling. Informed consent was obtained from all subjects included in this study. Biopsies were arranged for safely accessible tumor sites. Needle biopsies were snap frozen in OCT and a longitudinal section was cut. Hematoxylin and eosin (H&E) stained frozen sections were reviewed by pathologists to identify cores with highest tumor content. Remaining portions of each needle biopsy core were retained for nucleic acid extraction.

Extraction of DNA and RNA

Genomic DNA from frozen needle biopsies and blood was isolated using the Qiagen DNeasy Blood & Tissue Kit, according to the manufacturer's instructions. Total RNA was extracted from frozen needle biopsies using the Qiazol reagent with disruption using a 5 mm bead on a Tissuelyser II (Qiagen), and purified using a miRNeasy kit (Qiagen) with DNase I digestion, according to the manufacturer's instructions. RNA integrity was verified on an Agilent 2100 Bioanalyzer using RNA Nano reagents (Agilent Technologies).

Preparation of Next Generation Sequencing Libraries

Transcriptome libraries were prepared using 1-2 µg of total RNA. Poly(A)+RNA was isolated using Sera-Mag oligo(dT) beads (Thermo Scientific) and fragmented with the Ambion Fragmentation Reagents kit (Ambion, Austin, Tex.). cDNA synthesis, end-repair, A-base addition, and ligation of the Illumina indexed adapters were performed according to Illumina's TruSeq RNA protocol (Illumina). Libraries were size-selected for 250-300 bp cDNA fragments on a 3% Nusieve 3:1 (Lonza) agarose gel, recovered using QIAEX II gel extraction reagents (Qiagen), and PCR-amplified using Phusion DNA polymerase (New England Biolabs). The amplified libraries were purified using AMPure XP beads (Beckman Coulter). Library quality was measured on an Agilent 2100 Bioanalyzer for product size and concentration. Paired-end libraries were sequenced with the Illumina HiSeq 2000, (2×100 nucleotide read length). Reads that passed the chastity filter of Illumina BaseCall software were used for subsequent analysis.

Exome libraries of matched pairs of tumor/normal genomic DNAs were generated using the Illumina TruSeq DNA Sample Prep Kit, following the manufacturer's instructions. In brief, 1-3 µg of each genomic DNA was sheared using a Covaris S2 to a peak target size of 250 bp. Fragmented DNA was concentrated using AMPure XP beads, followed by end-repair, A-base addition, and ligation of the Illumina indexed adapters. The adapter-ligated libraries were electrophoresed on 3% Nusieve agarose gels (Lonza) and fragments between 300 to 350 bp were recovered using QIAEX II gel extraction reagents (Qiagen). Recovered DNA was amplified using Illumina index primers for 8 cycles, purified using AMPure XP beads, and the DNA concentration was determined using a Nanodrop spectrophotometer. 1 μg of the library was hybridized to the Agilent SureSelect Human All Exon V4 at 65° C. for 60 hr following the manufacturer's protocol (Agilent). The targeted exon fragments were captured on Dynal M-280 streptavidin beads (Invitrogen), and enriched by amplification with the Illumina index primers for 9 additional PCR cycles. PCR products were purified with AMPure XP beads and analyzed for quality and quantity using an Agilent 2100 Bioanalyzer and DNA 1000 reagents.

The publicly available software FastQC was used to assess sequencing quality. For each lane, the per-base quality scores were examined across the length of the reads. Lanes were deemed passing if the per-base quality score boxplot indicated that >85% of the reads had >Q20 for bases 1-100. In addition to the raw sequence quality, alignment quality was assessed using the Picard package. This allows monitoring of duplication rates and chimeric reads that may result from ligation artifacts; crucial statistics for interpreting the results of copy number and structural variant analysis.

Gene Fusion Detection

Paired-end transcriptome sequencing reads were aligned to the human reference genome (GRCh37/hg19) using a RNA-Seq spliced read mapper Tophat2 (Kim, D. & Salzberg, S. L. Genome Biol 12, R72 (2011) (Tophat 2.0.4), with '—fusion-search' option turned on to detect potential gene fusion transcripts. In the initial process, Tophat2 internally deploys an ultrafast short read alignment tool Bowtie (Version 0.12.8) to map the transcriptome data. Potential false positive fusion candidates were filtered out using 'Tophat-Post-Fusion' module. Further, the fusion candidates were manual examined for annotation and ligation artifacts. Junction reads supporting the fusion candidates were re-aligned using an alignment tool BLAT to reconfirm the fusion breakpoint. Full length sequence of the fusion gene was constructed based on supporting junction reads, and evaluated for potential open reading frames (ORF) using an ORF finder. Further, the gene fusions with robust ORFs, the amino acid sequences of the fused proteins were explored using the Simple Modular Architecture Research Tool (SMART) to examine the gain or loss of known functional domains in the fusion proteins.

Gene Expression

The BAM file 'accepted_hits.bam' which was generated by the Tophat mapping module, was utilized to quantify the expression data, through Cufflinks (Trapnell, C. et al. Nat Protoc 7, 562-78 (2012)) (Version 2.0.2), an isoform assembly and RNA-Seq quantitation package. Structural features of 56,369 transcripts from the Ensemble resource (Ensemble66) was used as an annotation reference for quantifying expression of individual transcripts/isoforms. The 'Max Bundle Length' parameter was set to '10000000' and 'multi-read-correct' is flagged on to perform an initial estimation procedure to more accurately weight reads mapping to multiple locations in the genome.

Mutation Analysis

Whole-exome sequencing was performed on Illumina HiSeq 2000 or HiSeq 2500 in paired-end mode and the primary base call files were converted into FASTQ sequence files using the bcl2fastq converter tool bcl2fastq-1.8.4 in the CASAVA 1.8 pipeline. The FASTQ sequence files generated were then processed through an in-house pipeline constructed for whole-exome sequence analyses of paired cancer genomes. The sequencing reads were aligned to the reference genome build hg19, GRCh37 using Novoalign Multithreaded (Version2.08.02) (Novocraft) and converted into BAM files using SAMtools (Version 0.1.18) (Li, H. et al. Bioinformatics 25, 2078-9 (2009)). Sorting and indexing of BAM files utilized Novosort threaded (Version 1.00.01) and duplicates reads were removed using Picard (Version 1.74). Mutation analysis was performed using VarScan2 algorithms (Version2.3.2) (Koboldt, D. C. et al. Genome Res 22, 568-76 (2012)) utilizing the pileup files created by SAMtools mpileup for tumor and matched normal samples, simultaneously performing the pairwise comparisons of base call and normalized sequence depth at each position. For single nucleotide variant detection, filtering parameters including coverage; variant read support, variant frequency, P-value, base quality, homopolymer, and strandedness are applied. For indels analysis Pindel (Version 0.2.4) was used on tumor and matched normal samples and indels common in both samples were classified as germline and indels present in tumor but not in normal were classified as somatic. Finally, the list of candidate indels as well as somatic and/or germline mutations was generated by excluding synonymous SNVs. ANNOVAR (Wang, K., Li, M. & Hakonarson, H. Nucleic Acids Res 38, e164 (2010)) was used to functionally annotate the detected genetic variants and positions are based on Ensemble66 transcript sequences.

Tumor content for each tumor exome library was estimated from the sequence data by fitting a binomial mixture model with two components to the set of most likely SNV candidates on 2-copy genomic regions. The set of candidates used for estimation consisted of coding variants that (1) exhibited at least 3 variant fragments in the tumor sample, (2) exhibited zero variant fragments in the matched benign sample with at least 16 fragments of coverage, (3) were not present in dbSNP, (4) were within a targeted exon or within 100 base pairs of a targeted exon, (5) were not in homopolymer runs of four or more bases, and (6) exhibited no evidence of amplification or deletion. In order to filter out regions of possible amplification or deletion, we used exon coverage ratios to infer copy number changes, as described below. Resulting SNV candidates were not used for estimation of tumor content if the segmented log-ratio exceeded 0.2 in absolute value. Candidates on the Y chromosome were also eliminated because they were unlikely to exist in 2-copy genomic regions. Using this set of candidates, we fit a binomial mixture model with two components using the R package flexmix, version 2.3-8. One component consisted of SNV candidates with very low variant fractions, presumably resulting from recurrent sequencing errors and other artifacts. The other component, consisting of the likely set of true SNVs, was informative of tumor content in the tumor sample. Specifically, under the assumption that most or all of the observed SNV candidates in this component are heterozygous SNVs, we expect the estimated binomial proportion of this component to represent one-half of the proportion of tumor cells in the sample. Thus, the estimated binomial proportion as obtained from the mixture model was doubled to obtain an estimate of tumor content.

Copy number aberrations were quantified and reported for each gene as the segmented normalized log 2-transformed exon coverage ratios between each tumor sample and matched normal sample (Lonigro, R. J. et al. Neoplasia 13, 1019-25 (2011)). To account for observed associations between coverage ratios and variation in GC content across the genome, lowess normalization was used to correct per-exon coverage ratios prior to segmentation analysis. Specifically, mean GC percentage was computed for each targeted region, and a lowess curve was fit to the scatterplot of log 2-coverage ratios vs. mean GC content across the targeted exome using the lowess function in R (version 2.13.1) with smoothing parameter f=0.05.

Partially redundant sequencing of areas of the genome affords the ability for cross validation of findings. We cross-validated exome-based point mutation calls by manually examining the genomic and transcriptomic reads covering the mutation using the UCSC Genome Browser. Likewise, gene fusion calls from the transcriptome data can be further supported by structural variant detection in the genomic sequence data, as well as copy number information derived from the genome and exome sequencing.

Chemicals and Reagents

β-Estradiol, (Z)-4-Hydroxytamoxifen, (E/Z)-Endoxifen Hydrochloride Hydrate, and Fulvestrant were purchased from Sigma-Aldrich.

Plasmids and Cloning cDNA for the wild type ESR1 was PCR amplified from a breast cell line MCF7 with the introduction of an N-terminal FLAG tag. cDNA encoding the relevant mutations of ESR1 were generated by site-directed mutagenesis (QuikChange, Agilent) and full-length constructs were fully sequenced. All the ESR1 variants were placed in the Lentivial vector pCDH (System Biosciences) for eukaryotic expression.

ERE-Luciferase Reporter Assay

For cell transfection experiments, HEK-293T cells were plated at a density of $1-2 \times 10^5$ per well (24-well plates) in phenol red-free Dulbecco's modified Eagle's medium (DMEM) containing 10% fetal bovine serum (FBS) and antibiotics. Once cells attached, replaced medium with DMEM containing 10% charcoal-dextran treated FBS (HyClone) and cultured overnight. The next day, cells were transiently co-transfected with ESR1-expression plasmid at 50 ng/well and luciferase reporter constructs at 25 ng per well (SABiosciences) using the FuGene 6 reagent (Promega). The ER-responsive luciferase plasmid encoding the firefly luciferase reporter gene is driven by a minimal CMV promoter and tandem repeats of the estrogen transcriptional response element (ERE). A second plasmid constitutively expressing Renilla luciferase is served as an internal control for normalizing transfection efficiencies (Cignal ERE Reporter, SABiosciences). After transfection for 18 hrs, cells were serum-starved for a few hours before treatment with 13-estradiol or anti-estrogen drugs. Cells were harvested 18 hr post-treatment, and luciferase activity was measured using the Dual-Luciferase Reporter Assay System (Promega). IC50 values were computed using the GraphPad Prizm application to fit a four parameter doseresponse curve.

Results

Advances in high-throughput sequencing technologies are beginning to establish a molecular taxonomy for a spectrum of human diseases and facilitate a move towards "precision medicine" (Chin, L., et al., Nat Med 17, 297-303 (2011); Meyerson, M., et al., Nat Rev Genet 11, 685-96 (2010)). With regards to oncology, defining the mutational landscape of an individual patient's tumor leads to more precise treatment and management of cancer patients. Comprehensive clinical sequencing programs for cancer patients have been initiated at a variety of medical centers (Roychowdhury, S. et al. Sci Transl Med 3, 111ra121 (2011); Welch, J. S. et al. JAMA 305, 1577-84 (2011)). In addition to the potential of identifying "actionable" therapeutic targets in cancer patients, these clinical sequencing efforts also shed light on acquired resistance mechanisms developed to targeted therapies (Gorre, M. E. et al. Science 293, 876-80 (2001); Korpal, M. et al. Cancer Discov (2013); Joseph, J. D. et al. Cancer Discov (2013)). ER is the primary therapeutic target in breast cancer and is expressed in 70% of cases (Ariazi, E. A., et al., Curr Top Med Chem 6, 181-202 (2006)). Drugs directly antagonizing ER such as tamoxifen and fulvestrant are a mainstay of breast cancer treatment, however approximately 30% of ER positive breast cancer exhibit de novo resistance while 40% acquire resistance to these therapies (Riggins, R. B., et al., Cancer Lett 256, 1-24 (2007)). In addition to anti-estrogen therapies, ER-positive breast cancer patients are also treated with aromatase inhibitors such as letrozole or exemestane (Lonning, P. E. & Eikesdal, H. P. Endocr Relat Cancer 20, R183-201 (2013)). Aromatase inhibitors block peripheral conversion of androgens to estrogen, and in post-menopausal women, lead to over a 98% decrease in circulating levels of estrogen. Like anti-estrogens, patients treated with aromatase inhibitors develop resistance, but presumably due to different mechanisms. Breast cancer patients that develop resistance to aromatase inhibitors, often still respond to anti-estrogen therapies (Ingle, J. N. et al. J Clin Oncol 24, 1052-6 (2006)). The molecular mechanisms of endocrine resistance in ER positive breast cancer continues to be an active area of research (Osborne, C. K. & Schiff, R. Mechanisms of endocrine resistance in breast cancer. Annu Rev Med 62, 233-47 (2011)).

The clinical sequencing program, called MI-ONCOSEQ (the Michigan Oncology Sequencing Program), enrolls patients with advanced cancer across all histologies (Welch et al., supra). Since April of 2011, it has enrolled over 200 patients by obtaining a current tumor biopsy with matched normal samples (blood and/or buccal swab). The samples are then subjected to integrative sequencing which includes whole exome sequencing of the tumor and matched normal, transcriptome sequencing, and as needed, low pass whole genome sequencing (Welch et al., supra). This combination of DNA and RNA sequencing technologies allows one to be relatively comprehensive with regards to the mutational landscape of coding genes including point mutations, indels, amplifications, deletions, gene fusions/translocations, and outlier gene expression. These results are generated within a 5 to 7 week time frame and are presented at an institutional "precision medicine tumor board" to deliberate upon potentially actionable findings.

Figure 5:
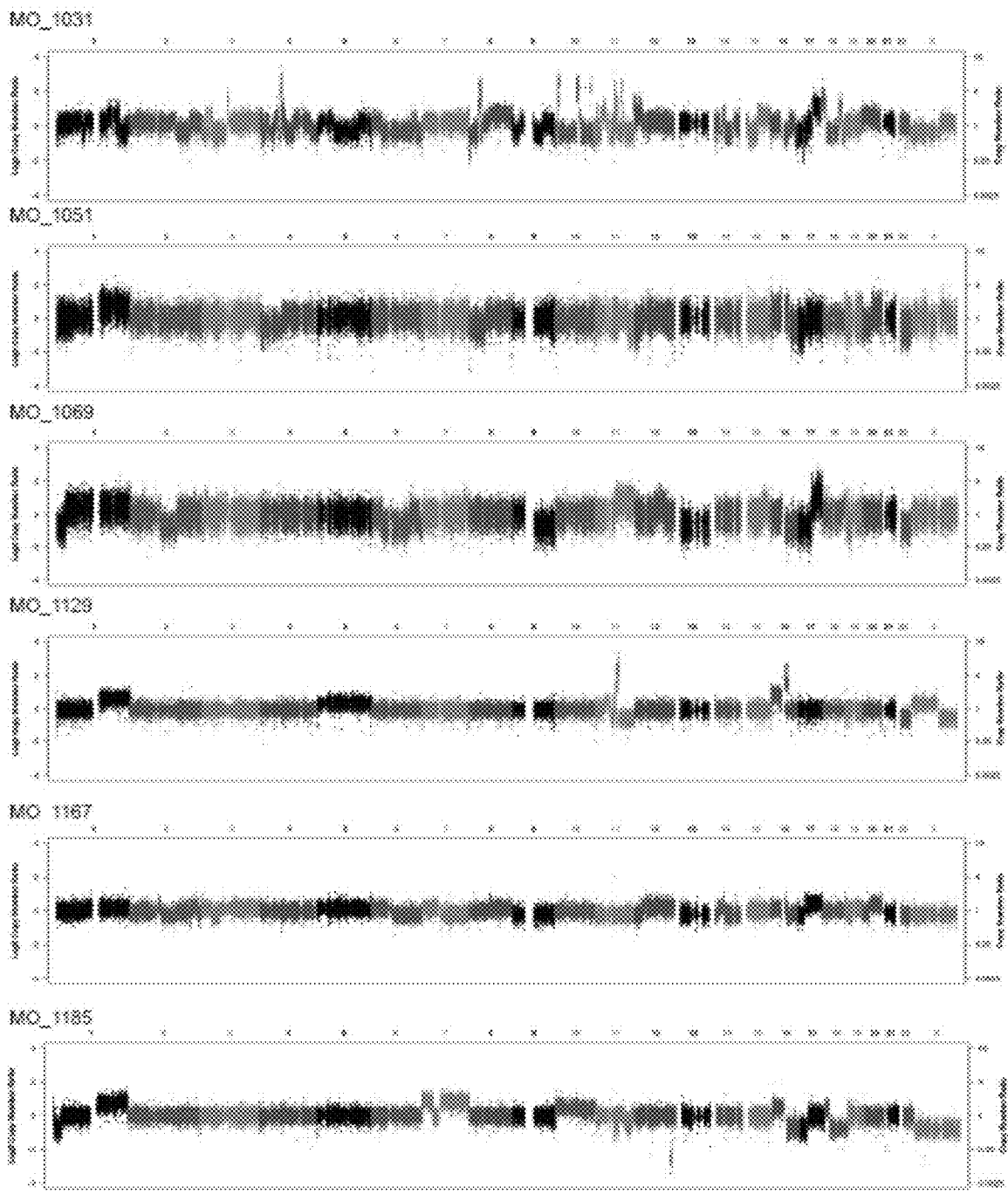
FIG. 5 shows that gene copy number landscape of the six index cases as assessed by whole exome sequencing matched to germline.
Figure 6:
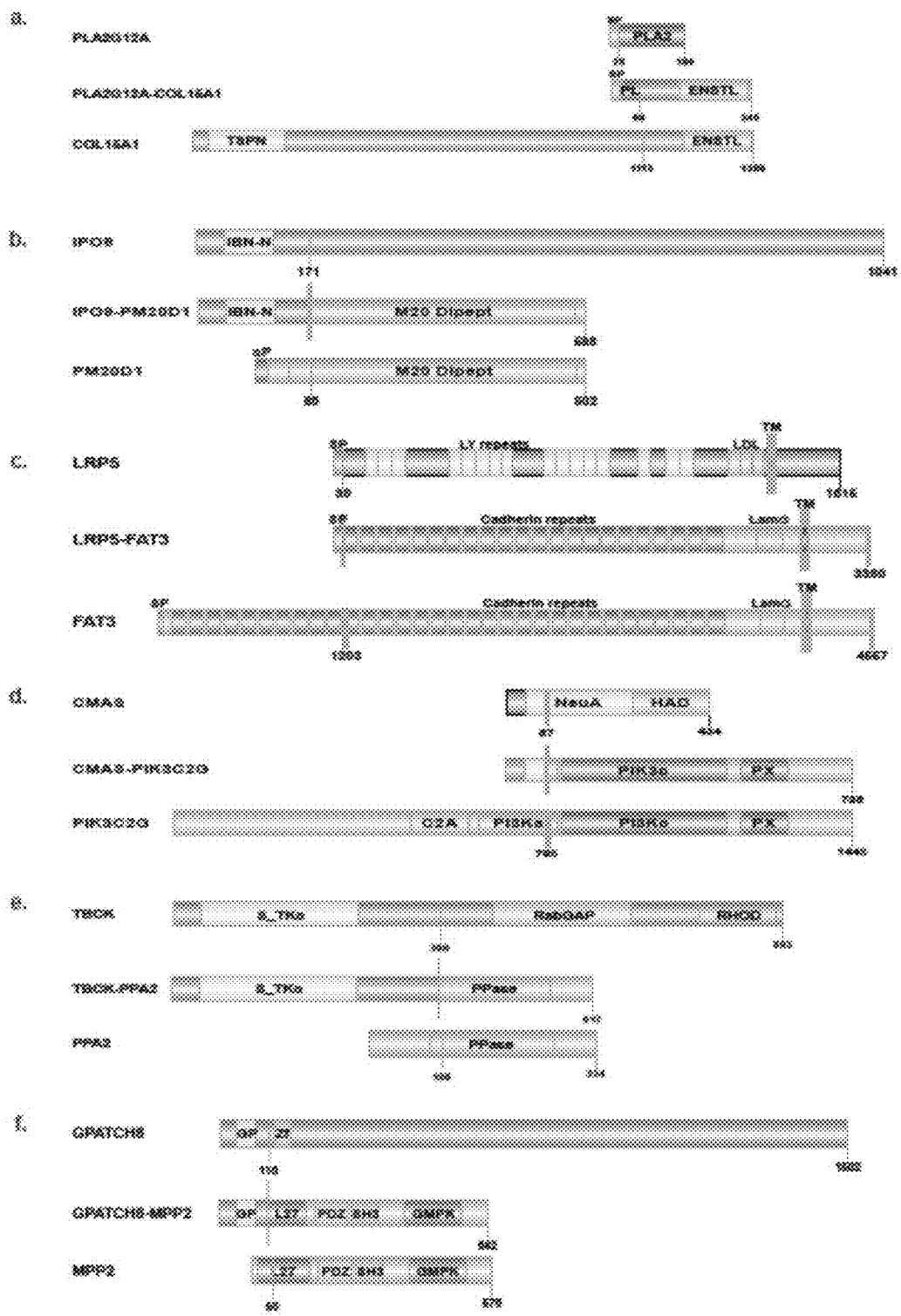
FIG. 6 shows schematic representations of the predicted gene fusions identified by transcriptome sequencing in four breast cancer index cases. a, MO 1031: PLA2G12A-COL15A1. b, MO_1031: IPO9-PM20D1. c, MO 1031: LRP5-FAT3. d, MO_1051:CMASPIK3C2G. e, MO 1051: TBCK-PPA2. f, MO_1051: GPATCH8-MPP2. g, MO_1051: FGFR2-AFF3. h, MO_1069: UBN2-TTC26. i, MO_1069: TBCD-FOXK2. j, MO_1129: DDB1-PAK1. k, MO_1129: VPS35-SLCO2B1.
Figure 6:
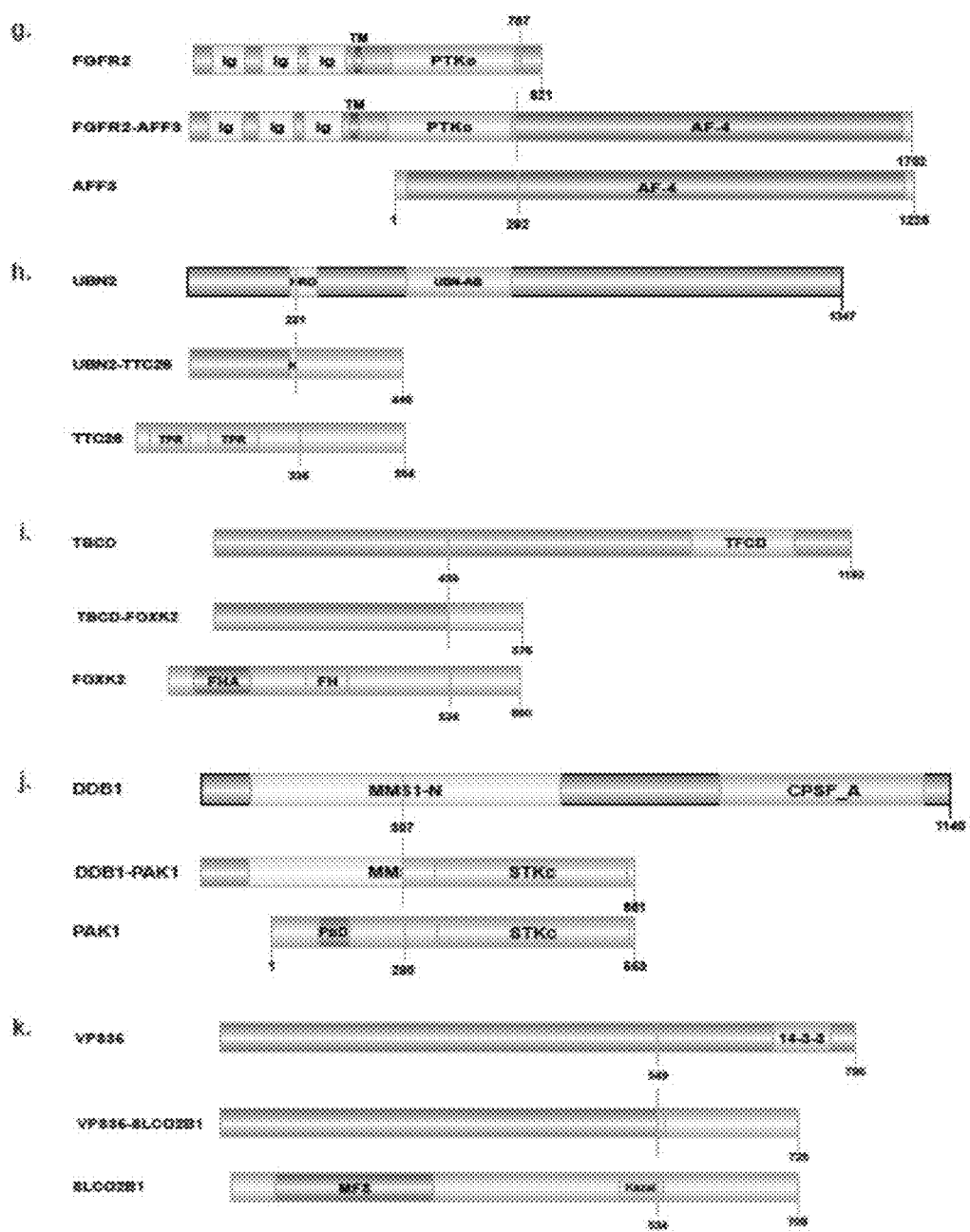

As part of the MI-ONCOSEQ program, 11 patients with metastatic ER-positive breast cancer were subjected to sequencing analysis (Tables 1 and 2). A diverse array of aberrations were identified in individual patients, including mutations in PIK3CA (n=4), BRCA1 aberrations (n=2), FGFR2 aberrations (n=2) (Wu, Y. M. et al. Identification of Targetable FGFR Gene Fusions in Diverse Cancers. Cancer Discov 3, 636-647 (2013)), NOTCH2 frameshift deletion (n=1), cyclins and associated cyclin-dependent kinase aberrations (n=3), and MDM2 amplification/overexpression (n=1). Aberrations were also found frequently in the tumor suppressor TP53 (n=6), DNA mismatch repair gene MSH2 (n=1), and epigenetic regulators (n=2) including ARID2, ARID1A, SMARCA4, among others. The complete spectrum of somatic mutations with associated expression levels and copy number alterations in the index cases are given in Tables 3 and 4, and FIG. 5. Two of the index cases, MO_1031 and MO_1051, exhibited a high level of mutations consistent with the "Signature B" identified in a whole genome study of mutational processes in breast cancer (Nik-Zainal, S. et al. *Cell* 149, 979-93 (2012)). There were 39 gene fusions identified in the 6 index cases with 11 encoding in-frame fusion proteins (Table 5 and FIG. 6), including an activating fusion of FGFR2-AFF3 (Wu et al., supra).

Nonsynonymous mutations were identified in the LBD of ESR1 (n=6). The six index patients MO_1031, MO_1051, MO_1069, MO_1129, MO_1167, and MO_1185 had LBD mutations in amino acids p.Leu536Gln, p.Tyr537Ser, p.Asp538Gly, p.Tyr537Ser, p.Asp538Gly, and p.Tyr537Ser, respectively. The respective mutation in each case was detected by whole exome sequencing of the tumor relative to matched normal, as well as corroborated with whole transcriptome sequencing since ESR1 was expressed at moderate to high levels (Table 3). The clinical histories of the index patients are depicted as timelines in FIG. 1. For three of the patients (MO_1051, MO_1069, and MO_1129), primary diagnostic material showed that the ESR1 mutations were not present at an earlier stage, indicating that they were acquired after endocrine therapy (FIG. 1 and Table 3). All of the index patients were treated with anti-estrogens (tamoxifen and/or fulvestrant) and aromatase inhibitors (letrozole, anastrozole, and/or exemestane). Two of the patients also had an oophorectomy. Comparison of the mutations present in each primary versus post-treatment pair showed a significant number of shared mutations in both samples of the pair, including activating mutations in PIK3CA in two of the cases. Thus, it is clear that the index patients presented with recurrent disease of the original primary tumor surviving in an estrogen deprived state, and presenting with acquired ESR1 mutations. Of note, neither ESR1 amplifications nor gene fusions were observed in these patients.

Figure 2:
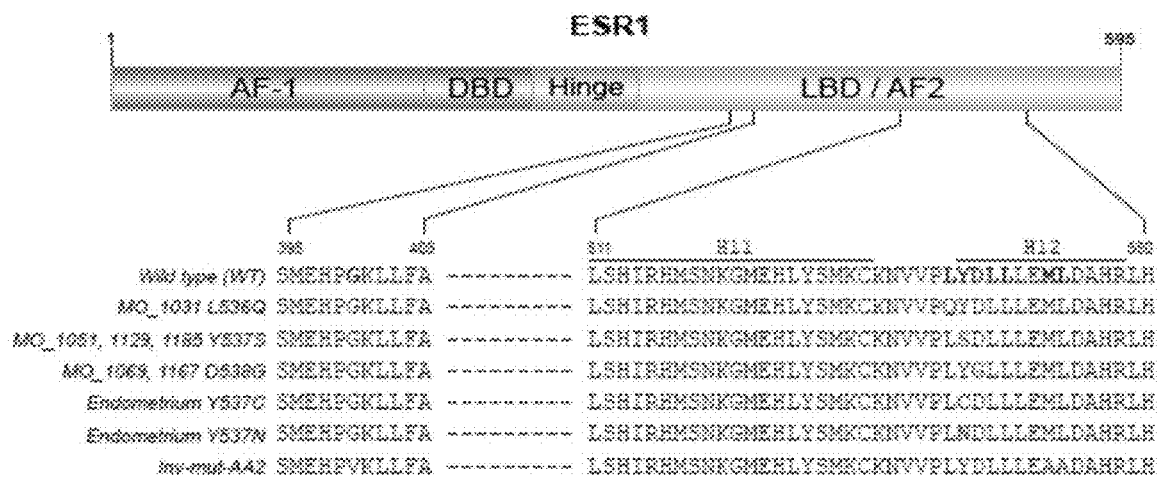
FIG. 2 shows a schematic representation of ESR1 mutations identified in the experiments described herein.
Figure 3:
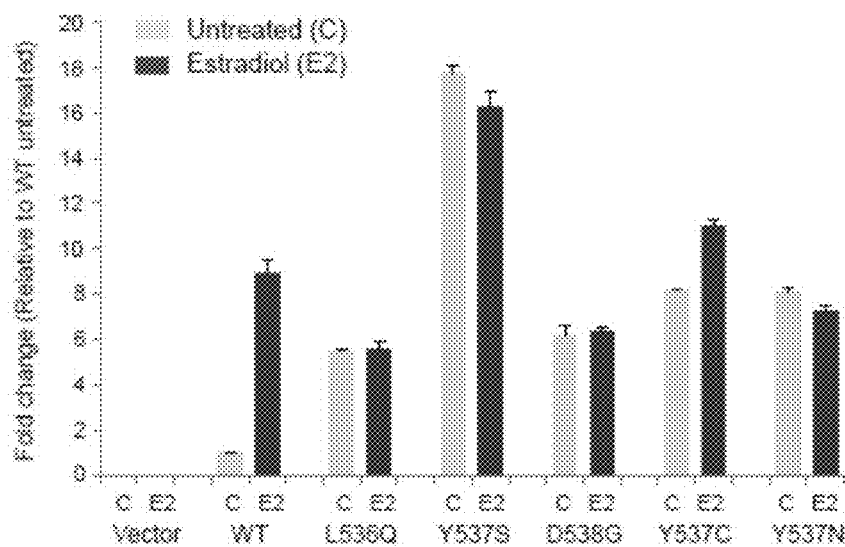
FIG. 3 shows that acquired ESR1 mutations are constitutively active.
Figure 4:
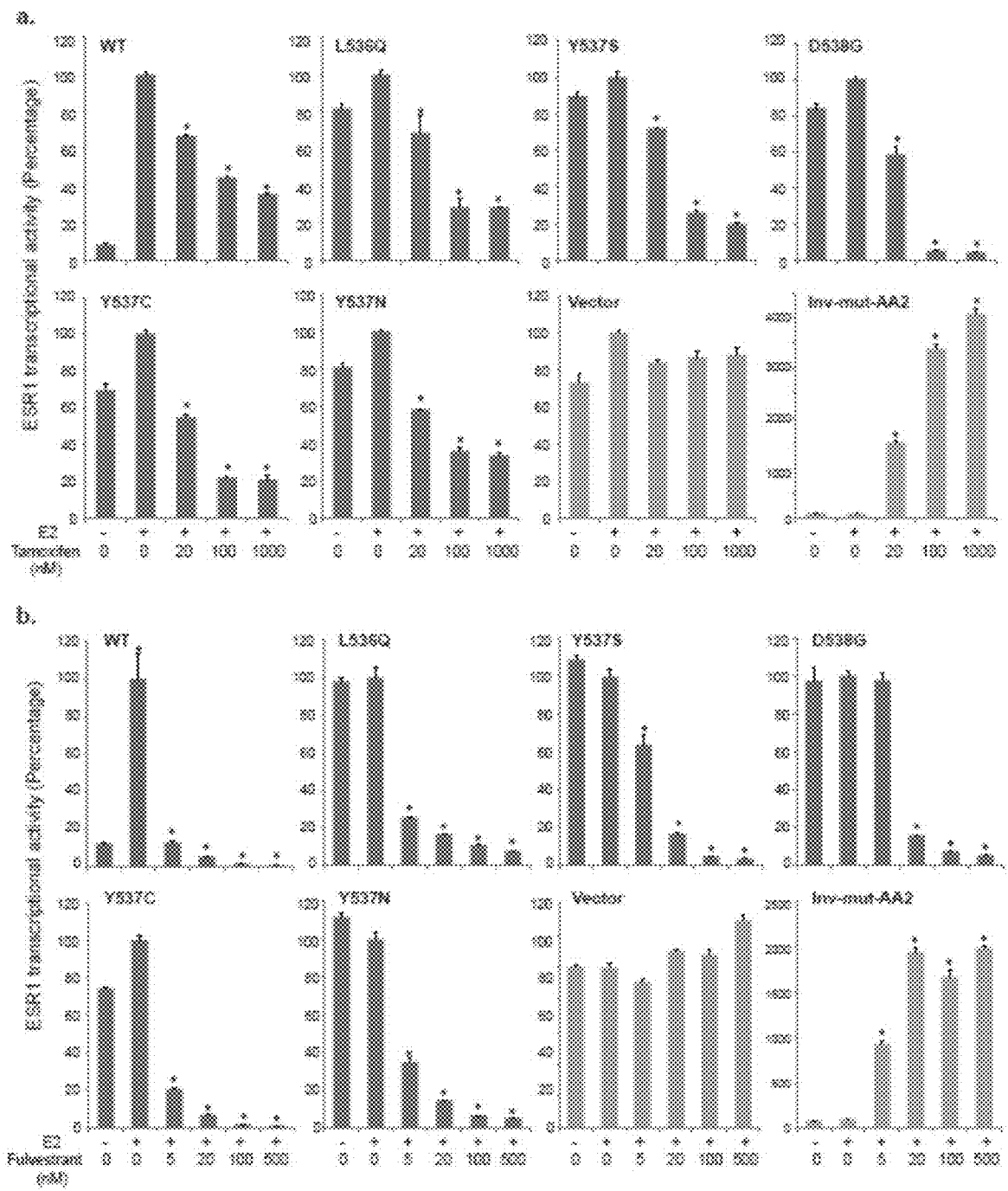
FIG. 4 shows that acquired ESR1 mutations maintain sensitivity to antiestrogen therapies. Steroid hormone-deprived cells were either untreated or treated with increasing doses of antiestrogen drugs tamoxifen (A) or fulvestrant (B) in the presence of 5 nM of β-estradiol (E2) for 24 hrs.

The 5 novel LBD mutations of ESR1 identified in this study are depicted in FIG. 2. Each occur in the vicinity of the synthetic mutations of ESR1 which are inverted in response to tamoxifen and involve amino acid alterations p.Met543Ala and p.Leu544Ala (Inv-mut-AA2) (Feil, R., et al., Biochem Biophys Res Commun 237, 752-7 (1997)) and served as a positive control for our subsequent in vitro studies. It was next assessed whether tumor types other than ER positive metastatic hormone-resistant breast cancer also acquire ligand binding mutations in ESR1. The Cancer Genome Atlas Project (TCGA), which has generated whole exome data on 27 tumor types across at least 4000 individual samples was utilized. LBD mutations of ESR1 were not detected in the 390 ER-positive breast cancers sequenced by TCGA, as these were primary resection samples before hormonal treatment (TCGA. Comprehensive molecular portraits of human breast tumours. *Nature* 490, 61-70 (2012)), nor have we detected ESR1 mutations in a cohort of 80 triple negative breast carcinoma transcriptomes (unpublished data). As the LBD mutations of ESR1 we identified were somatic and acquired after treatment, we next assessed whether they were dependent on estrogen for activation. We cloned into expression vectors each of the five ESR1 mutations identified in this study (p.Leu536Gln, p.Tyr537Ser, p.Asp538Gly, p.Tyr537Cys, and p.Tyr573Asn) and subsequently co-transfected them into HEK-293 cells with an ERE-luciferase reporter system. Steroid hormone deprived cells were then exposed to β-estradiol for 24 hours and ER reporter levels assessed. Unlike wild-type ER which had little ER reporter activity in the absence of ligand, all 5 of the ESR1 mutations exhibited strong constitutive activation of the ER reporter that was not markedly enhanced with β-estradiol (FIG. 3). This indicated that each of the mutations developed in the context of evolution during an estrogen deprived state. Consistent with this, a whole genome sequencing study of 46 cases of estrogen receptor positive breast cancer patients on two aromatase inhibitor trials did not identify any of these ESR1 mutations in the pretreatment samples analyzed (Ellis, M. J. et al. Nature 486, 353-60 (2012)).

Figure 7:
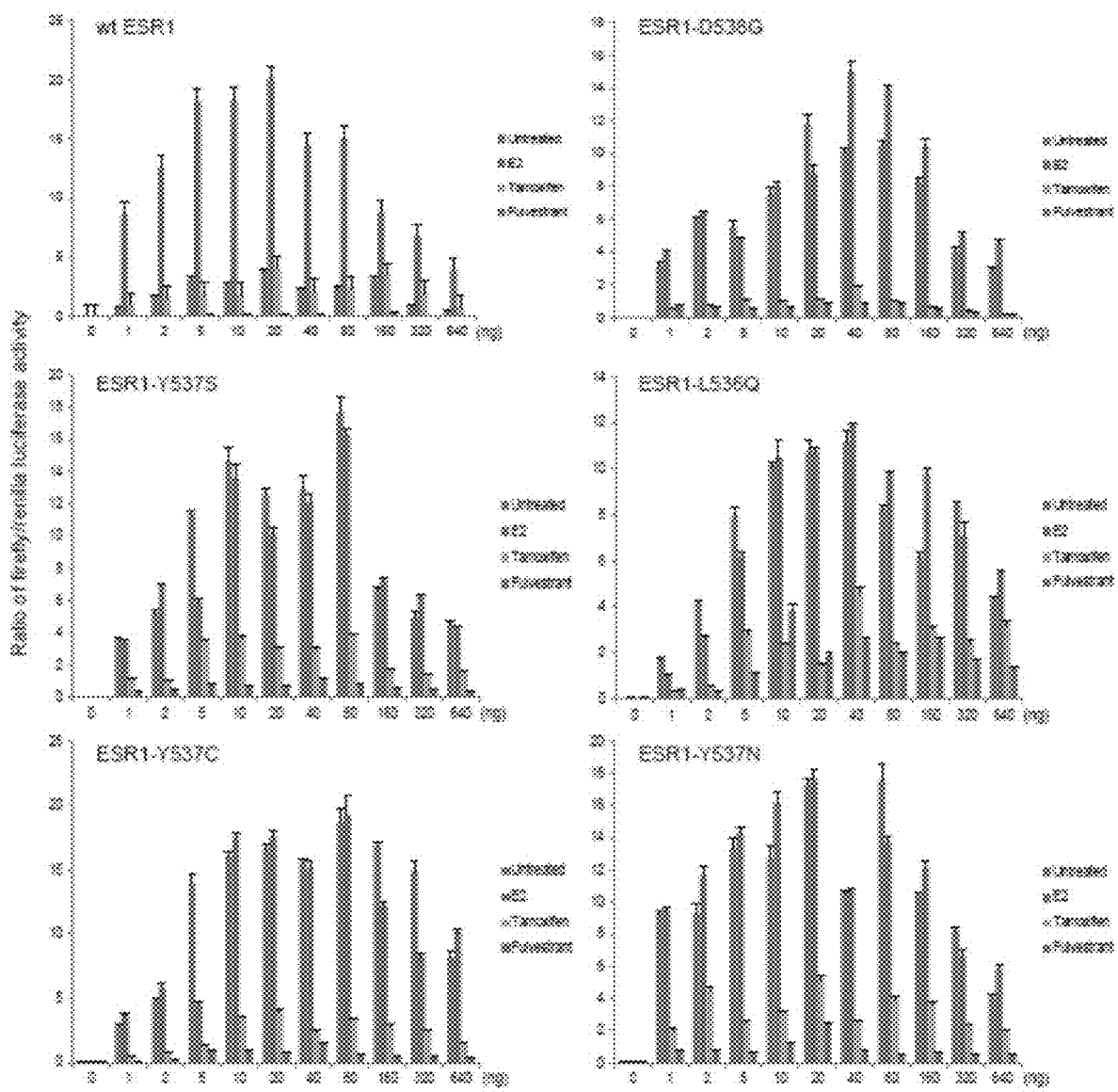
FIG. 7 shows an analysis of transactivational activity of wild type and mutant ESR1 variants by luciferase reporter assay.
Figure 8:
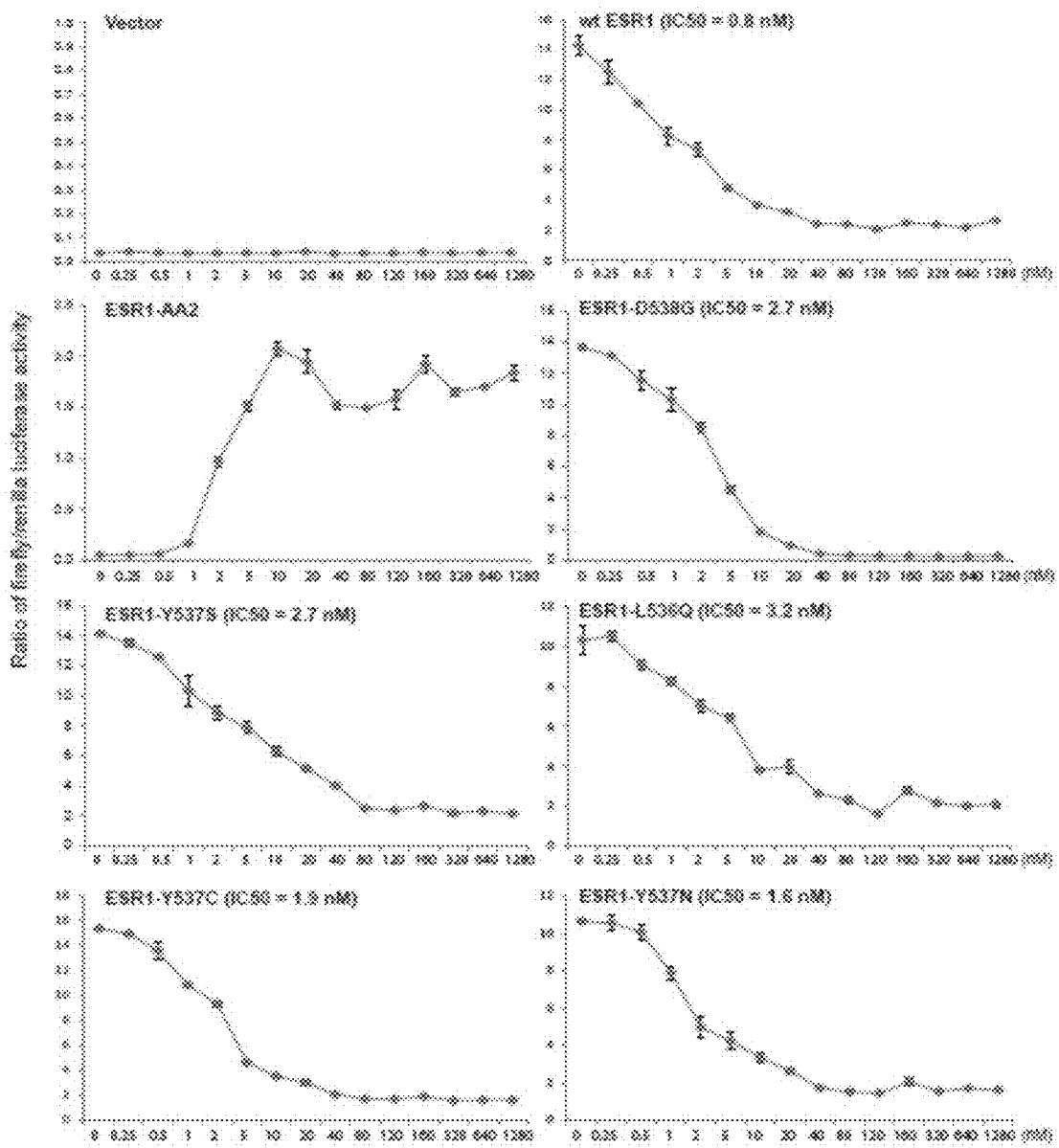
FIG. 8 shows dose response of the wild type and mutant ESR1 variants to 4-hydroxytamoxifen, in competition with 1 nM estradiol.
Figure 9:
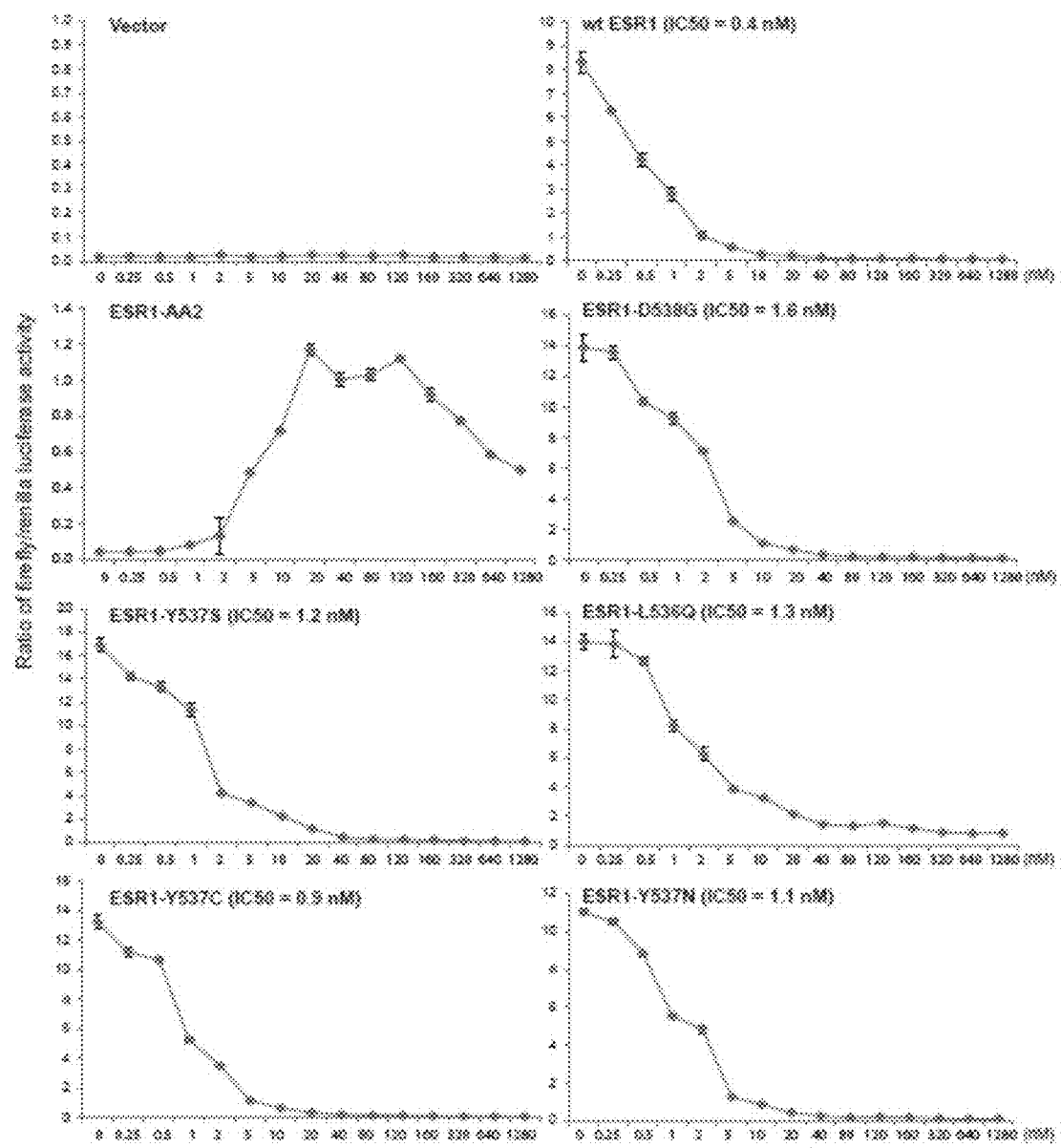
FIG. 9 shows dose response of the wild type and mutant ESR1 variants to fulvestrant, in competition with 1 nM estradiol.
Figure 10:
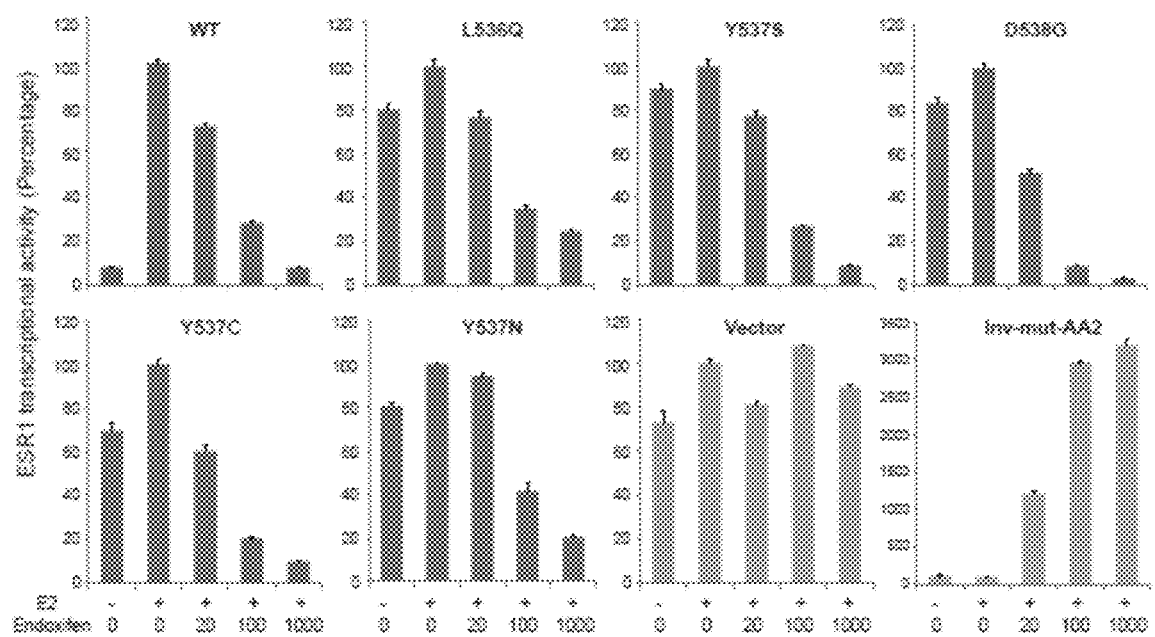
FIG. 10 shows inhibition of transactivation activity of wild type and mutant ESR1 variants by endoxifen.

Next, it was assessed whether anti-estrogen therapies affected the functional activity of these LBD mutations. As inhibition effects can be influenced by level of ectopic estrogen receptor expression, a dose response study of expression plasmid was performed 50 ng was selected for the following experiments (Huang, H. J., et al., Mol Endocrinol 16, 1778-92 (2002)) (FIG. 7). Wild-type ER was inhibited in a dose-dependent fashion by the anti-estrogens 4-hydroxytamoxifen, fulvestrant and endoxifen (FIGS. 4, 8, 9, and 10). In addition, the synthetic ESR1 mutation (Inv-mut-AA2) was activated in a dose-dependent fashion by these anti-estrogens (FIG. 4), which has been reported previously (Feil, et al., *Biochem Biophys Res* Commun 237, 752-7 (1997)). Each of the 5 LBD mutations of ESR1 identified in this study was inhibited by tamoxifen and fulvestrant in a dose-dependent fashion and do not exhibit the inverted response to antiestrogens that the synthetic mutation Inv-mut-AA2 does. It is possible that these mutations did not arise under selective pressure of anti-estrogen treatment, but rather in the context of an estrogen deprivation setting such as treatment with aromatase inhibitors and/or oophorectomy. The IC50s for both 4-hydroxytamoxifen and fulvestrant were 2 to 4 fold higher for all the mutants compared to wild type ESR1. Fulvestrant exhibited greater maximal inhibition than 4-hydroxytamoxifen for all the mutants tested (FIGS. 8 and 9).

The ESR1 mutations identified in this study cluster near the beginning of helix 12 (FIG. 2). Structural studies have demonstrated a key role in the position of helix 12 in the response of the estrogen receptor to agonists and antagonists (Shiau, A. K. et al. *Cell* 95, 927-37 (1998), and p.Tyr537 has been postulated to form a capping motif contributing to activity of the receptor (Skafar, Cell Biochem Biophys 33, 53-62 (2000)). Specifically the p.Tyr537Ser mutant has been reported to have higher affinity for estrogen than wild type and interacts with the SRC1 coactivator in the absence of ligand (Carlson et al., Biochemistry 36, 14897-905 (1997); Weis et al., Mol Endocrinol 10, 1388-98 (1996)). Several studies using experimental mutagenesis have implicated the same three residues identified here as critical determinants of transcriptional activity of the receptor (Carlson et al., supra; Pearce, et al., J Biol Chem 278, 7630-8 (2003); Zhao, C. et al. J Biol Chem 278, 27278-86 (2003)).

Figure 11:
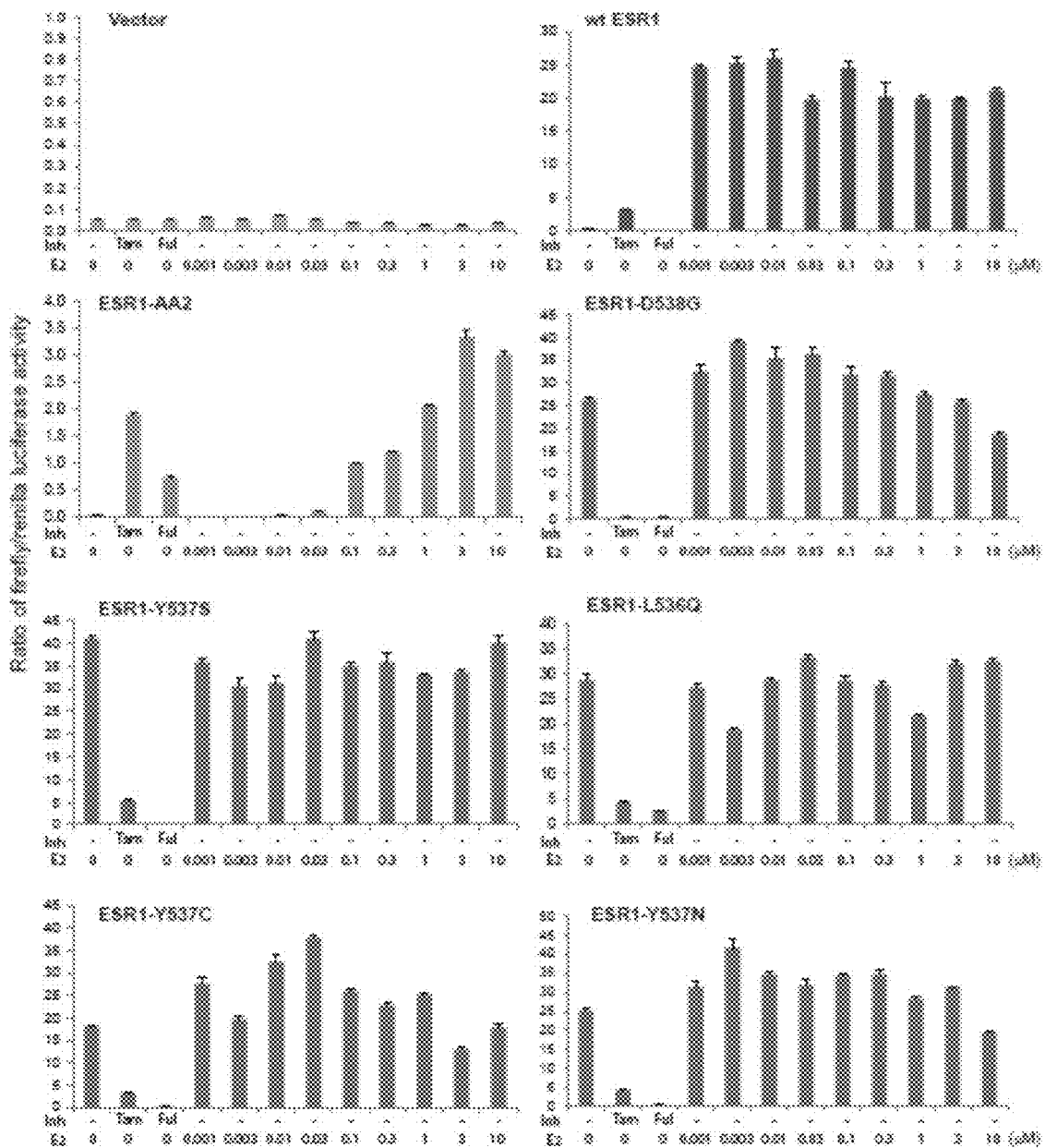
FIG. 11 shows dose response of the wild type and mutant ESR1 variants to estradiol.

As estrogen therapy has been shown to have positive effect in treating aromatase inhibitor resistant advance breast cancers, we tested the effect of low to high dose estrogen on the activity of the mutants in the transient luciferase reporter assay (FIG. 11) (Ellis, M. J. et al. JAMA 302, 774-80 (2009); Swaby, R. F. & Jordan, Clin Breast Cancer 8, 124-33 (2008)). The results do not suggest the effectiveness of this therapy is via directly influencing the transcriptional activity of these mutants, if present in the responding patients.

The experiments described herein revealed either de novo driver mutations and/or potential acquired mutations in breast cancer such as PI3K activation, PAK1 amplification, and FGFR fusion/amplification which have been described earlier (Wu, Y. M. et al. Cancer Discov 3, 636-647 (2013); Kan, Z. et al. *Nature* 466, 869-73 (2010); Shrestha, Y. et al. Oncogene 31, 3397-408 (2012). Focal amplification of MDM2 (a negative regulator of p53 which is targetable) and copy gains of gonadotropin-releasing hormone receptor (GNRHR) were identified.

Since the LBD mutations of ESR1 identified in this study are constitutively active, they can function in the absence of ligand, and maintain ER signaling. In 1997, an LBD mutation of ESR1, p.Tyr537Asn, was detected in a single patient with Stage IV metastatic breast cancer who had been treated with diethylstibesterol—but since then, this mutation has been considered very rare (Barone et al., Clin Cancer Res 16, 2702-8 (2010)). With the advent of widespread aromatase inhibitor therapy, mutation of the ESR1 LBD is likely a common mechanism of resistance that develops in low estrogen states. LBD mutations of ESR1 were detected somatically in four out of 373 cases of endometrial cancers (Kandoth, C. et al. Nature 497, 67-73 (2013)).

This example demonstates that LBD mutations do not develop in the context of anti-estrogen treatment, since the mutated ESR1 variants continue to be responsive to direct ER antagonists such as tamoxifen and fulvestrant. This is consistent with clinical reports showing that patients that develop resistance to aromatase inhibitors still respond to antiestrogen treatment (Ingle, J. N. et al. Fulvestrant in women with advanced breast cancer after progression on prior aromatase inhibitor therapy: North Central Cancer Treatment Group Trial N0032. J Clin Oncol 24, 1052-6 (2006)).

Accession Codes.

Sequence data have been deposited at the dbGAP, which is hosted by the National Center for Biotechnology Information (NCBI), under accession dbGAP phs000602.v1.p1, and CSER Clinical Sequencing Exploratory Research Program for the NIH-NHGRI grant (1UM1HG006508).

TABLE 1

Clinical sequencing of eleven metastatic ER-positive breast cancer cases.

| Case | Age | ER/PR/ERBB2 | Treatments[a] | #SNV/#Fusion | Genetic aberrations[b] |
|---|---|---|---|---|---|
| MO_1031 | 41 | +/+/− | Tamoxifen, Letrozole, Fulvestrant | 266/18 | ESR1 (p.Leu536Gln), gene copy gains of FGFR1, FGFR2, CCND1, and GNRHR |
| MO_1051 | 31 | +/−/− | Oophorectomy, Letrozole, Fulvestrant | 248/5 | ESR1 (p.Tyr537Ser), PIK3CA (p.His1047Arg), TP53 (p.Gly199Glu), FGFR2-AFF3 fusion |
| MO_1069 | 62 | +/+/− | Tamoxifen, Letrozole, Fulvestrant | 74/9 | ESR1 (D538G), ARID2 (p.Glu245*), gene copy losses of TP53, BRCA1, RB1, ARID1A, and SMARCA4 |
| MO_1129 | 44 | +/+/− | Tamoxifen, oophorectomy, Anastrozole, Fulvestrant, Exemestane | 32/3 | ESR1 (p.Tyr537Ser), PIK3CA (p.Glu542Lys), gene copy gains of CCND1 and PAK1 |
| MO_1030 | 78 | +/+/− | Tamoxifen (short), Anastrozole, Fulvestrant | 26/2 | PIK3CA (p.Glu545Ala), TP53 copy loss |
| MO_1068 | 65 | +/−/− | Tamoxifen, Anastrozole | 83/10 | PIK3CA (p.His1047Arg), TP53 (p.Glu51*), MSH2 copy loss |
| MO_1090 | 52 | +/+/− | Tamoxifen, Anastrozole | 28/11 | No significant drivers identified |
| MO_1107 | 46 | +/+/− | Tamoxifen, oophorectomy, Anastrozole, Fulvestrant, Exemestane | 63/12 | BRCA1 (c.5385_5386insC), frameshift deletions in TP53, SMARCA4, and NF1 |
| MO_1167 | 60 | +/−/− | Tamoxifen, Letrozole | 47/3 | ESR1 (p.Asp538Gly) |
| MO_1185 | 58 | +/+/− | Tamoxifen, Letrozole, Fulvestrant, Exemestane | 88/1 | ESR1 (p.Tyr537Ser), CDH1 (p.Gln641*), NOTCH2 (frameshift deletion), TP53 copy loss |
| TP_2004[c] | 52 | +/−/− | Tamoxifen (short) | 29/22 | MDM2 gene amplification, gene copy losses of CDKN2A and CDKN2B |

Notes:
[a]Only anti-estrogen related treatments are listed in table. Patients also received chemotherapies, radiation, or mastectomy in the interim between diagnosis and MI-ONCOSEQ sequencing.
[b]Amino acid substitutions caused by nonsynonymous somatic mutations are marked in parentheses.
[c]TP_2004 is a male patient.

TABLE 2

| Case ID | Lib ID | Library Type | Sample | Read Length | % PF Clusters | PhiX % Error | % > Q30 | # Reads | % Aligned | Gb Aligned |
|---|---|---|---|---|---|---|---|---|---|---|
| MO_1185 | SI_6764 | Transcriptome | Tumor Biopsy-2013 | 2 × 111 | 90.6 | 0.24 | 84.7 | 83957912 | 90.6 | 8.44 |
| MO_1185 | SI_6828 | Exome Capture | Tumor Biopsy-2013 | 2 × 111 | 92.0 | 0.22 | 91.0 | 192597898 | 91.7 | 19.60 |
| MO_1185 | SI_6830 | Exome Capture | Normal Blood-2013 | 2 × 111 | 92.0 | 0.22 | 91.0 | 137187312 | 92.5 | 14.09 |
| MO_1167 | SI_6652 | Transcriptome | Tumor Biopsy-2013 | 2 × 111 | 91.2 | 0.25 | 89.7 | 118377118 | 92.3 | 11.98 |
| MO_1167 | SI_6609 | Exome Capture | Tumor Biopsy-2013 | 2 × 111 | 95.0 | 0.19 | 95.2 | 229166770 | 91.9 | 24.17 |
| MO_1167 | SI_6610 | Exome Capture | Tumor Biopsy-2013 | 2 × 111 | 95.0 | 0.19 | 95.2 | 150585064 | 93.3 | 15.88 |
| MO_1129 | SI_6664 | Transcriptome | Tumor Biopsy-2013 | 2 × 126 | 93.2 | 0.56 | 90.7 | 110783125 | 93.3 | 13.03 |
| MO_1129 | SI_6191 | Exome Capture | Tumor Biopsy-2013 | 2 × 101 | 91.7 | 0.72 | 89.6 | 216483626 | 91.1 | 19.92 |

TABLE 2-continued

| Case ID | Lib ID | Library Type | Sample | Read Length | % PF Clusters | PhiX % Error | % > Q30 | # Reads | % Aligned | Gb Aligned |
|---|---|---|---|---|---|---|---|---|---|---|
| MO_1129 | SI_6192 | Exome Capture | Normal Blood-2013 | 2 × 101 | 91.7 | 0.72 | 89.6 | 135084370 | 91.6 | 12.50 |
| MO_1129 | SI_6580 | Exome Capture | Tumor FFPE-2001 | 2 × 111 | 92.4 | 0.58 | 90.2 | 113985464 | 94.4 | 11.95 |
| MO_1069 | SI_5257 | Transcriptome | Tumor Biopsy-2012 | 2 × 101 | 92.5 | 0.63 | 86.3 | 108932482 | 91.2 | 10.03 |
| MO_1069 | SI_5259 | Exome Capture | Tumor Biopsy-2012 | 2 × 101 | 93.5 | 0.54 | 88.7 | 228128358 | 92.1 | 21.22 |
| MO_1069 | SI_5260 | Exome Capture | Normal Blood-2012 | 2 × 101 | 93.5 | 0.54 | 88.7 | 143597568 | 93.0 | 13.49 |
| MO_1069 | SI_6666 | Exome Capture | Tumor FFPE-1994 | 2 × 126 | 93.2 | 0.56 | 90.7 | 115997626 | 96.2 | 11.28 |
| MO_1051 | SI_5091 | Transcriptome | Tumor Biopsy-2012 | 2 × 101 | 89.2 | 0.67 | 87.4 | 102882633 | 91.2 | 9.47 |
| MO_1051 | SI_5121 | Exome Capture | Tumor Biopsy-2012 | 2 × 101 | 92.3 | 0.86 | 87.4 | 209297646 | 92.1 | 19.47 |
| MO_1051 | SI_5080 | Exome Capture | Normal Blood-2012 | 2 × 101 | 90.0 | 0.69 | 88.4 | 193338100 | 89.0 | 17.38 |
| MO_1051 | SI_5447 | Exome Capture | Tumor FFPE-2005 | 2 × 101 | 93.3 | 1.04 | 83.3 | 176710228 | 89.2 | 15.91 |
| MO_1031 | SI_5256 | Transcriptome | Tumor Biopsy-2012 | 2 × 101 | 91.8 | 0.61 | 84.7 | 101227958 | 92.4 | 9.45 |
| MO_1031 | SI_5261 | Exome Capture | Tumor Biopsy-2012 | 2 × 101 | 93.7 | 0.67 | 86.8 | 150236180 | 91.4 | 13.87 |
| MO_1031 | SI_5262 | Exome Capture | Normal Blood-2012 | 2 × 101 | 93.7 | 0.67 | 86.8 | 221415120 | 91.6 | 20.48 |

TABLE 3

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1031 | HLA-A | p.A182V | 6 | 29911246 | C | T | NA | 323.8 | 0 | 0.08 |
| MO_1031 | ESR1 | p.L536Q | 6 | 152419920-1 | TC | AG | NA | 55.5 | 0 | 0 |
| MO_1031 | GPS2 | p.Q226X | 17 | 7216747 | G | A | NA | 52.7 | 0 | 0 |
| MO_1031 | PATZ1 | p.R214W | 22 | 31740949 | G | A | NA | 42.1 | 0 | 0 |
| MO_1031 | MTOR | p.F319L | 1 | 11308035 | G | C | NA | 15.6 | 0 | 0.65 |
| MO_1031 | RNF43 | p.E712Q | 17 | 56434880 | C | G | NA | 14.8 | 0 | 0 |
| MO_1031 | CRKL | p.S112C | 22 | 21288090 | C | G | NA | 11.4 | 0 | 0.02 |
| MO_1031 | BIRC2 | p.K102N | 11 | 102220891 | G | C | NA | 11.4 | 0 | 0.02 |
| MO_1031 | AKAP9 | p.S403F | 7 | 91630403 | C | T | NA | 10.3 | 0 | 0 |
| MO_1031 | AKAP9 | p.P1393S | 7 | 91652316 | C | T | NA | 10.3 | 0 | 0.51 |
| MO_1031 | PSIP1 | p.Q384X | 9 | 15469011 | G | A | NA | 10.1 | 0 | 0 |
| MO_1031 | GPR124 | p.A394V | 8 | 37690611 | C | T | NA | 8.7 | 0 | 0.36 |
| MO_1031 | KDM5A | p.R1121T | 12 | 418985 | C | G | NA | 7.2 | 0 | 0.01 |
| MO_1031 | NCOA1 | p.S1320C | 2 | 24980919 | C | G | NA | 4.9 | 0 | 0 |
| MO_1031 | ARID2 | p.E1315K | 12 | 46245849 | G | A | NA | 3.1 | 0 | 0.01 |
| MO_1031 | BRIP1 | p.M1970I | 17 | 59763192 | C | T | NA | 2.0 | 0 | 0 |
| MO_1031 | ASXL2 | p.E1178Q | 2 | 25965674 | C | G | NA | 1.7 | 0 | 0.02 |
| MO_1031 | APC | p.D1558N | 5 | 112175953 | G | A | NA | 1.1 | 0 | 0.09 |
| MO_1031 | FAM123B | p.Q1098X | X | 63409875 | G | A | NA | 0.6 | 0 | 0.31 |
| MO_1031 | BLK | p.M164I | 8 | 11414186 | G | A | NA | 0.1 | 0 | 0.11 |
| MO_1031 | IRS4 | p.S49F | X | 107979429 | G | A | NA | 0.0 | 0 | 0 |
| MO_1031 | FN1 | p.R1162T | 2 | 216262435 | C | G | NA | 901.7 | 0 | 0.01 |
| MO_1031 | KIAA0913 | p.R944L | 10 | 75554320 | G | T | NA | 400.5 | 0 | 0.06 |
| MO_1031 | DLG5 | p.R1685C | 10 | 79565534 | G | A | NA | 376.4 | 1 | 0 |
| MO_1031 | FLNA | p.R1951W | X | 153581931 | G | A | NA | 276.3 | 0 | 0 |
| MO_1031 | ERI3 | p.V7L | 1 | 44788522 | C | G | NA | 231.6 | 0 | 0 |
| MO_1031 | NUDT5 | p.S199C | 10 | 12209765 | G | C | NA | 215.4 | 0 | 0.05 |
| MO_1031 | CLTC | p.E33Q | 17 | 57721691 | G | C | NA | 182.2 | 0 | 0.03 |
| MO_1031 | ANXA7 | p.S301X | 10 | 75143015 | G | C | NA | 166.1 | 0 | 0.38 |
| MO_1031 | C14orf166 | p.R65K | 14 | 52460448 | G | A | NA | 156.3 | 0 | 1 |
| MO_1031 | MRPL38 | p.S263C | 17 | 73895678 | G | C | NA | 148.7 | 0 | 0.02 |
| MO_1031 | IGLV2-23 | p.A27V | 22 | 23040632 | C | T | NA | 141.3 | 0 | 0.01 |
| MO_1031 | SCRIB | p.E686K | 8 | 144890838 | C | T | NA | 107.1 | 0 | 0.23 |
| MO_1031 | S100A13 | p.L71F | 1 | 153591457 | G | A | NA | 101.3 | 0 | 0 |
| MO_1031 | CTSZ | p.D72H | 20 | 57581470 | C | G | NA | 82.9 | 0 | 0.01 |
| MO_1031 | RAB11FIP1 | p.E931K | 8 | 37729529 | C | T | NA | 80.2 | 0 | 0 |
| MO_1031 | DLGAP4 | p.S225C | 20 | 35060794 | C | G | NA | 71.7 | 0 | 0.01 |
| MO_1031 | FAAH | p.R260C | 1 | 46871459 | C | T | NA | 60.6 | 0 | 0 |
| MO_1031 | RBM6 | p.M10871 | 3 | 50114455 | G | A | NA | 60.4 | 0 | 0.06 |
| MO_1031 | DHTKD1 | p.V298M | 10 | 12131159 | G | A | NA | 57.1 | 0 | 0.63 |
| MO_1031 | PARP12 | p.R242T | 7 | 139756691 | C | G | NA | 56.9 | 0 | 0.27 |
| MO_1031 | MAN2A2 | p.I71M | 15 | 91448561 | G | C | NA | 55.4 | 0 | 0 |
| MO_1031 | MAEA | p.E27D | 4 | 1305778 | G | C | NA | 53.2 | 0 | 0 |
| MO_1031 | USP34 | p.E2101Q | 2 | 61475739 | C | G | NA | 52.4 | 0 | 0 |
| MO_1031 | TTC17 | p.E329Q | 11 | 43419590 | G | C | NA | 51.8 | 0 | 0.05 |
| MO_1031 | MUC19 | p.H954D | 12 | 40836890 | C | G | NA | 49.1 | 0 | 0.63 |
| MO_1031 | PSMC2 | p.E185K | 7 | 103003848 | G | A | NA | 48.1 | 0 | 0.57 |
| MO_1031 | POR | p.R554Q | 7 | 75615159 | G | A | NA | 44.8 | 0 | 0.09 |
| MO_1031 | CNKSR1 | p.A534G | 1 | 26515099 | C | G | NA | 44.6 | 0 | 0.25 |
| MO_1031 | MAPKAP1 | p.R467T | 9 | 128201227 | C | G | NA | 43.4 | 0 | 0 |
| MO_1031 | ADAM9 | p.S38L | 8 | 38865420 | C | T | NA | 41.8 | 0 | 0.13 |
| MO_1031 | CTNNBL1 | p.D274N | 20 | 36405816 | G | A | NA | 41.7 | 0 | 0.34 |
| MO_1031 | VPS16 | p.E614Q | 20 | 2845214 | G | C | NA | 39.9 | 0 | 0.22 |
| MO_1031 | VPS16 | p.E684K | 20 | 2845839 | G | A | NA | 39.9 | 0 | 0.01 |
| MO_1031 | RTKN | p.G314S | 2 | 74655775 | C | T | NA | 39.7 | 0 | 0 |

TABLE 3-continued

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1031 | SFSWAP | p.E523Q | 12 | 132241036 | G | C | NA | 38.8 | 0 | 0.16 |
| MO_1031 | LONP1 | p.I700M | 19 | 5694826 | G | C | NA | 38.6 | 0 | 0.05 |
| MO_1031 | FNBP4 | p.K938N | 11 | 47741630 | C | G | NA | 38.2 | 0 | 0.02 |
| MO_1031 | UPF3A | p.S50F | 13 | 115047263 | C | T | NA | 33.4 | 0 | 0.06 |
| MO_1031 | PTPN12 | p.I316T | 7 | 77247804 | T | C | NA | 33.3 | 0 | 0.39 |
| MO_1031 | CUX1 | p.E1492K | 7 | 101892278 | G | A | NA | 27.3 | 0 | 0 |
| MO_1031 | NOL11 | p.C144S | 17 | 65717611 | G | A | NA | 27.1 | 0 | 0.07 |
| MO_1031 | CYP27A1 | p.S280F | 2 | 219677467 | C | T | NA | 27.1 | 0 | 0.02 |
| MO_1031 | ATP6V1B1 | p.Q244H | 2 | 71188770 | G | C | NA | 25.5 | 0 | 0 |
| MO_1031 | GMPR2 | p.E204K | 14 | 24706513 | G | A | NA | 24.4 | 0 | 0 |
| MO_1031 | SPTAN1 | p.Q1980K | 9 | 131386727 | C | A | NA | 24.0 | 0 | 0 |
| MO_1031 | SPTAN1 | p.S2138C | 9 | 131388818 | C | G | NA | 24.0 | 0 | 0 |
| MO_1031 | IVNS1ABP | p.D77N | 1 | 185278187 | C | T | NA | 23.9 | 0 | 0.32 |
| MO_1031 | LRP1 | p.E270K | 12 | 57539240 | G | A | NA | 23.6 | 0 | 0.13 |
| MO_1031 | TMEM129 | p.S105Y | 4 | 1720245 | G | T | NA | 23.4 | 0 | 0.03 |
| MO_1031 | FARP1 | p.D153N | 13 | 99030133 | G | A | NA | 22.2 | 0 | 0.02 |
| MO_1031 | KRT10 | p.E169K | 17 | 38978333 | C | T | NA | 22.2 | 0 | 0.25 |
| MO_1031 | SLC27A4 | p.D127N | 9 | 131107651 | G | A | NA | 21.1 | 0 | 0.08 |
| MO_1031 | HDAC11 | p.P13S | 3 | 13522251 | C | T | NA | 20.2 | 0 | 0 |
| MO_1031 | FAM193A | p.K878E | 4 | 2698318 | A | G | NA | 19.8 | 0 | 0 |
| MO_1031 | FAM100B | p.S83C | 17 | 74266339 | C | G | NA | 19.3 | 0 | 0 |
| MO_1031 | STAU2 | p.M429I | 8 | 74439971 | C | G | NA | 18.9 | 0 | |
| MO_1031 | FAM84B | p.Q129R | 8 | 127569249 | T | C | NA | 18.6 | 0 | 0.34 |
| MO_1031 | SIN3A | p.S689C | 15 | 75688626 | G | C | NA | 18.4 | 0 | 0.03 |
| MO_1031 | NRP1 | p.I121M | 10 | 33559670 | G | C | NA | 17.6 | 0 | 0 |
| MO_1031 | PDCD7 | p.L3V | 15 | 65426113 | G | C | NA | 16.4 | 0 | 0 |
| MO_1031 | FRMD8 | p.E462K | 11 | 65178820 | G | A | NA | 16.2 | 0 | 0 |
| MO_1031 | SDCCAG8 | p.G44A | 1 | 243433470 | G | C | NA | 16.1 | 0 | 0.36 |
| MO_1031 | MBD5 | p.Q987X | 2 | 149241119 | C | T | NA | 15.6 | 0 | 0 |
| MO_1031 | RALGAPB | p.D79H | 20 | 37121621 | G | C | NA | 15.6 | 0 | 0 |
| MO_1031 | CAND1 | p.E870X | 12 | 67700058 | G | T | NA | 15.1 | 0 | 0 |
| MO_1031 | CEP250 | p.L682V | 20 | 34065878 | C | G | NA | 14.9 | 0 | 0 |
| MO_1031 | HSD17B8 | p.E243K | 6 | 33174184 | G | A | NA | 14.6 | 0 | 0.01 |
| MO_1031 | BAZ1A | p.E1246Q | 14 | 35233953 | C | G | NA | 14.6 | 0 | 0.3 |
| MO_1031 | PUM1 | p.E249K | 1 | 31468043 | C | T | NA | 14.6 | 0 | 0.09 |
| MO_1031 | RILPL1 | p.M134I | 12 | 124008100 | C | A | NA | 14.0 | 0 | 0.31 |
| MO_1031 | LACTB2 | p.E65K | 8 | 71574062 | C | T | NA | 13.8 | 0 | 0.16 |
| MO_1031 | LRIG1 | p.T717M | 3 | 66433747 | G | A | NA | 13.0 | 0 | 0.02 |
| MO_1031 | RNF6 | p.E266K | 13 | 26789223 | C | T | NA | 12.8 | 0 | 0.03 |
| MO_1031 | DDX58 | p.R6Q | 9 | 32526148 | C | T | NA | 12.7 | 0 | 0.02 |
| MO_1031 | UNKL | p.E312D | 16 | 1444133 | C | G | NA | 12.6 | 0 | 0.08 |
| MO_1031 | UNKL | p.S246X | 16 | 1448940 | C | T | NA | 12.6 | 0 | 0 |
| MO_1031 | LRBA | p.L2000V | 4 | 151520207 | G | C | NA | 12.4 | 0 | 0.14 |
| MO_1031 | LRBA | p.F1979L | 4 | 151520268 | C | G | NA | 12.4 | 0 | 0.01 |
| MO_1031 | HEATR5A | p.L429F | 14 | 31855668 | G | A | NA | 12.4 | 0 | 0 |
| MO_1031 | PRR12 | p.L1355V | 19 | 50102913 | C | G | NA | 12.1 | 0 | 0.14 |
| MO_1031 | UGGT1 | p.I782M | 2 | 128914911 | C | G | NA | 12.0 | 0 | 0.02 |
| MO_1031 | SLC10A3 | p.Q441E | X | 153715959 | G | C | NA | 12.0 | 0 | 0.42 |
| MO_1031 | PDLIM2 | p.R243W | 8 | 22447218 | C | T | NA | 11.8 | 0 | 0 |
| MO_1031 | PVRL4 | p.D338H | 1 | 161044152 | C | G | NA | 11.4 | 0 | 0.05 |
| MO_1031 | ZNHIT2 | p.E111Q | 11 | 64884795 | C | G | NA | 11.3 | 0 | 0.22 |
| MO_1031 | CMAHP | p.L152F | 6 | 25109797 | G | A | NA | 11.0 | 0 | 0.02 |
| MO_1031 | CNIH2 | p.E114K | 11 | 66050747 | G | A | NA | 10.5 | 0 | 0.02 |
| MO_1031 | CTAGE5 | p.S661C | 14 | 39816944 | C | G | NA | 10.5 | 0 | 0 |
| MO_1031 | MMP19 | p.S430L | 12 | 56231058 | G | A | NA | 10.3 | 0 | 0.01 |
| MO_1031 | MREG | p.R165K | 2 | 216810310 | C | T | NA | 9.8 | 0 | 0 |
| MO_1031 | SLCO2A1 | splice acc. | 3 | 133692670 | C | G | NA | 9.6 | 0 | |
| MO_1031 | C7orf13 | p.A36P | 7 | 156433243 | C | G | NA | 9.5 | 0 | |
| MO_1031 | NUP160 | p.D449Y | 11 | 47840943 | C | A | NA | 8.6 | 0 | 0.02 |
| MO_1031 | PNPLA7 | p.S555C | 9 | 140395161 | G | C | NA | 8.5 | 0 | 0 |
| MO_1031 | GCDH | p.P51R | 19 | 13003198 | C | G | NA | 8.5 | 0 | 0.32 |
| MO_1031 | RNF115 | p.E238K | 1 | 145687020 | G | A | NA | 8.3 | 0 | 0.1 |
| MO_1031 | MFSD11 | p.R304C | 17 | 74771114 | C | T | NA | 8.1 | 0 | 0 |
| MO_1031 | BZRAP1 | p.K1347N | 17 | 56386592 | C | A | NA | 8.0 | 0 | 0 |
| MO_1031 | SNX27 | p.D283H | 1 | 151634687 | G | C | NA | 7.8 | 0 | 0 |
| MO_1031 | ZBTB42 | p.M1I | 14 | 105267537 | G | A | NA | 7.8 | 0 | 0 |
| MO_1031 | ZBTB42 | p.E2K | 14 | 105267538 | G | A | NA | 7.8 | 0 | 0.01 |
| MO_1031 | ZBTB42 | p.E96K | 14 | 105267820 | G | A | NA | 7.8 | 0 | 0 |
| MO_1031 | TTF1 | p.K17N | 9 | 135278158 | C | A | NA | 7.5 | 0 | 0 |
| MO_1031 | TMEM106B | p.T234R | 7 | 12271477 | C | G | NA | 7.4 | 0 | 0.24 |
| MO_1031 | SMARCC1 | p.D284N | 3 | 47752241 | C | T | NA | 7.3 | 0 | 0 |
| MO_1031 | INTS6 | p.I3M | 13 | 52026653 | G | C | NA | 7.3 | 0 | 0 |
| MO_1031 | AC008073.6.1 | p.Q107X | 2 | 24360929 | C | T | NA | 7.0 | 0 | 0.24 |
| MO_1031 | ZNF791 | p.R544T | 19 | 12739974 | G | C | NA | 6.8 | 0 | 0 |
| MO_1031 | SMG1 | p.Q1779E | 16 | 18861397 | G | C | NA | 6.7 | 0 | 0.96 |
| MO_1031 | INTS2 | p.E759K | 17 | 59958371 | C | T | NA | 6.5 | 0 | 0.26 |
| MO_1031 | LRRC1 | p.L314F | 6 | 53769212 | G | C | NA | 6.5 | 0 | 0 |

TABLE 3-continued

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1031 | CEP76 | p.C612Y | 18 | 12674541 | C | T | NA | 6.1 | 0 | |
| MO_1031 | ZCCHC2 | p.R214Q | 18 | 60191298 | G | A | NA | 6.1 | 0 | 0 |
| MO_1031 | SPICE1 | p.L521V | 3 | 113176079 | G | C | NA | 6.0 | 0 | 0.18 |
| MO_1031 | LY86 | p.I78M | 6 | 6626536 | C | G | NA | 6.0 | 0 | 0.23 |
| MO_1031 | CACNB1 | p.G169C | 17 | 37343092 | G | A | NA | 6.0 | 0 | 0 |
| MO_1031 | ARHGAP29 | p.E185K | 1 | 94671197 | C | T | NA | 6.0 | 0 | 0.06 |
| MO_1031 | RND1 | p.S230Y | 12 | 49251789 | G | T | NA | 5.7 | 0 | 0 |
| MO_1031 | ZCCHC3 | p.E221K | 20 | 278888 | G | A | NA | 5.6 | 0 | 0.03 |
| MO_1031 | SMOX | p.S84C | 20 | 4158040 | C | G | NA | 5.5 | 0 | 0 |
| MO_1031 | LENG9 | p.E196Q | 19 | 54974190 | C | G | NA | 5.4 | 0 | 0.23 |
| MO_1031 | ZBTB1 | p.M653I | 14 | 64990181 | G | A | NA | 5.0 | 0 | 0.03 |
| MO_1031 | OBSCN | p.Q1409X | 1 | 228492156 | C | T | NA | 4.9 | 0 | 0.19 |
| MO_1031 | ZNF564 | p.L237F | 19 | 12638213 | G | A | NA | 4.8 | 0 | 0.7 |
| MO_1031 | PAFAH2 | p.F276L | 1 | 26301066 | G | C | NA | 4.6 | 0 | 0.47 |
| MO_1031 | GBP4 | p.M542I | 1 | 89652097 | C | T | NA | 4.6 | 0 | 0.94 |
| MO_1031 | ELMO1 | p.G559E | 7 | 36927203 | C | T | NA | 4.5 | 0 | 0 |
| MO_1031 | RPGR | p.E512K | X | 38150250 | C | T | NA | 4.5 | 0 | 0.01 |
| MO_1031 | RAPH1 | p.P1077T | 2 | 204304684 | G | T | NA | 4.5 | 0 | 0 |
| MO_1031 | RGL4 | p.R441Q | 22 | 24040460 | G | A | NA | 4.5 | 0 | 0.58 |
| MO_1031 | RNF32 | p.K94N | 7 | 156447277 | G | C | NA | 4.3 | 0 | 0 |
| MO_1031 | KMO | p.S171L | 1 | 241725529 | C | T | NA | 4.2 | 0 | 0 |
| MO_1031 | TMOD3 | p.S127Y | 15 | 52179882 | C | A | NA | 4.0 | 0 | 0 |
| MO_1031 | MEX3A | p.G459S | 1 | 156046553 | C | T | NA | 4.0 | 0 | |
| MO_1031 | KIF21A | p.S1258L | 12 | 39711971 | G | A | NA | 3.8 | 0 | 0 |
| MO_1031 | FAM179B | p.H1193D | 14 | 45497451 | C | G | NA | 3.7 | 0 | 1 |
| MO_1031 | DOCK10 | p.D744H | 2 | 225714229 | C | G | NA | 3.7 | 0 | 0 |
| MO_1031 | FMNL2 | p.K217T | 2 | 153431703 | A | C | NA | 3.4 | 0 | 0.03 |
| MO_1031 | FUT2 | p.S52X | 19 | 49206368 | C | G | NA | 3.3 | 0 | 0.01 |
| MO_1031 | ZCCHC14 | p.L526P | 16 | 87446339 | A | G | NA | 3.3 | 0 | 0 |
| MO_1031 | ZSWIM4 | p.E232D | 19 | 13915946 | G | C | NA | 3.2 | 0 | 0.02 |
| MO_1031 | PCLR2M | p.T126P | 15 | 58001174 | A | C | NA | 3.2 | 0 | 0.01 |
| MO_1031 | DET1 | p.S169L | 15 | 89074464 | G | A | NA | 3.1 | 1 | 0 |
| MO_1031 | SLC35D1 | p.F145S | 1 | 67516146 | A | G | NA | 2.9 | 0 | 0.01 |
| MO_1031 | CHIC1 | p.X218S | X | 72900839 | G | C | NA | 2.9 | 0 | 0.86 |
| MO_1031 | SEMA3E | p.E764Q | 7 | 82996940 | C | G | NA | 2.9 | 0 | 0.02 |
| MO_1031 | ATG2B | p.K11N | 14 | 96829281 | C | G | NA | 2.8 | 1 | 0.04 |
| MO_1031 | FAT3 | p.E2994X | 11 | 92538402 | G | T | NA | 2.3 | 0 | 0.17 |
| MO_1031 | POPDC2 | p.I154M | 3 | 19378809 | G | C | NA | 2.3 | 0 | 0 |
| MO_1031 | SLIT3 | p.T958S | 5 | 168127656 | G | C | NA | 2.2 | 0 | 0.23 |
| MO_1031 | SYNPO2 | p.R1088H | 4 | 119978566 | G | A | NA | 2.2 | 0 | 0.26 |
| MO_1031 | VCPIP1 | p.S545C | 8 | 67577560 | G | C | NA | 2.1 | 0 | 0.02 |
| MO_1031 | FAM184B | p.E73K | 4 | 17711192 | C | T | NA | 2.1 | 0 | 0.01 |
| MO_1031 | RASA2 | p.S323L | 3 | 141289858 | C | T | NA | 2.0 | 0 | 0.2 |
| MO_1031 | C3orf67 | p.S326L | 3 | 58849525 | G | A | NA | 2.0 | 0 | 0.14 |
| MO_1031 | C1orf167 | p.Q1046E | 1 | 11844289 | C | G | NA | 2.0 | 0 | 0 |
| MO_1031 | ANKS1B | p.G573E | 12 | 99793447 | C | T | NA | 1.9 | 0 | 0.17 |
| MO_1031 | ZNF837 | p.S376L | 19 | 58879573 | G | A | NA | 1.8 | 0 | 0 |
| MO_1031 | NCOA7 | p.E628K | 6 | 126211082 | G | A | NA | 1.8 | 0 | 0 |
| MO_1031 | STXBP5 | p.S973L | 6 | 147685247 | C | T | NA | 1.8 | 0 | 0 |
| MO_1031 | BCO2 | p.N134Y | 11 | 112064303 | A | T | NA | 1.6 | 0 | 0.02 |
| MO_1031 | CRLF3 | p.I389L | 17 | 29111369 | G | A | NA | 1.6 | 0 | |
| MO_1031 | TM6SF2 | p.F148L | 19 | 19380536 | G | T | NA | 1.5 | 0 | 0.89 |
| MO_1031 | ALPK3 | p.E1722Q | 15 | 85407731 | G | C | NA | 1.2 | 0 | 0 |
| MO_1031 | ZNF717 | p.A312S | 3 | 75787840 | C | A | NA | 1.1 | 0 | 0.32 |
| MO_1031 | ZNF717 | p.V286I | 3 | 75787918 | C | T | NA | 1.1 | 0 | 0.21 |
| MO_1031 | ZNF717 | p.Y283C | 3 | 75787926 | T | C | NA | 1.1 | 0 | 0.01 |
| MO_1031 | TTLL7 | p.S287L | 1 | 84385422 | G | A | NA | 1.1 | 0 | 0.07 |
| MO_1031 | TET3 | p.E913K | 2 | 74320668 | G | A | NA | 1.1 | 0 | 0.11 |
| MO_1031 | ACACB | p.I1273F | 12 | 109661644 | A | T | NA | 1.0 | 0 | 0 |
| MO_1031 | ADAMTSL3 | p.G1502E | 15 | 84694037 | G | A | NA | 0.8 | 0 | 0 |
| MO_1031 | FAM161A | p.E114Q | 2 | 62069339 | C | G | NA | 0.8 | 0 | 0 |
| MO_1031 | RGS9 | p.D65E | 17 | 63154453 | C | G | NA | 0.8 | 0 | 0.03 |
| MO_1031 | SCML1 | p.S188F | X | 17768273 | C | T | NA | 0.7 | 0 | 0.01 |
| MO_1031 | CSF2RB | p.P343S | 22 | 37328821 | C | T | NA | 0.6 | 0 | 0 |
| MO_1031 | CYP7B1 | p.S293F | 8 | 65527762 | G | A | NA | 0.5 | 0 | 0 |
| MO_1031 | BTBD11 | p.Q163H | 12 | 107713206 | G | C | NA | 0.5 | 0 | 0.19 |
| MO_1031 | CCT6B | splice donor | 17 | 33269814 | C | T | NA | 0.5 | 0 | |
| MO_1031 | PRDM5 | p.E108K | 4 | 121760408 | C | T | NA | 0.4 | 10 | 0 |
| MO_1031 | MYO15A | p.E3242Q | 17 | 18067089 | G | C | NA | 0.4 | 0 | 0.05 |
| MO_1031 | TAOK1 | p.S826Y | 17 | 27869955 | C | A | NA | 0.4 | 0 | 0 |
| MO_1031 | COL28A1 | p.I779M | 7 | 7415114 | G | C | NA | 0.4 | 0 | 0 |
| MO_1031 | FREM2 | p.O2473K | 13 | 39433625 | C | A | NA | 0.4 | 0 | 0.3 |
| MO_1031 | GABRA3 | p.N406I | X | 151336962 | T | A | NA | 0.3 | 0 | 0.01 |
| MO_1031 | RUFY4 | p.R422K | 2 | 218940420 | G | A | NA | 0.3 | 0 | 0.42 |
| MO_1031 | RP11-8F2.7.1 | p.E87Q | 3 | 156570767 | G | C | NA | 0.3 | 0 | 0.25 |
| MO_1031 | ICAM5 | p.S70L | 19 | 10401874 | C | T | NA | 0.3 | 0 | 0.67 |
| MO_1031 | LCTL | p.S111Y | 15 | 66856287 | G | T | NA | 0.3 | 0 | 0 |

TABLE 3-continued

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1031 | TMEM151A | p.E257K | 11 | 66062486 | G | A | NA | 0.3 | 0 | 0 |
| MO_1031 | RYR1 | p.S1172L | 19 | 38959739 | C | T | NA | 0.2 | 0 | 0.41 |
| MO_1031 | MACC1 | p.Q488E | 7 | 20193522 | G | C | NA | 0.2 | 0 | 0 |
| MO_1031 | ARPP21 | p.S804R | 3 | 35835423 | C | G | NA | 0.2 | 0 | 0.04 |
| MO_1031 | CCIN | p.M409I | 9 | 36170726 | G | A | NA | 0.2 | 0 | 0 |
| MO_1031 | MUC16 | p.S5280L | 19 | 9071607 | G | A | NA | 0.2 | 0 | 0.02 |
| MO_1031 | C11orf41 | p.T465I | 11 | 33565394 | C | T | NA | 0.1 | 0 | 0.32 |
| MO_1031 | SAMD13 | p.L92F | 1 | 84815382 | G | C | NA | 0.1 | 0 | 0 |
| MO_1031 | GLT1D1 | p.E42Q | 12 | 129360514 | G | C | NA | 0.1 | 0 | 0.05 |
| MO_1031 | PKD1L1 | p.S2552T | 7 | 47849102 | C | G | NA | 0.1 | 0 | 0.15 |
| MO_1031 | C6 | p.Q111K | 5 | 41199984 | G | T | NA | 0.1 | 0 | 0 |
| MO_1031 | BCL2L14 | p.S92C | 12 | 12232514 | C | G | NA | 0.1 | 0 | 0 |
| MO_1031 | RYR2 | p.L192M | 1 | 237540733 | T | A | NA | 0.1 | 0 | 0 |
| MO_1031 | NPAS3 | p.L831I | 14 | 34270100 | C | A | NA | 0.1 | 3 | 0.09 |
| MO_1031 | UGT8 | p.D345E | 4 | 115586905 | C | G | NA | 0.1 | 0 | 0 |
| MO_1031 | IGFN1 | p.D1266H | 1 | 201177817 | G | C | NA | 0.1 | 0 | |
| MO_1031 | NCR3LG1 | p.E23X | 11 | 17373583 | G | T | NA | 0.1 | 0 | 0.6 |
| MO_1031 | GGT2 | splice donor | 22 | 21581683 | A | G | NA | 0.1 | 0 | |
| MO_1031 | SPANXN3 | p.D90H | X | 142596802 | C | G | NA | 0.1 | 0 | 0.01 |
| MO_1031 | CACNA1A | p.D1411N | 19 | 13372295 | C | T | NA | 0.1 | 0 | 0 |
| MO_1031 | UNC79 | p.S1899X | 14 | 94097168 | C | A | NA | 0.1 | 0 | 0 |
| MO_1031 | APOB | p.E3545K | 2 | 21229107 | C | T | NA | 0.1 | 0 | 0.07 |
| MO_1031 | CECR2 | p.S1005W | 22 | 18028057 | C | G | NA | 0.1 | 0 | 0.02 |
| MO_1031 | CACNA1F | p.R402Q | X | 49083503 | C | T | NA | 0.0 | 0 | 0.01 |
| MO_1031 | DUSP27 | p.R551K | 1 | 167096020 | G | A | NA | 0.0 | 1 | 0 |
| MO_1031 | ZNF831 | p.P659L | 20 | 57768050 | C | T | NA | 0.0 | 0 | 0.01 |
| MO_1031 | AC007431.1.1 | p.G30A | 17 | 55822545 | C | G | NA | 0.0 | 0 | |
| MO_1031 | LEKR1 | p.E87Q | 3 | 156570767 | G | C | NA | 0.0 | 0 | 0.25 |
| MO_1031 | C2orf73 | p.A139G | 2 | 54586123 | C | G | NA | 0.0 | 0 | 0.2 |
| MO_1031 | CACNA1E | p.A1489T | 1 | 181727218 | G | A | NA | 0.0 | 0 | 0.04 |
| MO_1031 | NRAP | p.E1274D | 10 | 115365614 | C | A | NA | 0.0 | 0 | 0.07 |
| MO_1031 | SLC10A1 | p.S206C | 14 | 70246028 | G | C | NA | 0.0 | 0 | 0.01 |
| MO_1031 | PDZD3 | p.S356L | 11 | 119059398 | C | T | NA | 0.0 | 1 | 0.08 |
| MO_1031 | DMRTA2 | splice acc. | 1 | 50885407 | C | T | NA | 0.0 | 0 | |
| MO_1031 | ALPPL2 | p.L273M | 2 | 233273244 | C | A | NA | 0.0 | 0 | 0.3 |
| MO_1031 | DDI1 | p.E395Q | 11 | 103908733 | G | C | NA | 0.0 | 0 | 0.25 |
| MO_1031 | TRDN | p.D275H | 6 | 123818368 | C | G | NA | 0.0 | 0 | 0 |
| MO_1031 | C10orf71 | p.L980P | 10 | 50533529 | T | C | NA | 0.0 | 0 | 0.23 |
| MO_1031 | GRP142 | p.G311S | 17 | 72368281 | G | A | NA | 0.0 | 1 | 0.03 |
| MO_1031 | GRP142 | p.E452Q | 17 | 72368704 | G | C | NA | 0.0 | 0 | 0.13 |
| MO_1031 | CCDC27 | p.E391K | 1 | 3679888 | G | A | NA | 0.0 | 0 | |
| MO_1031 | DCDC2C | p.I77M | 2 | 3774595 | C | G | NA | 0.0 | 0 | 0.01 |
| MO_1031 | COL6A5 | p.R1936W | 3 | 130158438 | C | T | NA | 0.0 | 0 | |
| MO_1031 | GHSR | p.Q299E | 3 | 172163157 | G | C | NA | 0.0 | 0 | 0.27 |
| MO_1031 | HTR1A | p.R297Q | 5 | 63256657 | C | T | NA | 0.0 | 0 | 0.33 |
| MO_1031 | GGNBP1 | p.E102K | 6 | 33556777 | G | A | NA | 0.0 | 0 | 0 |
| MO_1031 | SLC22A2 | p.E93Q | 6 | 160679513 | C | G | NA | 0.0 | 0 | 0.06 |
| MO_1031 | OR13C5 | p.L69M | 9 | 107361490 | A | T | NA | 0.0 | 0 | 0.15 |
| MO_1031 | OR52I2 | p.S260L | 11 | 4608821 | C | T | NA | 0.0 | 0 | 0 |
| MO_1031 | KRT76 | p.F269L | 12 | 53169180 | G | C | NA | 0.0 | 0 | 0.1 |
| MO_1031 | CYP1A1 | p.P82T | 15 | 75015195 | G | T | NA | 0.0 | 0 | 0 |
| MO_1031 | FAM46D | p.M388I | X | 79699202 | G | C | NA | 0.0 | 0 | 0.04 |
| MO_1031 | RBMXL3 | p.P321L | X | 114424966 | C | T | NA | 0.0 | 0 | |
| MO_1051 | CTNNA1 | p.D814N | 5 | 138268583 | G | A | NO | 146.0 | 0 | 0.18 |
| MO_1051 | TOP1 | p.E289K | 20 | 39726867 | G | A | NO | 45.1 | 0 | 0.26 |
| MO_1051 | TOP1 | p.K321N | 20 | 39726965 | G | C | NO | 45.1 | 0 | 0 |
| MO_1051 | MAP4 | p.E327Q | 3 | 47933003 | C | G | NO | 41.3 | 0 | 0.03 |
| MO_1051 | TP53 | p.G199E | 17 | 7578253 | C | T | NO | 18.3 | 37 | 0 |
| MO_1051 | ESR1 | p.Y537S | 6 | 152419923 | A | C | NO | 12.3 | 2 | 0 |
| MO_1051 | PTK2B | p.E474K | 8 | 27294717 | G | A | NO | 11.9 | 3 | 0.02 |
| MO_1051 | AR | p.G21A | X | 66765050 | G | C | NO | 9.3 | 0 | 0 |
| MO_1051 | PTPRT | p.S249L | 20 | 41385215 | G | A | NO | 8.7 | 0 | 0.35 |
| MO_1051 | FYN | p.R481Q | 6 | 111983114 | C | T | NO | 8.6 | 0 | 0.17 |
| MO_1051 | IGF1R | p.K560N | 15 | 99456363 | G | C | NO | 4.9 | 0 | 0.08 |
| MO_1051 | FLT4 | p.G723A | 5 | 180048007 | C | G | NO | 4.4 | 0 | 0 |
| MO_1051 | KAT6A | p.S378L | 8 | 41834756 | G | A | NO | 3.3 | 1 | 0.01 |
| MO_1051 | CD22 | p.A483T | 19 | 25831981 | G | A | NO | 2.6 | 0 | 0.46 |
| MO_1051 | ETV2 | p.S169L | 19 | 36134362 | G | T | NO | 2.3 | 0 | 0 |
| MO_1051 | PIK3CA | p.H1047R | 3 | 178952085 | A | G | YES | 2.1 | 1928 | 0.06 |
| MO_1051 | MYBL1 | p.E593K | 8 | 67479179 | C | T | NO | 1.2 | 0 | 0.15 |
| MO_1051 | BRIP1 | p.Q1151K | 17 | 59760956 | C | T | NO | 0.5 | 0 | 0 |
| MO_1051 | MAML2 | p.Q553X | 11 | 95825538 | G | A | NO | 0.4 | 0 | 1 |
| MO_1051 | POU6F2 | p.G159K | 7 | 39247183-4 | GG | AA | NO | 0.0 | 0 | |
| MO_1051 | ALK | p.E802K | 2 | 29456514 | C | T | NO | 0.0 | 0 | 0.04 |
| MO_1051 | RPS25 | p.K7N | 11 | 118888746 | C | G | NO | 407.3 | 0 | 0.06 |
| MO_1051 | TUBA1B | p.L70F | 12 | 49523299 | C | G | NO | 327.2 | 0 | 0 |
| MO_1051 | IL32 | p.D172G | 16 | 3119304 | A | G | YES | 211.6 | 0 | 0 |

TABLE 3-continued

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1051 | QARS | p.F268L | 3 | 49138860 | G | C | NO | 155.9 | 0 | 0 |
| MO_1051 | B4GALT3 | p.G167E | 1 | 161143829 | C | T | NO | 155.8 | 0 | 1 |
| MO_1051 | SF1 | p.H415Q | 11 | 64535140 | G | C | NO | 154.1 | 0 | 0 |
| MO_1051 | GANAB | p.D434N | 11 | 62398159 | C | T | NO | 131.0 | 0 | 0 |
| MO_1051 | PLXNB1 | p.E1309K | 3 | 48456626 | C | T | NO | 121.3 | 1 | 0.09 |
| MO_1051 | EFHD1 | p.A70V | 2 | 233498623 | C | T | NO | 109.5 | 0 | 0.23 |
| MO_1051 | DYNC1H1 | p.E1284K | 14 | 102466371 | G | A | NO | 90.4 | 0 | 0 |
| MO_1051 | PLEKHA6 | p.E527K | 1 | 204219688 | C | T | NO | 84.1 | 0 | 0 |
| MO_1051 | NTN4 | p.V258I | 12 | 96131736 | C | T | NO | 84.0 | 0 | 0.43 |
| MO_1051 | A1BG | p.S95L | 19 | 58864350 | G | A | YES | 83.4 | 0 | 0.73 |
| MO_1051 | SEC16A | p.Q2332E | 9 | 139338286 | G | C | NO | 81.6 | 0 | 0.01 |
| MO_1051 | SDR39U1 | p.G13V | 14 | 24909758 | C | A | NO | 77.5 | 0 |  |
| MO_1051 | ZFAND6 | p.S97F | 15 | 80414144 | C | T | YES | 70.5 | 0 | 0.01 |
| MO_1051 | HDAC7 | p.R277W | 12 | 48189511 | G | A | NO | 68.5 | 0 | 0 |
| MO_1051 | TMEM214 | p.S552F | 2 | 27267930 | C | T | NO | 62.7 | 0 | 0 |
| MO_1051 | LUC7L2 | p.D85H | 7 | 139083441 | G | C | NO | 58.9 | 0 | 0 |
| MO_1051 | PIN1 | p.V55I | 19 | 9949216 | G | A | NO | 51.5 | 0 | 0.3 |
| MO_1051 | ZNF296 | p.K279N | 19 | 45575450 | C | G | NO | 51.2 | 0 | 0.01 |
| MO_1051 | ZNF296 | p.W170X | 19 | 45575777 | C | T | NO | 51.2 | 0 | 0.42 |
| MO_1051 | MHRN1 | p.P27Q | 16 | 4675041 | C | A | NO | 46.3 | 0 | 0 |
| MO_1051 | NBPF10 | p.L92F | 1 | 145295521 | C | T | YES | 46.3 | 0 | 0.02 |
| MO_1051 | COMTD1 | p.R42Q | 10 | 76995471 | C | T | NO | 45.4 | 0 | 0.65 |
| MO_1051 | SLC15A3 | p.S358C | 11 | 60709541 | G | C | NO | 43.2 | 0 | 0.01 |
| MO_1051 | DAG1 | p.F692L | 3 | 49570020 | C | G | NO | 40.2 | 0 | 0.45 |
| MO_1051 | DAG1 | p.F791L | 3 | 49570317 | C | A | NO | 40.2 | 0 | 0 |
| MO_1051 | DAG1 | p.L819V | 3 | 49570399 | C | G | NO | 40.2 | 0 | 0.07 |
| MO_1051 | DAG1 | p.Q864K | 3 | 49570534 | C | A | NO | 40.2 | 0 | 0.12 |
| MO_1051 | COPB1 | p.D320N | 11 | 14502643 | C | T | NO | 37.8 | 0 | 0.01 |
| MO_1051 | HIST2H2BE | p.E114K | 1 | 149857851 | C | T | NO | 34.4 | 1 |  |
| MO_1051 | MSMO1 | p.H250Y | 4 | 166262964 | C | T | NO | 33.7 | 0 | 0 |
| MO_1051 | SLC38A10 | p.E519Q | 17 | 79226385 | C | G | NO | 33.6 | 0 | 0 |
| MO_1051 | SLC35B1 | p.S321Y | 17 | 47780285 | G | T | NO | 33.5 | 0 | 0 |
| MO_1051 | PSMD1 | p.G285D | 2 | 231937102 | G | A | NO | 30.2 | 0 | 0.4 |
| MO_1051 | NACC1 | p.R298W | 19 | 13246913 | C | T | YES | 30.1 | 0 | 0.02 |
| MO_1051 | ZFP36L2 | p.Q139X | 2 | 43452528 | G | A | NO | 30.0 | 0 | 0.32 |
| MO_1051 | THBS2 | p.H201Y | 6 | 169648520 | G | A | NO | 29.8 | 0 | 0.05 |
| MO_1051 | CHD1 | p.Q893E | 5 | 96218833 | G | C | NO | 29.1 | 0 | 0 |
| MO_1051 | SKI | p.S515C | 1 | 2235801 | C | G | NO | 27.0 | 0 | 0.3 |
| MO_1051 | DHX30 | p.E368K | 3 | 47887268 | G | A | NO | 26.9 | 1 | 0.02 |
| MO_1051 | FCGR3A | p.F212V | 1 | 161514542 | A | C | NO | 26.7 | 0 | 0.24 |
| MO_1051 | GRSF1 | p.R42C | 4 | 71705097 | G | A | NO | 26.7 | 0 |  |
| MO_1051 | RAVER1 | p.E642K | 19 | 10429021 | C | T | NO | 25.8 | 0 | 0.33 |
| MO_1051 | TRIM26 | p.E391Q | 6 | 30154102 | C | G | NO | 25.2 | 0 | 0.09 |
| MO_1051 | LSS | p.A693S | 21 | 47611140 | C | A | NO | 25.0 | 0 | 0.54 |
| MO_1051 | NBPF12 | p.E84Q | 1 | 146397433 | G | C | NO | 24.7 | 0 | 0 |
| MO_1051 | NBPF12 | p.E50Q | 1 | 146398387 | G | C | NO | 24.7 | 0 | 1 |
| MO_1051 | BRAT1 | p.S274F | 7 | 2582940 | G | A | NO | 23.9 | 0 | 0.7 |
| MO_1051 | USP22 | p.S307L | 17 | 20916167 | G | A | NO | 23.3 | 0 | 0 |
| MO_1051 | FAM208A | p.D824E | 3 | 56675524 | G | C | NO | 22.7 | 0 | 0.63 |
| MO_1051 | DYRK1A | p.S258C | 21 | 38862585 | C | G | NO | 22.6 | 0 | 0 |
| MO_1051 | CEP104 | p.E160K | 1 | 3761864 | C | T | NO | 22.5 | 0 | 0.33 |
| MO_1051 | SHROOM3 | p.Q331X | 4 | 77660317 | C | T | NO | 21.8 | 0 | 0.36 |
| MO_1051 | MAN2A1 | p.E1030K | 5 | 109190952 | G | A | NO | 21.5 | 0 | 0.84 |
| MO_1051 | LFNG | p.F350L | 7 | 2566532 | C | G | NO | 21.1 | 0 | 0 |
| MO_1051 | CC2D1A | p.E772Q | 19 | 14038076 | G | C | NO | 20.4 | 0 | 0.01 |
| MO_1051 | ZNF213 | p.K355X | 16 | 3191031 | C | T | NO | 20.2 | 0 | 0.04 |
| MO_1051 | LRPPRC | p.R799T | 2 | 44170934 | C | G | NO | 20.1 | 0 | 0.02 |
| MO_1051 | ANKRD30A | p.E1234K | 10 | 37508508 | G | A | NO | 20.0 | 0 | 0.05 |
| MO_1051 | NUP205 | p.S1666I | 7 | 135315156 | G | T | YES | 19.7 | 0 | 0.01 |
| MO_1051 | RAP1GAP | p.S525C | 1 | 21929351 | G | C | NO | 19.4 | 0 | 0 |
| MO_1051 | KLHL17 | p.E159K | 1 | 897116 | G | A | NO | 19.4 | 0 | 0 |
| MO_1051 | HTATSF1 | p.D669H | X | 135593909 | G | C | NO | 19.4 | 0 | 0 |
| MO_1051 | GBP2 | p.P174A | 1 | 89583365 | G | C | NO | 19.2 | 0 | 0 |
| MO_1051 | BAZ1A | p.D639H | 14 | 35253050 | G | G | NO | 19.0 | 0 | 0 |
| MO_1051 | ABCG1 | p.E191K | 21 | 43697038 | G | A | NO | 18.8 | 0 | 0.31 |
| MO_1051 | TRIM41 | p.F425L | 5 | 180660747 | C | G | NO | 18.6 | 0 | 0.1 |
| MO_1051 | TRAPPC4 | p.S132L | 11 | 118890904 | C | T | NO | 17.5 | 0 | 0.01 |
| MO_1051 | GAS6 | p.E385X | 13 | 114531675 | C | A | NO | 17.1 | 0 | 0 |
| MO_1051 | ITSN1 | p.E686K | 21 | 35169786 | G | A | NO | 16.3 | 0 | 0.12 |
| MO_1051 | CD52 | p.G43E | 1 | 26646735 | G | A | NO | 15.9 | 0 |  |
| MO_1051 | HEXDC | p.A413S | 17 | 80399749 | C | T | NO | 15.3 | 0 | 0.73 |
| MO_1051 | NT5DC1 | p.L21V | 6 | 116422154 | C | G | NO | 15.1 | 0 | 0.01 |
| MO_1051 | GATAD2B | p.M107I | 1 | 153800503 | G | G | NO | 15.1 | 0 | 0 |
| MO_1051 | USP48 | p.D893N | 1 | 22028041 | C | T | NO | 14.9 | 0 | 0.01 |
| MO_1051 | USP48 | p.E858K | 1 | 22030055 | C | T | NO | 14.9 | 0 | 0.23 |
| MO_1051 | SIN3A | p.R1263C | 15 | 75664355 | G | A | NO | 14.6 | 0 | 0 |
| MO_1051 | PLEKHG5 | p.Q473H | 1 | 6530918 | C | G | NO | 14.3 | 0 | 0.06 |

TABLE 3-continued

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1051 | CCDC57 | p.E754K | 17 | 80086458 | C | T | NO | 14.1 | 0 | 0 |
| MO_1051 | POLR2B | p.K497N | 4 | 57876613 | A | C | NO | 14.0 | 0 | 0 |
| MO_1051 | HOXB7 | p.T163A | 17 | 46685371 | T | C | NO | 13.2 | 0 | 0 |
| MO_1051 | NOTCH2NL | p.S67P | 1 | 145273345 | T | C | NO | 13.2 | 0 | 0.4 |
| MO_1051 | PCMTD1 | p.R335T | 8 | 52732981 | C | G | NO | 13.1 | 0 | 0 |
| MO_1051 | MRPS18C | p.P133S | 4 | 84382318 | C | T | NO | 13.1 | 0 | 0 |
| MO_1051 | GMNN | p.D204N | 6 | 24788007 | G | A | NO | 12.9 | 0 | |
| MO_1051 | GTPBP3 | p.R14H | 19 | 17448461 | G | A | NO | 12.8 | 0 | 0.1 |
| MO_1051 | NOL8 | p.E759K | 9 | 95076632 | C | T | NO | 12.7 | 0 | 0.01 |
| MO_1051 | IMPAD1 | p.S244F | 8 | 57878827 | G | A | NO | 11.7 | 0 | 0 |
| MO_1051 | VPS13C | p.E3613K | 15 | 62160884 | C | T | NO | 11.6 | 0 | 0.02 |
| MO_1051 | USP36 | p.E484K | 17 | 76803676 | C | T | NO | 11.4 | 0 | 0.02 |
| MO_1051 | ZNF646 | p.D551N | 16 | 31089296 | G | A | NO | 11.4 | 1 | 0.71 |
| MO_1051 | ZKSCAN1 | p.E320Q | 7 | 99631086 | G | C | NO | 11.4 | 0 | 0.15 |
| MO_1051 | MANBA | p.E697Q | 4 | 103557090 | C | G | NO | 11.2 | 0 | 0.01 |
| MO_1051 | FAM8A1 | p.E94Q | 6 | 17600920 | G | C | NO | 11.0 | 1 | 0.1 |
| MO_1051 | SENP3 | p.D337H | 17 | 7468329 | G | C | NO | 10.9 | 0 | 0 |
| MO_1051 | YLPM1 | p.D377H | 14 | 75247126 | G | C | NO | 10.8 | 2 | 0 |
| MO_1051 | TBC1D7 | p.S292L | 6 | 13305340 | G | A | NO | 10.7 | 0 | 0 |
| MO_1051 | CDRT4 | p.S80C | 17 | 15341307 | G | C | NO | 10.0 | 0 | 0.07 |
| MO_1051 | DDX19A | p.E299X | 16 | 70400639 | G | T | NO | 9.7 | 0 | 0 |
| MO_1051 | ZNF747 | p.L16V | 16 | 30545955 | G | C | NO | 9.5 | 0 | 0.06 |
| MO_1051 | C12orf35 | p.M1479I | 12 | 32138326 | G | A | NO | 9.5 | 0 | 0.52 |
| MO_1051 | DHX29 | p.E1180Q | 5 | 54558748 | C | G | NO | 9.2 | 0 | 0.64 |
| MO_1051 | HIVEP1 | p.S1864F | 6 | 12125619 | C | T | NO | 8.4 | 0 | 0.05 |
| MO_1051 | HDAC5 | p.W792L | 17 | 42161001 | C | A | NO | 8.3 | 0 | 0 |
| MO_1051 | C5orf51 | p.E28K | 5 | 41904551 | G | A | NO | 7.7 | 0 | 0.03 |
| MO_1051 | C1orf54 | p.D110H | 1 | 150253273 | G | C | NO | 7.7 | 0 | 0.05 |
| MO_1051 | AFF4 | p.L723F | 5 | 132232153 | C | G | NO | 7.6 | 0 | 0 |
| MO_1051 | NUFIP2 | p.L644F | 17 | 27613080 | C | G | NO | 7.6 | 0 | 0.26 |
| MO_1051 | NUFIP2 | p.G331R | 17 | 27614021 | C | G | NO | 7.6 | 0 | 0 |
| MO_1051 | NUFIP2 | p.A305S | 17 | 27614099 | C | A | NO | 7.6 | 0 | 0 |
| MO_1051 | NUFIP2 | p.T259P | 17 | 27614237 | C | G | NO | 7.6 | 0 | 0.03 |
| MO_1051 | CCDC25 | p.E193K | 8 | 27598009 | C | T | NO | 7.6 | 0 | 0.05 |
| MO_1051 | MASP1 | p.F113L | 3 | 186980407 | G | C | NO | 7.2 | 0 | 0.13 |
| MO_1051 | MCM2 | p.E235K | 3 | 127324990 | G | A | NO | 6.8 | 0 | 0.79 |
| MO_1051 | DNAH14 | p.E3150Q | 1 | 225519142 | G | C | NO | 6.8 | 0 | 0.17 |
| MO_1051 | DNAH14 | p.E3166K | 1 | 225519190 | G | A | NO | 6.8 | 0 | 0.02 |
| MO_1051 | GPATCH8 | p.D875N | 17 | 42476822 | C | T | NO | 6.6 | 0 | 0.95 |
| MO_1051 | PAPD5 | p.E547K | 16 | 50259080 | G | A | NO | 6.6 | 0 | 0.08 |
| MO_1051 | PCNXL2 | p.I1505T | 1 | 233160983 | A | G | NO | 6.1 | 0 | 0 |
| MO_1051 | PANX1 | p.F15L | 11 | 93862523 | C | G | NO | 6.1 | 0 | 0.25 |
| MO_1051 | KIAA1731 | p.K2N | 11 | 93399879 | G | C | NO | 5.7 | 0 | 0.01 |
| MO_1051 | FAM83D | p.E36K | 20 | 37555101 | G | A | NO | 5.4 | 0 | 0.03 |
| MO_1051 | FAM83D | p.D93N | 20 | 37555272 | G | A | NO | 5.4 | 0 | 0.09 |
| MO_1051 | MAP4K4 | p.R1045Q | 2 | 102493549 | G | A | NO | 5.4 | 0 | 0 |
| MO_1051 | LYST | p.L2316V | 1 | 235920694 | G | C | NO | 5.4 | 0 | 0.24 |
| MO_1051 | CYP4F2 | p.E328Q | 19 | 15997055 | C | G | NO | 5.2 | 0 | 0.07 |
| MO_1051 | AVIL | p.E304Q | 12 | 58203409 | C | G | NO | 5.2 | 0 | 0 |
| MO_1051 | HSPA13 | p.S304C | 21 | 15746443 | G | C | NO | 5.1 | 0 | 0 |
| MO_1051 | TRMT12 | p.E391K | 8 | 125464339 | G | A | NO | 5.0 | 0 | 0.13 |
| MO_1051 | PPP1R12B | p.S516L | 1 | 202411580 | C | T | NO | 4.9 | 0 | 0.02 |
| MO_1051 | GTF2E1 | p.E389K | 3 | 120500162 | G | A | NO | 4.8 | 0 | 0.07 |
| MO_1051 | PGLYRP2 | p.R430H | 19 | 15582755 | C | T | YES | 4.7 | 0 | 0 |
| MO_1051 | NFATC1 | p.E917K | 18 | 77287533 | G | A | NO | 4.5 | 0 | 0 |
| MO_1051 | CD97 | p.F645L | 19 | 14517256 | C | G | NO | 4.3 | 0 | 0.04 |
| MO_1051 | HELQ | p.D771H | 4 | 84350884 | C | G | NO | 4.1 | 0 | 0.1 |
| MO_1051 | RANBP6 | p.L818F | 9 | 6013154 | C | G | NO | 4.1 | 0 | 0.03 |
| MO_1051 | CCDC99 | p.E213K | 5 | 169021254 | G | A | NO | 3.9 | 0 | 0.01 |
| MO_1051 | C2orf69 | p.G62E | 2 | 200776346 | G | A | NO | 3.8 | 0 | 0 |
| MO_1051 | C14orf126 | p.E167K | 14 | 31917343 | C | T | NO | 3.6 | 0 | 0.02 |
| MO_1051 | TTC30A | p.E518K | 2 | 178481878 | C | T | NO | 3.5 | 0 | 0 |
| MO_1051 | FBXL7 | p.E314K | 5 | 15938759 | G | A | NO | 3.3 | 0 | 0.07 |
| MO_1051 | ZNF770 | p.A140T | 15 | 35275218 | C | T | YES | 3.0 | 0 | 0.24 |
| MO_1051 | XDH | p.R943W | 2 | 31572694 | G | A | YES | 2.9 | 0 | 0.01 |
| MO_1051 | OBSCN | p.E4760K | 1 | 228506731 | G | A | NO | 2.9 | 0 | 0 |
| MO_1051 | C2orf67 | p.S519L | 2 | 210940475 | G | A | NO | 2.7 | 0 | 0.03 |
| MO_1051 | C3orf15 | splice acc. | 3 | 119427437 | G | C | NO | 2.7 | 0 | |
| MO_1051 | PPTC7 | p.D78N | 12 | 110989765 | C | T | NO | 2.7 | 0 | 0 |
| MO_1051 | DOCK10 | p.E1140Q | 2 | 225672795 | C | G | NO | 2.7 | 0 | 0.01 |
| MO_1051 | EPDR1 | p.D291H | 7 | 37989834 | G | C | NO | 2.5 | 0 | 0.07 |
| MO_1051 | SEMA5B | p.E768Q | 3 | 122632250 | C | G | NO | 2.5 | 0 | 0.51 |
| MO_1051 | FSIP2 | p.E6754K | 2 | 186678437 | G | A | NO | 2.5 | 0 | 0.01 |
| MO_1051 | KIAA0753 | splice acc. | 17 | 6528182 | C | T | NO | 2.4 | 0 | |
| MO_1051 | INTS2 | p.E368Q | 17 | 59984872 | C | G | NO | 2.3 | 0 | 0.49 |
| MO_1051 | KIAA1549 | p.P196A | 7 | 138603636 | G | C | NO | 2.3 | 0 | 0 |
| MO_1051 | FGD6 | p.E1422Q | 12 | 95475325 | C | G | NO | 2.2 | 0 | 0.02 |

TABLE 3-continued

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1051 | FAM22D | p.H35Y | 10 | 89118125 | C | T | NO | 2.0 | 0 | 0.42 |
| MO_1051 | ZNF546 | p.S570X | 19 | 40520886 | C | G | NO | 1.9 | 0 | 0.29 |
| MO_1051 | MAP1B | p.E678Q | 5 | 71491214 | G | C | NO | 1.8 | 1 | 0.04 |
| MO_1051 | SRR | p.G192V | 17 | 2224891 | G | T | NO | 1.7 | 0 | 0 |
| MO_1051 | ELOVL2 | p.L235H | 6 | 10989997 | A | T | NO | 1.6 | 0 | 0.17 |
| MO_1051 | FJX1 | p.D291H | 11 | 35641055 | G | C | NO | 1.6 | 0 | 0 |
| MO_1051 | FEZ1 | p.E190Q | 11 | 125330493 | C | G | NO | 1.4 | 0 | 0.03 |
| MO_1051 | P2RX7 | p.V475I | 12 | 121622240 | G | A | YES | 1.4 | 0 | 0.17 |
| MO_1051 | KIAA1524 | p.E785K | 3 | 108272549 | C | T | NO | 1.2 | 0 | 0.18 |
| MO_1051 | GRIN2D | p.E815X | 19 | 48945409 | G | T | NO | 1.2 | 0 | 0.1 |
| MO_1051 | ATOH8 | p.S209L | 2 | 85981938 | C | T | NO | 1.1 | 0 | 0.02 |
| MO_1051 | KIF21B | p.L1373F | 1 | 200948667 | G | A | NO | 0.9 | 0 | |
| MO_1051 | ABCA10 | p.G557E | 17 | 67189361 | C | T | NO | 0.9 | 0 | 0 |
| MO_1051 | PLXNA4 | p.V591I | 7 | 131912321 | C | T | YES | 0.8 | 0 | 0.25 |
| MO_1051 | ST8SIA4 | p.M134I | 5 | 100222148 | C | T | NO | 0.7 | 0 | 0.01 |
| MO_1051 | DNAH7 | p.E554K | 2 | 196851884 | C | T | NO | 0.6 | 0 | 0.29 |
| MO_1051 | FAM124B | p.S398C | 2 | 225244465 | G | C | NO | 0.5 | 0 | 0.01 |
| MO_1051 | LINGO4 | p.P524S | 1 | 151773611 | G | A | YES | 0.5 | 0 | 0.02 |
| MO_1051 | PNMA3 | p.E189K | X | 152225977 | G | A | NO | 0.4 | 0 | 0.01 |
| MO_1051 | AKR1E2 | p.S126X | 10 | 4877919 | C | A | NO | 0.4 | 0 | 0.04 |
| MO_1051 | SHANK1 | p.S212L | 19 | 51217444 | G | A | NO | 0.4 | 0 | 0 |
| MO_1051 | C9orf153 | p.R73T | 9 | 88842794 | C | G | NO | 0.3 | 0 | 0.05 |
| MO_1051 | FCAMR | p.R18K | 1 | 207140983 | C | T | NO | 0.3 | 0 | 0 |
| MO_1051 | CDH7 | p.D288N | 18 | 63491948 | G | A | NO | 0.3 | 0 | 0.01 |
| MO_1051 | FHOD3 | p.K788N | 18 | 34298150 | G | C | NO | 0.2 | 0 | 0.04 |
| MO_1051 | CUBN | p.H2474Y | 10 | 16955923 | G | A | NO | 0.2 | 0 | 0.01 |
| MO_1051 | PHOSPHO1 | p.E117Q | 17 | 47302063 | C | G | NO | 0.2 | 0 | 0.03 |
| MO_1051 | FBXO15 | p.R297C | 18 | 71790624 | G | A | YES | 0.2 | 2 | 0 |
| MO_1051 | CCDC36 | p.Q272X | 3 | 49293744 | C | T | NO | 0.2 | 0 | 0 |
| MO_1051 | FAT4 | p.Q760X | 4 | 126239844 | C | T | NO | 0.2 | 0 | 0.81 |
| MO_1051 | FAT4 | p.S1870C | 4 | 126329638 | G | C | NO | 0.2 | 0 | 0.06 |
| MO_1051 | ADCY10 | p.R109Q | 1 | 167871010 | C | T | NO | 0.2 | 1 | 0.42 |
| MO_1051 | FBXL13 | p.M68I | 7 | 102695601 | C | T | NO | 0.2 | 0 | 0.24 |
| MO_1051 | DNAH6 | p.D2485Y | 2 | 84921533 | G | T | NO | 0.2 | 0 | 0 |
| MO_1051 | PAPPA2 | p.R1485C | 1 | 176738881 | C | T | NO | 0.2 | 0 | 0 |
| MO_1051 | PI16 | splice acc. | 6 | 36926920 | G | A | NO | 0.1 | 0 | |
| MO_1051 | KIRREL2 | p.L884V | 19 | 36357317 | C | G | NO | 0.1 | 0 | 0.16 |
| MO_1051 | CR1 | p.Q572H | 1 | 207726161 | G | T | YES | 0.1 | 0 | 0.04 |
| MO_1051 | C9orf131 | p.Q171E | 9 | 35043137 | C | G | NO | 0.1 | 0 | 0 |
| MO_1051 | ZPLD1 | p.S375F | 3 | 102196290 | C | T | NO | 0.1 | 0 | 0.01 |
| MO_1051 | HOXA2 | p.Q252X | 7 | 27140722 | G | A | NO | 0.1 | 0 | 0.07 |
| MO_1051 | EYS | p.I3056M | 6 | 64430759 | G | C | NO | 0.1 | 0 | 0 |
| MO_1051 | BNC1 | p.G596A | 15 | 83932216 | C | G | NO | 0.1 | 0 | 0.43 |
| MO_1051 | TYRP1 | p.E525K | 9 | 12709141 | G | A | NO | 0.1 | 0 | 0.01 |
| MO_1051 | GCK | p.E246K | 7 | 44187379 | C | T | NO | 0.0 | 0 | 0.01 |
| MO_1051 | FCRLA | p.E156K | 1 | 161681957 | G | A | NO | 0.0 | 0 | 0.02 |
| MO_1051 | CNKSR2 | p.G368E | X | 21549985 | G | A | NO | 0.0 | 0 | 0.05 |
| MO_1051 | ODZ1 | p.M1531I | X | 123554529 | C | T | NO | 0.0 | 0 | 0.34 |
| MO_1051 | MYT1L | p.P351S | 2 | 1926490 | G | A | NO | 0.0 | 0 | 0.48 |
| MO_1051 | TTN | p.E4790Q | 2 | 179500735 | C | G | NO | 0.0 | 0 | |
| MO_1051 | TTN | p.R3402K | 2 | 179621465 | C | T | NO | 0.0 | 0 | |
| MO_1051 | RPH3A | p.D676H | 12 | 113334526 | G | C | NO | 0.0 | 0 | 0 |
| MO_1051 | MUC2 | p.G305S | 11 | 1079696 | G | A | YES | 0.0 | 0 | 0.88 |
| MO_1051 | FOXI2 | p.P14L | 10 | 129535578 | C | T | NO | 0.0 | 0 | 0.11 |
| MO_1051 | GABRR1 | p.E432K | 6 | 89888635 | C | T | NO | 0.0 | 1 | 0.09 |
| MO_1051 | RHAG | p.Q104K | 6 | 49586923 | G | T | NO | 0.0 | 0 | 0.21 |
| MO_1051 | LRRTM4 | p.D54Y | 2 | 77746835 | C | A | NO | 0.0 | 0 | 0 |
| MO_1051 | ADGB | p.L1592F | 6 | 147123105 | G | C | NO | 0.0 | 0 | 0.18 |
| MO_1051 | LEKR1 | p.E12K | 3 | 156547152 | G | A | NO | 0.0 | 0 | 0.18 |
| MO_1051 | A2ML1 | p.L1319F | 12 | 9020847 | C | T | NO | 0.0 | 0 | 0.19 |
| MO_1051 | ATP12A | p.L898V | 13 | 25283895 | C | G | NO | 0.0 | 0 | 0.01 |
| MO_1051 | SI | p.D1389H | 3 | 164727081 | C | G | NO | 0.0 | 0 | 0 |
| MO_1051 | CACNA1E | p.R3C | 1 | 181452887 | C | T | NO | 0.0 | 0 | 0 |
| MO_1051 | CBLN4 | p.H125Y | 20 | 54575822 | G | A | NO | 0.0 | 0 | 0 |
| MO_1051 | NKX2-3 | p.D234H | 10 | 101295083 | G | C | NO | 0.0 | 0 | 0 |
| MO_1051 | CIB4 | p.E16Q | 2 | 26864137 | C | G | NO | 0.0 | 1 | 0.02 |
| MO_1051 | OR5K3 | p.R259X | 3 | 98110284 | C | T | NO | 0.0 | 0 | 1 |
| MO_1051 | C9orf135 | splice acc. | 9 | 72471470 | G | C | NO | 0.0 | 0 | |
| MO_1051 | SLC1A6 | p.F52L | 19 | 15083567 | G | C | NO | 0.0 | 0 | 0.03 |
| MO_1051 | SPINT4 | p.R65I | 20 | 44352597 | G | T | NO | 0.0 | 0 | 0.09 |
| MO_1069 | ESR1 | p.D538G | 6 | 152419926 | A | G | NO | 80.5 | 2 | 0 |
| MO_1069 | ARID1B | p.D2175G | 6 | 157528853 | A | G | NO | 7.9 | 0 | 0.01 |
| MO_1069 | MTOR | p.R281H | 1 | 11308150 | C | T | YES | 5.5 | 1 | 0.01 |
| MO_1069 | ARID2 | p.E245X | 12 | 46230399 | G | T | NO | 5.4 | 0 | 0.04 |
| MO_1069 | FANCD2 | p.Q1100E | 3 | 10127569 | C | G | NO | 5.1 | 0 | 1 |
| MO_1069 | MUC16 | p.S2675L | 19 | 9083791 | G | A | NO | 154.6 | 0 | 0.16 |
| MO_1069 | UBA1 | p.N928I | X | 47072525 | A | T | NO | 140.5 | 0 | 0 |

TABLE 3-continued

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1069 | RPS6KB2 | p.V48L | 11 | 67196613 | G | T | YES | 72.6 | 0 | 0.08 |
| MO_1069 | C11orf80 | p.A582T | 11 | 66605913 | G | A | NO | 58.7 | 0 | 0 |
| MO_1069 | MOGS | p.A470D | 2 | 74689507 | G | T | YES | 38.1 | 0 | 0.03 |
| MO_1069 | CDR2L | p.E193X | 17 | 72999348 | G | T | NO | 36.9 | 0 | 0.06 |
| MO_1069 | TBC1D9B | p.V43M | 5 | 179331804 | C | T | NO | 34.8 | 0 | 0.01 |
| MO_1069 | HCFC1R1 | p.R46L | 16 | 3073490 | C | A | NO | 32.1 | 0 | 0.35 |
| MO_1069 | UBE2A | p.T69I | X | 118716605 | C | T | YES | 29.2 | 0 | 0.84 |
| MO_1069 | CCDC88C | p.Q1770R | 14 | 91739747 | T | C | NO | 29.0 | 0 | 0.53 |
| MO_1069 | CASKIN2 | p.S557I | 17 | 73499750 | C | A | NO | 27.6 | 0 | 0 |
| MO_1069 | MBD3 | p.F138L | 19 | 1582706 | G | C | NO | 27.0 | 0 | 0.01 |
| MO_1069 | ACBD3 | p.D392Y | 1 | 226340237 | C | A | NO | 22.1 | 0 |  |
| MO_1069 | PDE4DIP | p.K223Q | 1 | 144923791 | T | G | NO | 20.0 | 0 | 0.09 |
| MO_1069 | CENPF | p.E1583Q | 1 | 214816428 | G | C | NO | 18.4 | 0 |  |
| MO_1069 | CENPF | p.S1589R | 1 | 214816446 | A | C | NO | 18.4 | 0 |  |
| MO_1069 | TNC | p.V708E | 9 | 117846496 | A | T | NO | 17.3 | 0 | 0 |
| MO_1069 | CCDC9 | p.G459R | 19 | 47774714 | G | A | NO | 16.3 | 1 | 0.69 |
| MO_1069 | NFRKB | p.R184W | 11 | 129755459 | G | A | NO | 13.7 | 0 | 0.02 |
| MO_1069 | KIAA1683 | p.P36S | 19 | 18378244 | G | A | YES | 12.1 | 0 | 0 |
| MO_1069 | CTSC | p.L16F | 11 | 88070795 | G | A | YES | 12.0 | 0 | 0.09 |
| MO_1069 | DUSP10 | p.Y31S | 1 | 221912995 | T | G | NO | 10.0 | 0 | 0 |
| MO_1069 | C15orf39 | p.R824X | 15 | 75500859 | C | T | NO | 8.7 | 0 | 0.03 |
| MO_1069 | ITGAX | p.C108G | 16 | 31368577 | T | G | NO | 8.7 | 0 | 0 |
| MO_1069 | FAM8A1 | p.S147F | 6 | 17601080 | C | T | YES | 8.4 | 0 | 0.03 |
| MO_1069 | NLGN2 | p.R642Q | 17 | 7320535 | G | A | NO | 6.7 | 0 |  |
| MO_1069 | PLS1 | p.R274Q | 3 | 142403170 | G | A | NO | 6.5 | 0 | 0.01 |
| MO_1069 | TTI2 | p.H23Y | 8 | 33370065 | G | A | YES | 6.1 | 0 | 0.15 |
| MO_1069 | PHF20L1 | p.A95P | 8 | 133807006 | G | C | YES | 5.5 | 0 | 0 |
| MO_1069 | ATRN | p.H427Y | 20 | 3541384 | C | T | YES | 4.6 | 0 | 0.13 |
| MO_1069 | DIEXF | p.S246L | 1 | 210010231 | C | T | YES | 4.3 | 0 | 0.31 |
| MO_1069 | UHRF2 | splice donor | 9 | 6493933 | G | A | NO | 3.9 | 0 |  |
| MO_1069 | EFCAB7 | p.D269N | 1 | 64011587 | G | A | YES | 3.3 | 0 | 0.02 |
| MO_1069 | TTC27 | UNKNOWN | 2 | 32991568 | G | C | NO | 2.9 | 0 |  |
| MO_1069 | KLHL24 | p.I52V | 3 | 183368298 | A | G | NO | 2.6 | 0 | 0.17 |
| MO_1069 | SHPRH | p.E1228A | 6 | 146243847 | T | G | NO | 2.6 | 0 | 0.08 |
| MO_1069 | PTPLAD2 | p.V119I | 1 | 21015925 | C | T | NO | 2.2 | 0 | 0.76 |
| MO_1069 | RFX7 | p.Q703H | 15 | 56387526 | T | G | NO | 1.4 | 0 | 0 |
| MO_1069 | C7orf60 | p.G7D | 7 | 112579786 | C | T | YES | 1.1 | 0 | 0 |
| MO_1069 | ADAMTS7 | p.V49A | 15 | 79092844 | A | G | NO | 1.0 | 0 | 0.04 |
| MO_1069 | FAM227A | p.R369X | 22 | 39003415 | G | A | NO | 0.9 | 0 | 1 |
| MO_1069 | CDC14A | p.R236H | 1 | 100928306 | G | A | NO | 0.7 | 0 | 0 |
| MO_1069 | CHST2 | p.P284A | 3 | 142840508 | C | G | NO | 0.5 | 0 | 0.27 |
| MO_1069 | ADAMTSL1 | p.R1093C | 9 | 18777504 | C | T | YES | 0.5 | 0 | 0.01 |
| MO_1069 | MCTF2 | p.K856Q | 15 | 95020020 | A | C | YES | 0.5 | 0 | 0.02 |
| MO_1069 | MAPTA | p.V1155I | 15 | 43817134 | G | A | NO | 0.5 | 0 | 0.06 |
| MO_1069 | PRDM8 | p.A395T | 4 | 81123799 | G | A | YES | 0.2 | 0 | 0.17 |
| MO_1069 | ANKRD1 | p.G209A | 10 | 92675953 | C | G | NO | 0.1 | 0 | 0 |
| MO_1069 | ZNF469 | p.G694V | 16 | 88495959 | G | T | NO | 0.1 | 0 | 0.02 |
| MO_1069 | C18orf34 | p.L444F | 18 | 30846957 | C | G | NO | 0.1 | 0 | 0.08 |
| MO_1069 | PAPPA2 | p.P960L | 1 | 176668368 | C | T | YES | 0.1 | 0 | 0 |
| MO_1069 | HOXD10 | p.E227Q | 2 | 176982240 | G | C | NO | 0.1 | 0 | 0.09 |
| MO_1069 | SCN3A | p.F1177V | 2 | 165970466 | C | C | NO | 0.1 | 0 | 0.05 |
| MO_1069 | PDIA2 | p.W417C | 16 | 336564 | G | T | YES | 0.0 | 0 | 0 |
| MO_1069 | SHISA6 | p.F128V | 17 | 11145121 | T | G | NO | 0.0 | 0 | 0 |
| MO_1069 | KIAA1549L | p.E1244A | 11 | 33612838 | A | C | NO | 0.0 | 0 | 0.01 |
| MO_1069 | ATP8A2 | splice acc. | 13 | 26043114 | G | T | NO | 0.0 | 0 |  |
| MO_1069 | LRRN4 | p.A82V | 20 | 6033201 | G | A | NO | 0.0 | 0 | 0.18 |
| MO_1069 | ABCD2 | p.D737H | 12 | 39947728 | C | G | NO | 0.0 | 0 | 0.01 |
| MO_1069 | FAT3 | p.T2716A | 11 | 92534325 | A | G | NO | 0.0 | 0 | 0.18 |
| MO_1069 | BTNL8 | p.Q426X | 5 | 180377317 | C | T | NO | 0.0 | 0 | 1 |
| MO_1069 | LRRC7 | p.S1063I | 1 | 70504809 | G | T | YES | 0.0 | 1 | 0 |
| MO_1069 | PLA2G1B | p.Y133X | 12 | 120760044 | A | T | NO | 0.0 | 0 |  |
| MO_1069 | HMX1 | p.V215D | 4 | 8869822 | A | T | NO | 0.0 | 0 | 0 |
| MO_1069 | AKR1B10 | p.S305C | 7 | 134225804 | C | G | NO | 0.0 | 0 | 0.05 |
| MO_1069 | SLC18A3 | p.A180V | 10 | 50819325 | C | T | NO | 0.0 | 0 | 0.38 |
| MO_1069 | OGDHL | p.I517F | 10 | 50953470 | T | A | NO | 0.0 | 0 | 0 |
| MO_1069 | OR4C16 | p.G106R | 11 | 55339919 | G | C | NO | 0.0 | 0 | 0.01 |
| MO_1069 | OR10G4 | p.A90T | 11 | 123886549 | G | A | NO | 0.0 | 0 | 0.79 |
| MO_1129 | ESR1 | p.Y537S | 6 | 152419923 | A | C | NO | 76.4 | 2 | 0 |
| MO_1129 | DEK | p.A18T | 6 | 18264167 | C | T | YES | 22.8 | 0 | 0.02 |
| MO_1129 | PIK3CA | p.E542K | 3 | 178936082 | G | A | YES | 4.3 | 603 | 0.04 |
| MO_1129 | ELK4 | p.L412V | 1 | 205585736 | G | C | NO | 4.2 | 0 |  |
| MO_1129 | MLL | p.G1181V | 11 | 118348889 | G | T | NO | 3.6 | 0 | 0 |
| MO_1129 | MAP3K5 | p.C200Y | 6 | 137026261 | C | T | NO | 0.7 | 0 | 0.05 |
| MO_1129 | WDR1 | p.A239S | 4 | 10089919 | C | A | NO | 105.9 | 0 | 0.13 |
| MO_1129 | TRIO | splice donor | 5 | 14359641 | G | A | NO | 82.4 | 0 |  |
| MO_1129 | SPEG | p.G397S | 2 | 220313069 | G | A | NO | 37.1 | 0 | 0.07 |
| MO_1129 | USP5 | p.E29Q | 12 | 6961428 | G | C | NO | 30.2 | 0 | 0 |

TABLE 3-continued

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1129 | HEATR2 | p.A666V | 7 | 813750 | C | T | YES | 20.8 | 0 | 0.01 |
| MO_1129 | TUBB2A | p.A248V | 6 | 3154692 | G | A | NO | 10.6 | 0 | 0 |
| MO_1129 | CMAS | p.V136I | 12 | 22208391 | G | A | YES | 9.8 | 0 | 0.17 |
| MO_1129 | DHX8 | p.Q317X | 17 | 41570898 | C | T | NO | 6.5 | 0 | 0.01 |
| MO_1129 | ZP3 | p.M289V | 7 | 76069886 | A | G | NO | 5.8 | 0 | 0.29 |
| MO_1129 | ZP3 | p.R294T | 7 | 76069902 | G | C | YES | 5.8 | 0 | 0.25 |
| MO_1129 | ZCCHC6 | p.S1170L | 9 | 88924451 | G | A | YES | 5.4 | 0 | 0 |
| MO_1129 | APCS | p.G194D | 1 | 159558407 | G | A | NO | 4.4 | 0 | |
| MO_1129 | CES1 | p.S12A | 16 | 55866934 | A | C | NO | 3.2 | 0 | 1 |
| MO_1129 | PRDM11 | p.N201Y | 11 | 45226274 | A | T | YES | 2.2 | 0 | 0.02 |
| MO_1129 | USP37 | p.S968N | 2 | 219319690 | C | T | YES | 2.1 | 0 | 0.41 |
| MO_1129 | DMD | p.R1719H | X | 32381074 | C | T | NO | 1.2 | 0 | 0.05 |
| MO_1129 | HHATL | p.R186H | 3 | 42739770 | C | T | NO | 1.1 | 1 | 0 |
| MO_1129 | ODZ4 | p.L1229F | 11 | 78433828 | G | A | NO | 0.5 | 0 | 0 |
| MO_1129 | FAT4 | p.L1006I | 4 | 126240579 | C | A | NO | 0.5 | 0 | 0.19 |
| MO_1129 | ZFHX4 | p.L2551M | 8 | 77766808 | C | A | NO | 0.1 | 0 | 0.07 |
| MO_1129 | PABPC5 | p.R169Q | X | 90691082 | G | A | YES | 0.1 | 1 | 0.01 |
| MO_1129 | ODZ1 | p.S1848L | X | 123526026 | G | A | NO | 0.0 | 1 | 0.07 |
| MO_1129 | TMPRSS11F | splice donor | 4 | 68938039 | A | T | NO | 0.0 | 1 | |
| MO_1129 | OR2J3 | p.R175C | 6 | 29080190 | C | T | YES | 0.0 | 0 | 0.05 |
| MO_1129 | OR13C5 | p.T160I | 9 | 107361216 | G | A | NO | 0.0 | 0 | 0.05 |
| MO_1129 | OR1L4 | p.W140R | 9 | 125486686 | T | C | NO | 0.0 | 0 | 1 |
| MO_1167 | ESR1 | p.D538G | 6 | 152419926 | A | G | NA | 657.1 | 2 | 0 |
| MO_1167 | HLA-A | p.G199R | 6 | 29911296 | G | A | NA | 277.0 | 1 | 0 |
| MO_1167 | KIF1B | p.E1506K | 1 | 10425470 | G | A | NA | 24.5 | 0 | 0.08 |
| MO_1167 | DNMT3A | p.E408A | 2 | 25469545 | T | G | NA | 23.9 | 0 | 0.02 |
| MO_1167 | DNMT3A | p.E426D | 2 | 25469490 | T | G | NA | 23.9 | 0 | 0.13 |
| MO_1167 | RBMX | p.R324P | X | 135956506 | C | G | NA | 11.2 | 0 | 0.05 |
| MO_1167 | MLXIP | p.A518V | 12 | 122618355 | C | T | NA | 164.9 | 0 | 0.24 |
| MO_1167 | MACF1 | p.V1551G | 1 | 39796897 | T | G | NA | 141.4 | 0 | |
| MO_1167 | ATOX1 | splicing | 5 | 151138339 | G | A | NA | 138.2 | 0 | |
| MO_1167 | CTDSP1 | p.A69T | 2 | 219266424 | G | A | NA | 133.1 | 0 | 0.9 |
| MO_1167 | HISTAH3H | p.Q126X | 6 | 27778227 | C | T | NA | 61.8 | 0 | 0.01 |
| MO_1167 | RAPGEF5 | p.Y334N | 7 | 22200203 | A | T | NA | 48.0 | 0 | 0.24 |
| MO_1167 | MLLT4 | p.S1282F | 6 | 168351879 | C | T | NA | 43.6 | 0 | 0 |
| MO_1167 | MEF2A | p.Q428P | 15 | 100252738 | A | C | NA | 34.6 | 3 | 0.23 |
| MO_1167 | LHFPL2 | p.Y154H | 5 | 77784947 | A | G | NA | 25.2 | 0 | 0 |
| MO_1167 | EDEM3 | p.R253K | 1 | 184692980 | C | T | NA | 22.7 | 0 | 0.08 |
| MO_1167 | EIF2C4 | p.V154I | 1 | 36291067 | G | A | NA | 20.5 | 0 | 0.59 |
| MO_1167 | RP3-402G11.5. | UNKNOWN | 22 | 50639528 | T | C | NA | 18.3 | 0 | |
| MO_1167 | ZFP91 | p.C435F | 11 | 58384770 | G | T | NA | 18.1 | 0 | 0 |
| MO_1167 | NBAS | splicing | 2 | 15613473 | T | G | NA | 16.8 | 0 | |
| MO_1167 | NBAS | p.T548I | 2 | 15613428 | G | A | NA | 16.8 | 0 | 0.02 |
| MO_1167 | NBAS | p.E535D | 2 | 15613466 | T | G | NA | 16.8 | 0 | 0.77 |
| MO_1167 | ELL | p.R424H | 19 | 18561481 | C | T | NA | 12.9 | 0 | 0.3 |
| MO_1167 | KLHL26 | p.D237A | 19 | 18778917 | A | C | NA | 11.2 | 0 | 0.1 |
| MO_1167 | FDXR | p.P3L | 17 | 72869062 | G | A | NA | 9.6 | 0 | 0.1 |
| MO_1167 | SIRPA | p.G109S | 20 | 1895990 | G | A | NA | 6.7 | 0 | 1 |
| MO_1167 | SHROOM4 | p.P98S | X | 50381286 | G | A | NA | 6.0 | 0 | 0 |
| MO_1167 | SLC9A5 | p.L836H | 16 | 67304929 | G | A | NA | 5.6 | 0 | 0.19 |
| MO_1167 | UNC13D | p.R1065X | 19 | 73824126 | G | A | NA | 5.0 | 0 | 0.98 |
| MO_1167 | C22orf39 | p.R29G | 22 | 19435238 | G | C | NA | 2.6 | 0 | 0 |
| MO_1167 | ADRA1A | p.T391M | 8 | 26627895 | G | A | NA | 2.5 | 0 | 0 |
| MO_1167 | PLCE1 | p.R435K | 10 | 95892028 | G | A | NA | 2.5 | 0 | 0.18 |
| MO_1167 | ZFP91-CNTF | p.C435F | 11 | 58384770 | G | T | NA | 1.8 | 0 | 0 |
| MO_1167 | PCDHA10 | p.A426V | 5 | 140236910 | C | T | NA | 1.5 | 0 | 0.02 |
| MO_1167 | MUC4 | p.A3654T | 3 | 195507491 | C | T | NA | 1.4 | 0 | |
| MO_1167 | IGFN1 | p.G2022S | 1 | 201180085 | G | A | NA | 0.8 | 0 | |
| MO_1167 | ASPM | p.V2717L | 1 | 197070232 | C | G | NA | 0.8 | 0 | 0.04 |
| MO_1167 | BMP7 | p.D410E | 20 | 55746081 | A | T | NA | 0.7 | 0 | 0 |
| MO_1167 | B3GNT3 | p.A286T | 19 | 17922668 | G | A | NA | 0.3 | 1 | 0.05 |
| MO_1167 | DSG1 | p.G535R | 18 | 28919904 | G | A | NA | 0.1 | 0 | |
| MO_1167 | CTSE | p.R389H | 1 | 206331145 | G | A | NA | 0.1 | 0 | 0 |
| MO_1167 | COL17A1 | splicing | 10 | 106800822 | C | T | NA | 0.1 | 0 | |
| MO_1167 | IGHV4-31 | p.P28S | 14 | 106805481 | G | A | NA | 0 | 0 | 0.02 |
| MO_1167 | IGHV4-31 | p.V21L | 14 | 106805502 | G | C | NA | 0 | 0 | 0.42 |
| MO_1167 | AC012414.1 | p.T40K | 15 | 21071492 | G | T | NA | 0 | 0 | 1 |
| MO_1167 | GABRA6 | p.R48Q | 5 | 161113340 | G | A | NA | 0 | 1 | 0 |
| MO_1167 | ADAM2 | p.K349T | 8 | 39627077 | T | G | NA | 0 | 0 | 0 |
| MO_1167 | FCER2 | p.W167R | 19 | 7755414 | A | T | NA | 0 | 0 | |
| MO_1185 | ESR1 | p.Y537S | 6 | 152419923 | A | C | NA | 46.5 | 2 | 0 |
| MO_1185 | PTPRT | p.S846F | 20 | 40827900 | G | A | NA | 13.6 | 0 | 1 |
| MO_1185 | CDH1 | p.S70F | 16 | 68835618 | C | T | NA | 9.4 | 0 | 0 |
| MO_1185 | CDH1 | p.Q641X | 16 | 68856113 | C | T | NA | 9.4 | 0 | 0.24 |
| MO_1185 | LRP1B | p.P3139T | 2 | 141242922 | G | T | NA | 8.3 | 0 | 0.31 |
| MO_1185 | FGFR1 | p.R840Q | 8 | 38271189 | C | T | NA | 5.9 | 0 | 0.6 |
| MO_1185 | TERT | p.V1035I | 5 | 1255456 | C | T | NA | 0.1 | 0 | 0.57 |

TABLE 3-continued

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1185 | ALK | p.E1299K | 2 | 29430080 | C | T | NA | 0.0 | 1 | 0 |
| MO_1185 | MUC5B | p.S1632L | 11 | 1262996 | C | T | NA | 1131.5 | 0 | |
| MO_1185 | VIM | p.E134K | 10 | 17271821 | G | A | NA | 603.8 | 0 | 0 |
| MO_1185 | HNRNPK | p.L68F | 9 | 86591921 | G | A | NA | 292.6 | 0 | 0.03 |
| MO_1185 | EIF5A | p.Y157C | 17 | 7214778 | A | G | NA | 135.4 | 0 | 0 |
| MO_1185 | HNRNPU | p.S4L | 1 | 245027599 | G | A | NA | 122.4 | 0 | 0 |
| MO_1185 | SCCPDH | p.S84L | 1 | 246890254 | C | T | NA | 98.6 | 2 | 0 |
| MO_1185 | TXNIP | p.E165K | 1 | 145440059 | G | A | NA | 79.5 | 0 | 0 |
| MO_1185 | INF2 | p.E58K | 14 | 105167874 | G | A | NA | 72.3 | 0 | 0.07 |
| MO_1185 | AHNAK | p.P2833A | 11 | 62293392 | G | C | NA | 64.9 | 0 | 0.07 |
| MO_1185 | ALYREF | p.R151C | 17 | 79847145 | G | A | NA | 50.1 | 0 | 0 |
| MO_1185 | RERE | p.S1084A | 1 | 8420317 | A | C | NA | 40.3 | 0 | 0.32 |
| MO_1185 | MEPCE | p.Q137X | 7 | 100028050 | C | T | NA | 38.9 | 0 | 0.22 |
| MO_1185 | SSSCA1 | p.S165Y | 11 | 65339099 | C | A | NA | 32.2 | 0 | 0 |
| MO_1185 | TBCD | p.P1143T | 17 | 80895956 | G | A | NA | 30.6 | 0 | 0.06 |
| MO_1185 | STX16 | p.D199N | 20 | 57245606 | G | A | NA | 30.1 | 0 | 0.01 |
| MO_1185 | AGPAT6 | P.Q278X | 8 | 41470400 | C | T | NA | 27.2 | 0 | 0 |
| MO_1185 | RBM25 | p.R433Q | 14 | 73572710 | G | A | NA | 26.6 | 0 | 0.42 |
| MO_1185 | MUC16 | p.R12975W | 19 | 9010995 | G | A | NA | 24.6 | 0 | 0.01 |
| MO_1185 | ZFAND2B | p.Q41X | 2 | 220072114 | C | T | NA | 20.6 | 0 | 0.15 |
| MO_1185 | PRKAA1 | p.R144H | 5 | 40771943 | C | T | NA | 19.8 | 0 | 0 |
| MO_1185 | ITGAV | p.T76P | 2 | 187466788 | A | C | NA | 19.7 | 0 | 0 |
| MO_1185 | NFKBIZ | p.M376I | 3 | 101572498 | G | A | NA | 19.2 | 0 | 0.03 |
| MO_1185 | NOP14 | splicing | 4 | 2958396 | C | A | NA | 19.1 | 0 | |
| MO_1185 | AP3B1 | p.S31L | 5 | 77590312 | G | A | NA | 18.2 | 1 | 0.03 |
| MO_1185 | SNTB1 | p.G224D | 8 | 121706049 | C | T | NA | 17.2 | 0 | 0.04 |
| MO_1185 | GGPS1 | p.P210K | 1 | 235505812 | G | A | NA | 16.1 | 0 | 0 |
| MO_1185 | SLC2A11 | p.P203L | 22 | 24219643 | C | T | NA | 14.4 | 0 | 0 |
| MO_1185 | KIAA0020 | p.E353K | 9 | 2824794 | C | T | NA | 12.7 | 0 | |
| MO_1185 | RBBP6 | p.A595T | 16 | 24578657 | G | A | NA | 12.3 | 0 | 0.07 |
| MO_1185 | TMEM135 | p.R421X | 11 | 87032259 | C | T | NA | 12.2 | 1 | 1 |
| MO_1185 | STX18 | p.T18M | 4 | 4543639 | G | A | NA | 11.3 | 0 | 0.02 |
| MO_1185 | SBNO1 | p.M208I | 12 | 123825562 | C | T | NA | 10.7 | 0 | 0.87 |
| MO_1185 | NCF2 | p.R38L | 1 | 183559352 | C | A | NA | 10.2 | 0 | 0 |
| MO_1185 | ZNHIT2 | p.Q366P | 11 | 64884029 | T | G | NA | 9.6 | 0 | 0.01 |
| MO_1185 | EMR2 | p.K154I | 19 | 14877816 | T | A | NA | 8.4 | 0 | 0.22 |
| MO_1185 | SIRT6 | p.R150X | 19 | 4175924 | G | A | NA | 7.6 | 0 | 1 |
| MO_1185 | PASK | p.V1217G | 2 | 242047620 | A | C | NA | 7.3 | 0 | 0 |
| MO_1185 | TRIM32 | p.P431T | 9 | 119461312 | C | A | NA | 6.7 | 0 | 0 |
| MO_1185 | CENPF | p.S1477X | 1 | 214816111 | C | A | NA | 8.5 | 0 | |
| MO_1185 | PLEKHG2 | p.S663F | 19 | 39913682 | C | T | NA | 5.6 | 0 | 0 |
| MO_1185 | ATP2B1 | p.E1136K | 12 | 89985018 | C | T | NA | 4.1 | 0 | 0.12 |
| MO_1185 | FKTN | p.E456K | 9 | 108397525 | G | A | NA | 3.7 | 0 | 0.05 |
| MO_1185 | PCDHGB4 | p.L212F | 5 | 140768087 | G | C | NA | 3.2 | 0 | |
| MO_1185 | WDFY4 | p.F820I | 10 | 49951565 | T | A | NA | 2.9 | 0 | 0.39 |
| MO_1185 | ZNF528 | p.S144L | 19 | 52918536 | C | T | NA | 2.9 | 0 | 1 |
| MO_1185 | KLF8 | p.D65N | X | 56291724 | G | A | NA | 2.2 | 0 | 0.43 |
| MO_1185 | STX16-NPEPL1 | p.D199N | 20 | 57245606 | G | A | NA | 2.0 | 0 | 0.01 |
| MO_1185 | EVX1 | p.Y317S | 7 | 27285770 | A | C | NA | 2.0 | 0 | |
| MO_1185 | AMPH | p.E459K | 7 | 38457448 | C | T | NA | 1.8 | 0 | 0.05 |
| MO_1185 | CCDC40 | p.E991K | 17 | 78064076 | G | A | NA | 1.4 | 0 | 0.04 |
| MO_1185 | CCDC40 | p.R980Q | 17 | 78064044 | C | T | NA | 1.4 | 0 | 0 |
| MO_1185 | SVEP1 | p.S1470F | 9 | 113208171 | G | A | NA | 1.3 | 0 | 0 |
| MO_1185 | PPFIA3 | p.K1132N | 19 | 49652845 | G | C | NA | 1.1 | 0 | 0 |
| MO_1185 | HOXO3 | p.R422X | 2 | 177036967 | C | T | NA | 1.0 | 0 | 1 |
| MO_1185 | DNAH10 | p.A1831T | 12 | 124332538 | G | A | NA | 0.9 | 0 | 0 |
| MO_1185 | SPTB | p.E171K | 14 | 65268999 | C | T | NA | 0.9 | 0 | 0 |
| MO_1185 | ZNF208 | p.L34F | 19 | 22171613 | T | G | NA | 0.5 | 0 | 0 |
| MO_1185 | KIRREL | p.E460Q | 1 | 158061205 | G | C | NA | 0.4 | 0 | 0.15 |
| MO_1185 | RIMS1 | p.E1471Q | 6 | 73100344 | G | C | NA | 0.3 | 0 | 0 |
| MO_1185 | OR4C3 | p.W174X | 11 | 48347014 | G | A | NA | 0.1 | 0 | |
| MO_1185 | NR6A1 | p.S17L | 9 | 127533349 | G | A | NA | 0.1 | 0 | 0 |
| MO_1185 | LAMA1 | p.K247N | 18 | 7049104 | T | A | NA | 0.1 | 0 | |
| MO_1185 | KCNN3 | p.C519W | 1 | 154705512 | A | C | NA | 0.1 | 0 | 0 |
| MO_1185 | HRNR | p.R2466H | 1 | 152186708 | C | T | NA | 0.0 | 0 | 0.59 |
| MO_1185 | KRT6C | p.S227N | 12 | 52865925 | C | T | NA | 0.0 | 0 | 0.26 |
| MO_1185 | IRX1 | p.G300S | 5 | 3599960 | G | A | NA | 0.0 | 0 | 0.38 |
| MO_1185 | PRH2 | p.R119C | 12 | 11083515 | C | T | NA | 0.0 | 0 | 0.07 |
| MO_1185 | LVRN.1 | p.H813Y | 5 | 115350211 | C | T | NA | 0.0 | 0 | 0.05 |
| MO_1185 | ALPK2 | p.E144K | 18 | 56203089 | C | T | NA | 0.0 | 0 | 0 |
| MO_1185 | UNC79 | p.D496N | 14 | 94007139 | G | A | NA | 0.0 | 0 | 0 |
| MO_1185 | UNC80 | p.Q1837H | 2 | 210791613 | G | C | NA | 0.0 | 0 | 0.34 |
| MO_1185 | GRIK3 | p.E852Q | 1 | 37270599 | C | G | NA | 0.0 | 0 | 0.58 |
| MO_1185 | TGM6 | p.E408K | 20 | 2384355 | G | A | NA | 0.0 | 0 | 1 |
| MO_1185 | HRG | p.D170N | 3 | 186389528 | G | A | NA | 0.0 | 0 | 0.69 |
| MO_1185 | GDA | p.D155N | 9 | 74825681 | G | A | NA | 0.0 | 0 | 0.01 |
| MO_1185 | OR10H1 | p.E173D | 19 | 15918329 | C | A | NA | 0.0 | 0 | 0.58 |

TABLE 3-continued

| Case ID | Gene | Amino Acid Change | Chr | Coord | Ref | Var | Present in FFPE | Expression (FPKM) | COSMIC @ Pos | AVISIFT Score |
|---|---|---|---|---|---|---|---|---|---|---|
| MO_1185 | ZNF454 | p.S398C | 5 | 178392598 | C | G | NA | 0.0 | 0 | 0.04 |
| MO_1185 | OR2T27 | p.Y120C | 1 | 248813827 | T | C | NA | 0.0 | 0 | 0.02 |
| MO_1185 | IGHV4-31 | p.V21L | 14 | 106805502 | C | G | NA | 0.0 | 0 | 0.42 |
| MO_1185 | IGHV4-31 | p.P28S | 14 | 106805481 | G | A | NA | 0.0 | 0 | 0.02 |

TABLE 4

| Case ID | Chr | Loc Start | Loc End | # Exon Targets | Adj Copy Num Ratio | MiOncoSeq Panel Genes |
|---|---|---|---|---|---|---|
| MO_1031 | 4 | 68,588,132 | 68,829,154 | 24 | 10.35 | |
| MO_1031 | 10 | 17,130,256 | 17,432,516 | 45 | 8.28 | |
| MO_1031 | 10 | 81,316,935 | 84,498,366 | 95 | 8.26 | NRG3 |
| MO_1031 | 11 | 92,881,858 | 92,931,012 | 11 | 7.77 | |
| MO_1031 | 4 | 68,919,654 | 69,107,468 | 22 | 7.59 | |
| MO_1031 | 8 | 33,230,180 | 32,251,814 | 3 | 7.50 | |
| MO_1031 | 10 | 74,451,906 | 75,530,518 | 186 | 7.17 | |
| MO_1031 | 10 | 76,154,035 | 77,312,230 | 59 | 6.79 | KAT6B |
| MO_1031 | 11 | 69,456,232 | 70,196,120 | 71 | 6.75 | CCND1, FADD, FGF19, FGF3, FGF4 |
| MO_1031 | 8 | 35,401,916 | 38,599,900 | 236 | 6.74 | BAG4, FGFR1, GPR124, LSM1, WHSC1L1, ZNF703 |
| MO_1031 | 10 | 12,802,948 | 13,568,184 | 72 | 6.69 | |
| MO_1031 | 10 | 11,551,638 | 12,272,906 | 88 | 6.57 | |
| MO_1031 | 18 | 6,171,882 | 6,263,988 | 9 | 6.46 | |
| MO_1031 | 10 | 123,233,969 | 123,629,536 | 27 | 6.32 | FGFR2 |
| MO_1031 | 4 | 69,111,386 | 69,215,570 | 15 | 5.81 | |
| MO_1031 | 4 | 66,189,850 | 67,142,530 | 19 | 5.51 | EPHA5 |
| MO_1031 | 10 | 75,532,834 | 76,074,464 | 88 | 5.15 | |
| MO_1031 | 10 | 77,542,720 | 81,266,457 | 158 | 5.13 | |
| MO_1031 | 8 | 39,442,183 | 41,164,370 | 74 | 4.72 | |
| MO_1031 | 8 | 38,602,921 | 39,142,362 | 94 | 4.76 | |
| MO_1031 | 11 | 90,288,976 | 92,718,066 | 35 | 4.61 | |
| MO_1031 | 3 | 87,275,319 | 88,205,533 | 26 | 4.11 | |
| MO_1031 | 18 | 2,539,035 | 6,138,182 | 201 | 4.03 | |
| MO_1031 | 10 | 11,505,120 | 11,543,156 | 8 | 3.99 | |
| MO_1031 | 12 | 3,982,470 | 4,481,740 | 14 | 3.94 | CCND2, FGF23 |
| MO_1031 | 18 | 6,301,996 | 11,825,000 | 294 | 3.92 | |
| MO_1031 | 12 | 13,093,751 | 13,154,594 | 9 | 3.86 | |
| MO_1031 | 10 | 17,495,666 | 17,686,317 | 7 | 3.75 | |
| MO_1031 | 16 | 70,526,211 | 71,442,070 | 6 | 3.36 | |
| MO_1031 | 10 | 12,277,132 | 12,767,372 | 12 | 3.23 | |
| MO_1031 | 8 | 33,310,878 | 35,093,272 | 29 | 3.19 | |
| MO_1031 | 18 | 61,747,550 | 66,368,940 | 38 | 3.15 | |
| MO_1031 | 12 | 21,919,132 | 22,837,826 | 94 | 3.09 | |
| MO_1031 | 11 | 70,200,412 | 71,850,892 | 187 | 3.06 | |
| MO_1031 | 11 | 76,706,811 | 77,825,721 | 158 | 3.03 | PAK1 |
| MO_1031 | 12 | 208,418 | 1,769,452 | 175 | 2.89 | KDM5A, WNT5B |
| MO_1031 | 12 | 4,488,584 | 5,154,919 | 75 | 2.88 | FGF23, FGF6 |
| MO_1031 | 11 | 78,497,956 | 79,113,172 | 14 | 2.70 | |
| MO_1031 | 18 | 11,851,800 | 15,004,215 | 220 | 2.70 | |
| MO_1031 | 4 | 54,853,144 | 54,967,958 | 7 | 2.67 | CHIC2 |
| MO_1031 | 17 | 51,901,464 | 81,083,588 | 3437 | 2.61 | AATK, AXIN2, BIRC5, BRIP1, CD79B, GRB2, HLF, PPM1D, PRKAR1A, RAD51C, RNF213, RNF43, RPS6KB1, RPTOR, SRSF2, TMC6, TMC8 |
| MO_1031 | 18 | 158,542 | 1,358,660 | 93 | 2.58 | YES1 |
| MO_1031 | 11 | 67,864,607 | 68,031,182 | 17 | 2.54 | |
| MO_1031 | 4 | 73,927,524 | 74,735,596 | 110 | 2.49 | |
| MO_1031 | 1 | 201,755,699 | 201,817,549 | 24 | 2.49 | |
| MO_1031 | 12 | 21,201,680 | 21,807,605 | 97 | 2.42 | |
| MO_1031 | 18 | 61,471,724 | 61,654,338 | 25 | 2.42 | |
| MO_1031 | 1 | 207,245,672 | 208,390,788 | 139 | 2.41 | |
| MO_1031 | 4 | 68,202,157 | 88,547,886 | 82 | 2.38 | |
| MO_1031 | 11 | 72,945,843 | 74,209,014 | 177 | 2.37 | |
| MO_1031 | 11 | 28,080,588 | 36,123,407 | 438 | 2.35 | EHF, ELF5, LMO2, WT1 |
| MO_1031 | 3 | 85,755,692 | 87,100,805 | 15 | 2.34 | CADM2 |
| MO_1031 | 8 | 32,406,234 | 32,621,669 | 18 | 2.31 | NRG1 |
| MO_1031 | 11 | 9,983,601 | 10,875,419 | 102 | 2.25 | |
| MO_1031 | 4 | 75,065,608 | 75,959,197 | 24 | 2.24 | AREG, BTC, EPGN, EREG |
| MO_1031 | 11 | 71,903,301 | 72,342,154 | 66 | 2.24 | |
| MO_1031 | 11 | 74,907,638 | 74,915,575 | 5 | 2.24 | |
| MO_1031 | 8 | 146,115,084 | 146,279,458 | 14 | 2.22 | |
| MO_1031 | 11 | 96,074,868 | 99,426,930 | 10 | 2.22 | MAML2 |
| MO_1031 | 4 | 69,313,202 | 70,826,694 | 84 | 1.99 | |

TABLE 4-continued

| Case ID | Chr | Loc Start | Loc End | # Exon Targets | Adj Copy Num Ratio | MiOncoSeq Panel Genes |
|---|---|---|---|---|---|---|
| MO_1031 | 1 | 190,067,665 | 193,218,926 | 72 | 1.99 | CDC73 |
| MO_1031 | 12 | 13,197,380 | 21,176,141 | 359 | 1.88 | PIK3C2G |
| MO_1031 | 18 | 59,894,692 | 61,468,169 | 142 | 1.87 | BCL2, KDSR |
| MO_1031 | 18 | 66,377,286 | 70,502,474 | 86 | 1.87 | |
| MO_1031 | 4 | 72,607,550 | 73,923,894 | 43 | 1.85 | |
| MO_1031 | 11 | 22,214,994 | 28,078,414 | 156 | 1.84 | BDNF, FANCF |
| MO_1031 | 12 | 23,688,112 | 26,985,695 | 156 | 1.82 | KRAS |
| MO_1031 | 8 | 66,617,076 | 141,931,000 | 2986 | 1.81 | EXT1, HEY1, MTDH, MYBL1, MYC, NBN, NCOA2, PREX2, PTK2, PVT1, RSPO2, RUNX1T1, STK3, TRIB1, YWHAZ, ZNF704 |
| MO_1031 | 16 | 29,820,892 | 29,842,221 | 10 | 1.81 | |
| MO_1031 | 4 | 52,709,311 | 54,442,468 | 99 | 1.80 | |
| MO_1031 | 1 | 172,108,064 | 184,537,648 | 925 | 1.80 | ABL2, FASLG |
| MO_1031 | 1 | 206,903,313 | 207,244,824 | 72 | 1.80 | |
| MO_1031 | 1 | 201,821,210 | 201,865,775 | 25 | 1.79 | |
| MO_1031 | 19 | 58,904,864 | 59,083,890 | 56 | 1.77 | |
| MO_1031 | 3 | 27,152,740 | 32,612,234 | 204 | 1.77 | TGFBR2 |
| MO_1031 | 14 | 50,044,532 | 56,150,882 | 590 | 1.75 | CDKN3 |
| MO_1031 | 12 | 133,728,390 | 133,770,132 | 7 | 1.75 | |
| MO_1031 | 11 | 75,708,074 | 76,701,540 | 86 | 1.73 | C11orf30, WNT11 |
| MO_1031 | 10 | 84,625,118 | 86,273,618 | 61 | 1.72 | NRG3 |
| MO_1031 | 12 | 5,541,438 | 13,068,862 | 1014 | 1.71 | CDKN1B, ETV6, ING4, LRP6, NTF3, STYK1, ZNF384 |
| MO_1031 | 1 | 209,602,742 | 210,856,990 | 100 | 1.71 | IRF6 |
| MO_1031 | 4 | 55,106,349 | 56,225,649 | 71 | 1.70 | KDR, KIT, PDGFRA |
| MO_1031 | 16 | 31,804,064 | 31,895,792 | 5 | 1.69 | |
| MO_1031 | 12 | 57,111,463 | 57,118,361 | 4 | 1.68 | |
| MO_1031 | 17 | 38,487,509 | 40,105,473 | 356 | 1.68 | RARA, TOP2A |
| MO_1031 | 15 | 60,715,773 | 102,389,505 | 3226 | 1.66 | BCL2A1, BLM, CRTC3, CSK, FANCI, FES, IDH2, IGF1R, IQGAP1, MAP2K1, NRG4, NTRK3, PML, SMAD3, SMAD6 |
| MO_1031 | 1 | 204,915,769 | 205,760,704 | 151 | 1.62 | ELK4 |
| MO_1031 | 3 | 12,810,669 | 19,295,220 | 467 | 1.62 | WNT7A, XPC |
| MO_1031 | 12 | 1,863,550 | 3,949,766 | 224 | 1.62 | FOXM1 |
| MO_1031 | 20 | 68,356 | 62,904,843 | 4648 | 1.58 | ARFRP1, ASXL1, AURKA, BCL2L1, CEBPB, GNAS, HCK, MAFB, MYBL2, NCCA3, NFATC2, PAK7, PLCG1, PTK6, PTPRT, SRC, SRMS, STK4, TOP1, YWHAB, ZMYND8, ZNF217 |
| MO_1031 | 7 | 154,237,588 | 158,937,252 | 313 | 1.57 | MNX1, SHH |
| MO_1031 | 14 | 22,356,506 | 22,963,536 | 83 | 1.53 | |
| MO_1031 | 3 | 84,962,992 | 85,156,657 | 3 | 1.49 | CADM2 |
| MO_1031 | 17 | 25,621,074 | 25,628,926 | 3 | 1.48 | |
| MO_1031 | 16 | 29,808,376 | 29,819,978 | 11 | 1.47 | |
| MO_1031 | 17 | 20,639,138 | 22,023,536 | 51 | -0.07 | |
| MO_1031 | 21 | 9,825,990 | 9,826,257 | 2 | -0.02 | |
| MO_1031 | 8 | 2,796,151 | 3,611,511 | 66 | 0.00 | |
| MO_1031 | 22 | 39,360,598 | 39,385,480 | 6 | 0.04 | |
| MO_1031 | 14 | 26,917,625 | 27,377,958 | 7 | 0.11 | |
| MO_1031 | 5 | 177,186,120 | 177,302,765 | 3 | 0.20 | |
| MO_1031 | 1 | 211,832,141 | 211,847,090 | 6 | 0.24 | |
| MO_1031 | 10 | 46,961,903 | 47,087,312 | 11 | 0.27 | |
| MO_1031 | 10 | 135,077,162 | 135,123,783 | 35 | 0.30 | |
| MO_1031 | 10 | 133,918,368 | 135,044,448 | 183 | 0.36 | |
| MO_1031 | 11 | 636,612 | 1,282,788 | 251 | 0.36 | |
| MO_1031 | 2 | 105,472,458 | 105,488,778 | 4 | 0.39 | |
| MO_1031 | 3 | 20,218,127 | 23,312,464 | 14 | 0.42 | |
| MO_1031 | 12 | 132,911,966 | 133,032,417 | 5 | 0.42 | |
| MO_1031 | 11 | 193,171 | 534,238 | 107 | 0.43 | HRAS |
| MO_1031 | 4 | 7,533,339 | 10,118,369 | 180 | 0.43 | |
| MO_1031 | 16 | 82,660,648 | 90,133,269 | 754 | 0.43 | FANCA, MC1R |
| MO_1031 | 8 | 183,094 | 2,148,837 | 11 | 0.44 | |
| MO_1031 | 4 | 3,076,537 | 3,534,082 | 114 | 0.47 | |
| MO_1031 | 11 | 63,276,172 | 64,836,076 | 405 | 0.47 | ESRRA, MEN1, VEGFB |
| MO_1031 | 10 | 135,125,386 | 135,381,649 | 77 | 0.48 | |
| MO_1031 | 6 | 31,865,505 | 31,867,955 | 3 | 0.48 | |
| MO_1031 | 5 | 177,419,839 | 180,687,459 | 418 | 0.50 | FLT4, MAML1, NHP2 |
| MO_1031 | 11 | 55,433,136 | 57,480,180 | 182 | 0.51 | |
| MO_1031 | 12 | 100,451,433 | 100,463,882 | 4 | 0.52 | |
| MO_1031 | 10 | 255,897 | 9,450,260 | 491 | 0.53 | GATA3, KLF6 |
| MO_1031 | 18 | 71,740,798 | 78,005,236 | 223 | 0.53 | |
| MO_1031 | 11 | 49,059,002 | 55,340,015 | 39 | 0.53 | |
| MO_1031 | 10 | 123,658,413 | 133,795,411 | 542 | 0.53 | |

TABLE 4-continued

| Case ID | Chr | Loc Start | Loc End | # Exon Targets | Adj Copy Num Ratio | MiOncoSeq Panel Genes |
|---|---|---|---|---|---|---|
| MO_1031 | 17 | 6,108 | 20,492,914 | 2733 | 0.53 | ALOX12B, AURKB, C17orf39, COPS3, CRK, DVL2, FGF11, FLCN, GPS2, MAP2K4, NCOR1, RABEP1, RPA1, TNK1, TP53, USP6 |
| MO_1031 | 16 | 34,257,075 | 62,055,226 | 1163 | 0.54 | C16orf57, CYLD, NUP93 |
| MO_1031 | 11 | 2,154,292 | 9,229,136 | 832 | 0.54 | CDKN1C, IGF2, LMO1, NUP98, RBMXL2, RRM1 |
| MO_1031 | 6 | 154,727,562 | 170,893,472 | 890 | 0.55 | ARID1B, IGF2R, PARK2, TBP |
| MO_1031 | 3 | 37,308,321 | 66,550,768 | 3147 | 0.55 | ALAS1, BAP1, CTNNB1, FHIT, MAP4, MST1, MST1R, MYD88, PBRM1, PTPRG, SETD2, WNT5A |
| MO_1031 | 3 | 4,817,048 | 12,791,326 | 579 | 0.55 | FANCD2, PPARG, RAF1, VHL |
| MO_1031 | 8 | 41,166,434 | 43,212,028 | 260 | 0.55 | IKBKB, KAT6A |
| MO_1031 | 17 | 26,488,181 | 34,207,360 | 973 | 0.55 | NF1, RAD51D, RHOT1, SUZ12, TAF15 |
| MO_1031 | 1 | 205,859,650 | 206,331,182 | 33 | 0.57 | |
| MO_1031 | 10 | 48,371,062 | 74,326,404 | 1228 | 0.58 | NCOA4, PRF1 |
| MO_1031 | 9 | 71,986,384 | 101,817,485 | 1617 | 0.58 | FANCC, GALNT12, GNAQ, NTRK2, PTCH1, ROR2, SYK, XPA |
| MO_1031 | 8 | 3,855,468 | 31,497,817 | 1532 | 0.58 | BLK, FGF17, FGF20, NKX3-1, NRG1, PTK2B, TNKS, WRN |
| MO_1031 | 11 | 13,391,238 | 21,596,574 | 669 | 0.58 | |
| MO_1031 | 1 | 211,847,711 | 233,105,699 | 1448 | 0.59 | H3F3A, PSEN2, WNT3A, WNT9A |
| MO_1031 | 10 | 13,629,072 | 17,127,612 | 236 | 0.59 | |
| MO_1031 | 11 | 93,065,442 | 93,148,321 | 14 | 0.59 | |
| MO_1031 | 11 | 93,428,784 | 94,597,928 | 135 | 0.59 | MRE11A |
| MO_1031 | 10 | 104,809,500 | 122,688,216 | 1135 | 0.59 | SHOC2, TCF7L2 |
| MO_1031 | 11 | 99,429,012 | 134,257,653 | 2837 | 0.59 | ATM, BIRC2, BIRC3, CBL, CHEK1, DDX6, ETS1, FLI1, GUCY1A2, HMBS, MLL, PDGFD, POU2AF1, SDHD, UBE4A, YAP1, ZBTB16 |
| MO_1031 | 15 | 29,346,459 | 60,690,024 | 2861 | 0.59 | BUB1B, FGF7, LTK, NOP10, RAD51, SPRED1, TYRO3 |
| MO_1031 | 5 | 138,611,754 | 138,860,952 | 58 | 0.59 | |
| MO_1031 | 14 | 56,585,346 | 82,000,118 | 1909 | 0.59 | C14orf133, ESR2, FOS, HIF1A, HIF1A, MAX, MLH3, NUMB, PGF, PSEN1, TSHR |
| MO_1031 | 5 | 135,277,073 | 136,328,170 | 48 | 0.59 | SMAD5 |
| MO_1031 | 10 | 88,718,542 | 104,680,474 | 1742 | 0.60 | BLNK, CHUK, CYP17A1, FAS, FGF8, GOT1, LDB1, NFKB2, PTEN, SUFU, TLX1, TNKS2, WNT8B |
| MO_1031 | 1 | 234,350,230 | 240,656,524 | 462 | 0.60 | |
| MO_1031 | 11 | 77,830,326 | 78,489,599 | 57 | 0.60 | GAB2 |
| MO_1031 | 4 | 61,788,424 | 65,275,026 | 44 | 0.60 | LPHN3 |
| MO_1031 | X | 2,700,167 | 102,755,742 | 3800 | 0.61 | AR, ARAF, ATRX, BCOR, BMX, BTK, CCNB3, DDX3X, ELK1, FAM123B, FANCB, FGF16, FIGF, FOXO4, FOXP3, GATA1, KDM5C, KDM6A, MAGED1, MED12, PIM2, SSX1, SSX2, SSX3, SSX4, TBX22, TFE3, USP9X, WAS, ZRSR2 |
| MO_1031 | 10 | 17,702,514 | 46,222,766 | 1080 | 0.61 | MLLT10, RET |
| MO_1031 | 5 | 125,696,010 | 134,106,614 | 636 | 0.61 | ACSL6, IL3, RAD50, TCF7 |
| MO_1031 | 6 | 151,144,864 | 151,939,184 | 68 | 0.61 | |
| MO_1031 | 9 | 3,453,732 | 26,101,343 | 768 | 0.61 | CDKN2A, CDKN2B, JAK2, NFIB, PSIP1, PTPRD |
| MO_1031 | 18 | 18,539,877 | 58,309,304 | 1673 | 0.61 | ASXL3, CDH2, GATA6, MALT1, MBD1, PIK3C3, ROCK1, SMAD2, SMAD4, SMAD7, SS18 |
| MO_1031 | 3 | 239,492 | 4,558,246 | 119 | 0.62 | CRBN |
| MO_1031 | 4 | 165,876,302 | 190,903,876 | 826 | 0.62 | VEGFC |
| MO_1031 | 3 | 67,546,367 | 81,810,649 | 304 | 0.62 | FOXP1, MITF, ROBO2 |
| MO_1031 | 1 | 211,526,618 | 211,751,637 | 16 | 0.63 | |
| MO_1031 | 6 | 37,180,450 | 124,442,998 | 4130 | 0.63 | BACH2, BAI3, CCND3, EPHA7, FOXO3, FOXP4, FRK, FYN, PKHD1, PNRC1, PRDM1, PTK7, RAB23, ROS1, TFEB, VEGFA |
| MO_1031 | 6 | 142,399,794 | 145,823,742 | 193 | 0.63 | PLAGL1 |
| MO_1031 | 14 | 20,201,656 | 20,404,300 | 15 | 0.63 | |
| MO_1031 | 9 | 71,080,062 | 71,152,243 | 7 | 0.64 | |
| MO_1031 | 4 | 25,758,416 | 43,032,450 | 578 | 0.64 | PHOX2B, RBPJ, RHOH |
| MO_1031 | 3 | 32,726,898 | 37,190,419 | 251 | 0.64 | MLH1 |
| MO_1031 | 6 | 126,176,264 | 137,245,469 | 685 | 0.64 | MAP3K5, MYB, PTPRK, RSPO3 |
| MO_1031 | 2 | 154,334,924 | 201,305,468 | 2736 | 0.64 | HNRNPA3, HOXD11, HOXD13, HOXD4, NAB1, NFE2L2, PDK1, PMS1, SF3B1, SP3, STAT1, STAT4 |
| MO_1031 | 5 | 54,415,758 | 122,522,926 | 2765 | 0.64 | APC, FER, IQGAP2, MAP3K1, PIK3R1 |
| MO_1031 | 11 | 81,601,827 | 89,955,936 | 333 | 0.65 | PICALM |

TABLE 4-continued

| Case ID | Chr | Loc Start | Loc End | # Exon Targets | Adj Copy Num Ratio | MiOncoSeq Panel Genes |
|---|---|---|---|---|---|---|
| MO_1031 | 3 | 19,322,754 | 20,216,137 | 64 | 0.65 | |
| MO_1031 | 4 | 74,647,007 | 75,046,416 | 16 | 0.66 | |
| MO_1031 | 4 | 10,446,372 | 15,560,868 | 105 | 0.66 | |
| MO_1031 | 1 | 85,869,998 | 93,913,780 | 539 | 0.66 | GFI1, RBMXL1 |
| MO_1031 | 14 | 28,733,801 | 31,056,040 | 27 | 0.66 | |
| MO_1031 | 4 | 81,256,954 | 110,650,894 | 1362 | 0.66 | AFF1, FGF5, LEF1, NFKB1, RAP1GDS1, TET2 |
| MO_1031 | 14 | 39,818,203 | 48,230,312 | 133 | 0.67 | FANCM |
| MO_1031 | 4 | 44,682,652 | 44,719,222 | 19 | 0.68 | |
| MO_1031 | 3 | 23,364,968 | 26,751,572 | 97 | 0.69 | TOP2B |
| MO_1031 | 22 | 23,610,702 | 23,632,514 | 10 | 0.69 | BCR |
| MO_1031 | 6 | 34,741,320 | 34,840,216 | 21 | 0.70 | |
| MO_1051 | 1 | 152,484,088 | 152,816,125 | 19 | 3.31 | |
| MO_1051 | 11 | 6,231,424 | 6,232,842 | 3 | 2.92 | |
| MO_1051 | 20 | 61,438,941 | 61,468,452 | 32 | 2.42 | |
| MO_1051 | 1 | 248,604,538 | 249,211,679 | 25 | 2.30 | |
| MO_1051 | X | 34,148,550 | 34,962,044 | 10 | 2.14 | |
| MO_1051 | X | 107,404,842 | 107,936,036 | 88 | 2.07 | |
| MO_1051 | 1 | 152,657,076 | 227,843,507 | 6285 | 2.01 | ABL2, CDC73, CKS1B, DDR2, ELF3, ELK4, ETV3, ETV3L, FASLG, H3F3A, HAX1, IKBKE, INSRR, IQGAP3, IRF6, MDM4, NCSTN, NTRK1, PBX1, PBX1, PRRX1, PSEN2, RAB25, SDHC, SHC1 |
| MO_1051 | X | 31,792,194 | 32,235,103 | 8 | 1.98 | |
| MO_1051 | 15 | 25,416,022 | 25,496,149 | 41 | 1.95 | |
| MO_1051 | 1 | 144,013,934 | 152,081,884 | 754 | 1.94 | APH1A, ARNT, BCL9, CHD1L, MCL1 |
| MO_1051 | 12 | 54,369,140 | 54,520,236 | 16 | 1.93 | HOXC11 |
| MO_1051 | 1 | 229,407,014 | 247,611,745 | 1149 | 1.91 | AKT3, FH |
| MO_1051 | 17 | 46,607,082 | 46,709,920 | 23 | 1.89 | |
| MO_1051 | X | 95,940,052 | 96,639,008 | 27 | 1.81 | |
| MO_1051 | 4 | 53,298 | 67,754 | 4 | 1.74 | |
| MO_1051 | 7 | 27,140,656 | 27,282,803 | 28 | 1.71 | HOXA10, HOXA11, HOXA13, HOXA3, HOXA9 |
| MO_1051 | 19 | 35,803,193 | 36,018,323 | 39 | 1.70 | CD22 |
| MO_1051 | 19 | 10,077,158 | 10,108,796 | 30 | 1.70 | |
| MO_1051 | 19 | 36,054,320 | 36,556,852 | 179 | 1.65 | ETV2, PSENEN |
| MO_1051 | 19 | 45,910,365 | 46,029,258 | 32 | 1.69 | ERCC1, FOSB |
| MO_1051 | 1 | 152,083,634 | 152,287,808 | 27 | 1.54 | |
| MO_1051 | 2 | 228,135,522 | 228,163,484 | 20 | 1.53 | |
| MO_1051 | X | 106,893,248 | 107,403,850 | 45 | 1.51 | |
| MO_1051 | 2 | 227,732,024 | 227,963,521 | 37 | 1.49 | |
| MO_1051 | 16 | 47,462,728 | 61,687,744 | 1025 | 1.47 | C16orf57, CYLD, NUP93 |
| MO_1051 | X | 107,938,154 | 117,959,778 | 339 | 1.45 | IRS4, PAK3 |
| MO_1051 | 20 | 29,652,166 | 59,197,288 | 2647 | 1.43 | ASXL1, AURKA, BCL2L1, CEBPB, GNAS, HCK, MAFB, MYBL2, NCOA3, NFATC2, PLCG1, PTPRT, SRC, STK4, TOP1, YWHAB, ZMYND8, ZNF217 |
| MO_1051 | 1 | 40,756,525 | 40,947,550 | 42 | 1.42 | |
| MO_1051 | 20 | 61,470,000 | 62,904,843 | 331 | 1.42 | ARFRP1, PTK6, SRMS |
| MO_1051 | X | 17,095,401 | 18,606,234 | 62 | 1.42 | |
| MO_1051 | 14 | 106,303,455 | 107,283,120 | 80 | 1.42 | |
| MO_1051 | 4 | 74,286,864 | 75,719,594 | 90 | 1.41 | AREG, BTC, EPGN, EREG |
| MO_1051 | X | 31,462,736 | 31,747,833 | 10 | 1.41 | |
| MO_1051 | X | 50,147,176 | 53,560,271 | 109 | 1.41 | KDM5C, MAGED1, SSX2 |
| MO_1051 | 16 | 97,456 | 47,117,398 | 3513 | 1.40 | ABCC1, AXIN1, CIITA, CREBBP, ERCC4, FUS, GRIN2A, MKL2, MLST8, MYH11, PALB2, PDPK1, PRSS8, SOCS1, TNFRSF17, TSC2, ZNF668 |
| MO_1051 | 7 | 158,055,758 | 158,119,500 | 5 | −0.34 | |
| MO_1051 | 12 | 50,271,607 | 50,273,606 | 3 | −0.33 | |
| MO_1051 | 12 | 132,911,966 | 133,032,417 | 5 | −0.30 | |
| MO_1051 | 6 | 169,114,856 | 169,115,787 | 3 | −0.18 | |
| MO_1051 | 4 | 88,535,422 | 88,537,643 | 3 | −0.16 | |
| MO_1051 | 9 | 96,424,692 | 96,425,932 | 3 | −0.11 | |
| MO_1051 | 7 | 5,632,990 | 5,643,110 | 3 | −0.10 | |
| MO_1051 | 7 | 141,919,835 | 141,920,772 | 3 | −0.10 | |
| MO_1051 | 19 | 2,542,606 | 2,576,124 | 6 | −0.03 | |
| MO_1051 | 17 | 11,145,036 | 11,999,005 | 89 | −0.02 | MAP2K4 |
| MO_1051 | 9 | 139,740,311 | 139,741,391 | 4 | −0.01 | |
| MO_1051 | 10 | 134,229,031 | 134,243,972 | 5 | 0.05 | |
| MO_1051 | 21 | 9,825,990 | 10,793,947 | 7 | 0.11 | |
| MO_1051 | 20 | 50,225,067 | 59,793,635 | 6 | 0.20 | |
| MO_1051 | 4 | 30,279,568 | 31,116,369 | 12 | 0.23 | |
| MO_1051 | 11 | 1,092,230 | 1,101,070 | 13 | 0.26 | |
| MO_1051 | 9 | 125,239,660 | 125,487,221 | 15 | 0.29 | |
| MO_1051 | 4 | 25,417,181 | 25,831,748 | 34 | 0.31 | |
| MO_1051 | 9 | 139,399,337 | 139,438,456 | 22 | 0.33 | NOTCH1 |

TABLE 4-continued

| Case ID | Chr | Loc Start | Loc End | # Exon Targets | Adj Copy Num Ratio | MiOncoSeq Panel Genes |
|---|---|---|---|---|---|---|
| MO_1051 | 7 | 100,634,044 | 100,686,182 | 26 | 0.36 | |
| MO_1051 | 11 | 122,859,980 | 124,489,589 | 140 | 0.36 | |
| MO_1051 | 5 | 140,167,837 | 140,263,912 | 57 | 0.37 | |
| MO_1051 | 22 | 17,058,814 | 22,673,386 | 650 | 0.41 | CRKL |
| MO_1051 | 6 | 74,183,252 | 74,304,854 | 17 | 0.42 | |
| MO_1051 | 3 | 97,711,728 | 98,251,403 | 36 | 0.42 | |
| MO_1051 | 22 | 39,709,358 | 51,216,322 | 1353 | 0.45 | CYP2D6, EP300, MKL1, PIM3, WNT7B |
| MO_1051 | 9 | 139,992,316 | 140,083,683 | 39 | 0.46 | |
| MO_1051 | 16 | 61,689,494 | 70,884,528 | 858 | 0.47 | CBFB, CDH1, CDH5, CTCF, NQO1 |
| MO_1051 | 17 | 12,011,235 | 21,207,774 | 755 | 0.47 | C17orf39, COPS3, FLCN, MAP2K4, NCOR1 |
| MO_1051 | 4 | 337,748 | 25,416,170 | 1492 | 0.48 | FGFR3, WHSC1 |
| MO_1051 | 8 | 183,094 | 681,251 | 32 | 0.48 | |
| MO_1051 | 17 | 436,106 | 7,830,984 | 1445 | 0.48 | CRK, DVL2, FGF11, GPS2, RABEP1, RPA1, TNK1, TP53, USP6 |
| MO_1051 | 22 | 23,404,080 | 39,355,591 | 1805 | 0.48 | BCR, CHEK2, CSNK1E, EWSR1, MN1, NF2, PATZ1, RAC2, SMARCB1, SOX10, XBP1 |
| MO_1051 | 22 | 134,986,740 | 134,993,900 | 15 | 0.48 | |
| MO_1051 | 8 | 39,521,388 | 54,730,033 | 579 | 0.48 | CEBPD, IKBKB, KAT6A, PRKDC |
| MO_1051 | 17 | 7,906,986 | 10,728,695 | 481 | 0.49 | ALOX12B, AURKB |
| MO_1051 | 11 | 5,730,622 | 6,226,929 | 35 | 0.50 | |
| MO_1051 | 16 | 89,300,336 | 90,142,217 | 221 | 0.51 | FANCA, MC1R |
| MO_1051 | 16 | 71,209,628 | 89,294,050 | 1193 | 0.53 | MAF, PHLPP2, PLCG2, ZFHX3 |
| MO_1051 | 11 | 110,306,688 | 122,653,778 | 1220 | 0.53 | CBL, DDX6, HMBS, MLL, POU2AF1, SDHD, UBE4A, ZBTB16 |
| MO_1051 | 12 | 208,418 | 18,576,865 | 1758 | 0.54 | CCND2, CDKN1B, ETV6, FGF23, FGF6, FOXM1, ING4, KDM5A, LRP6, NTF3, PIK3C2G, STYK1, WNT5B, ZNF364 |
| MO_1051 | 8 | 1,497,380 | 38,879,197 | 2010 | 0.55 | BAG4, BLK, FGF17, FGF20, FGFR1, GPR124, LSM1, NKX3-1, NRG1, PTK2B, TNKS, WHSC1L1, WRN, ZNF703 |
| MO_1051 | 11 | 124,493,156 | 134,257,653 | 661 | 0.56 | CHEK1, ETS1, FLI1 |
| MO_1051 | 12 | 19,282,894 | 21,168,580 | 85 | 0.57 | |
| MO_1051 | 4 | 31,129,613 | 69,885,766 | 1352 | 0.57 | CHIC2, EPHA5, KDR, KIT, LPHN3, PDGFRA, PHOX2B, RHOH, TEC, TXK |
| MO_1051 | 17 | 41,957,310 | 42,636,450 | 157 | 0.57 | G6PC3 |
| MO_1051 | X | 63,005,978 | 79,938,015 | 771 | 0.61 | AR, ATRX, FAM123B, FGF16, FOXO4, MED12, TBX22 |
| MO_1051 | 2 | 170,019,028 | 170,101,253 | 41 | 0.62 | |
| MO_1051 | X | 118,109,145 | 118,145,782 | 9 | 0.62 | |
| MO_1051 | 22 | 22,781,917 | 23,230,282 | 44 | 0.62 | |
| MO_1051 | 1 | 120,480,070 | 142,540,225 | 24 | 0.63 | NOTCH2 |
| MO_1051 | 12 | 22,354,800 | 23,696,160 | 49 | 0.63 | |
| MO_1051 | 7 | 128,457,794 | 128,527,239 | 46 | 0.64 | |
| MO_1051 | 12 | 57,543,422 | 57,604,578 | 56 | 0.64 | |
| MO_1051 | 4 | 25,834,611 | 30,222,415 | 79 | 0.65 | RBPJ |
| MO_1051 | 20 | 68,356 | 29,633,982 | 1441 | 0.65 | PAK7 |
| MO_1051 | 4 | 106,369,290 | 107,158,004 | 67 | 0.65 | |
| MO_1051 | 16 | 47,120,256 | 47,409,815 | 19 | 0.65 | |
| MO_1051 | X | 2,947,315 | 9,621,620 | 102 | 0.66 | |
| MO_1051 | 15 | 50,450,347 | 23,686,296 | 97 | 0.67 | |
| MO_1051 | 3 | 96,585,718 | 97,705,619 | 67 | 0.70 | EPHA6 |
| MO_1051 | 4 | 85,827 | 331,662 | 17 | 0.70 | |
| MO_1051 | 11 | 4,411,528 | 5,602,632 | 88 | 0.71 | |
| MO_1051 | 19 | 36,685,981 | 37,689,941 | 106 | 0.71 | |
| MO_1051 | 11 | 862,652 | 1,091,424 | 89 | 0.71 | |
| MO_1051 | 19 | 52,497,138 | 53,716,488 | 176 | 0.72 | PPP2R1A |
| MO_1051 | 21 | 45,736,218 | 46,311,818 | 115 | 0.73 | |
| MO_1051 | 15 | 25,232,160 | 25,351,768 | 30 | 0.74 | |
| MO_1051 | 17 | 41,168,284 | 41,603,952 | 90 | 0.74 | BRCA1 |
| MO_1069 | 17 | 81,006,503 | 81,083,588 | 6 | 4.47 | |
| MO_1069 | 18 | 641,494 | 736,954 | 28 | 4.38 | YES1 |
| MO_1069 | 17 | 67,512,994 | 68,171,885 | 13 | 4.32 | |
| MO_1069 | 17 | 65,528,925 | 66,453,492 | 105 | 3.90 | |
| MO_1069 | 17 | 63,746,813 | 65,214,752 | 91 | 3.83 | |
| MO_1069 | 17 | 71,232,438 | 73,874,342 | 538 | 3.70 | GRB2 |
| MO_1069 | 12 | 8,906,702 | 8,925,873 | 2 | 3.59 | |
| MO_1069 | 17 | 74,846,540 | 76,100,688 | 77 | 3.36 | |
| MO_1069 | 17 | 46,154,428 | 46,928,948 | 72 | 3.33 | HOXB13 |
| MO_1069 | 1 | 211,749,146 | 211,847,883 | 10 | 3.02 | |
| MO_1069 | 18 | 158,542 | 633,304 | 51 | 2.95 | |
| MO_1069 | 1 | 248,201,992 | 248,367,364 | 9 | 2.87 | |
| MO_1069 | 18 | 739,832 | 1,278,637 | 14 | 2.86 | YES1 |
| MO_1069 | 17 | 48,423,574 | 48,721,012 | 126 | 2.54 | |

TABLE 4-continued

| Case ID | Chr | Loc Start | Loc End | # Exon Targets | Adj Copy Num Ratio | MiOncoSeq Panel Genes |
|---|---|---|---|---|---|---|
| MO_1069 | 17 | 60,064,432 | 63,739,228 | 442 | 2.43 | AXIN2, CD79B |
| MO_1069 | 17 | 80,575,285 | 80,992,948 | 79 | 2.40 | |
| MO_1069 | 6 | 135,778,773 | 135,839,774 | 11 | 2.35 | |
| MO_1069 | 17 | 65,336,945 | 65,374,292 | 11 | 2.35 | |
| MO_1069 | 17 | 53,798,298 | 80,062,226 | 627 | 2.09 | BRIP1, PPM1D, RAD51C, RNF43, RPS6KB1 |
| MO_1069 | 2 | 44,008,719 | 44,139,663 | 44 | 2.05 | |
| MO_1069 | 17 | 76,104,556 | 80,574,524 | 916 | 1.98 | AATK, BIRC5, RNF213, RPTOR, TMC6, TMC8 |
| MO_1069 | 17 | 73,887,101 | 74,774,345 | 247 | 1.97 | SRSF2 |
| MO_1069 | 11 | 65,960,946 | 67,290,032 | 367 | 1.96 | AIP, RBM14 |
| MO_1069 | 17 | 48,733,210 | 51,901,464 | 138 | 1.93 | |
| MO_1069 | 17 | 46,929,932 | 48,356,715 | 222 | 1.93 | PHB, SPOP |
| MO_1069 | 17 | 66,511,554 | 67,178,942 | 147 | 1.92 | PRKAR1A |
| MO_1069 | 17 | 69,334,538 | 71,228,340 | 34 | 1.91 | |
| MO_1069 | 11 | 67,352,142 | 134,257,653 | 4523 | 1.90 | ATM, BIRC2, BIRC3, C11orf30, CBL, CCND1, CHEK1, DDX6, ETS1, FADD, FGF19, FGF3, FGF4, FLI1, GAB2, GUCY1A2, HMBS, LRP5, MAML2, MLL, MRE11A, PAK1, PDGFD, PICALM, POU2AF1, SDHD, UBE4A, WNT11, YAP1, ZBTB16 |
| MO_1069 | 1 | 247,737,584 | 246,185,858 | 22 | 1.88 | |
| MO_1069 | 17 | 43,718,058 | 46,153,561 | 271 | 1.81 | WNT3, WNT9B |
| MO_1069 | 1 | 248,402,327 | 249,211,679 | 37 | 1.79 | |
| MO_1069 | 2 | 238,273,091 | 238,449,050 | 23 | 1.73 | |
| MO_1069 | X | 50,055,582 | 50,167,242 | 34 | 1.65 | CCNB3 |
| MO_1069 | 12 | 5,915,310 | 6,0626,648 | 16 | 1.64 | |
| MO_1069 | 15 | 101,464,798 | 101,608,913 | 34 | 1.63 | |
| MO_1069 | 20 | 57,245,562 | 57,292,974 | 20 | 1.59 | |
| MO_1069 | 2 | 214,727,212 | 219,146,824 | 316 | 1.55 | BARD1 |
| MO_1069 | 2 | 43,927,208 | 44,003,978 | 23 | 1.55 | |
| MO_1069 | 12 | 120,111,766 | 120,173,122 | 26 | 1.54 | |
| MO_1069 | 15 | 72,338,509 | 91,769,702 | 1766 | 1.53 | BCL2A1, BLM, CRTC3, CSK, FANCI, FES, IDH2, IQGAP1, NRG4, NTRK3, PML |
| MO_1069 | 3 | 195,452,936 | 195,610,114 | 40 | 1.53 | TNK2 |
| MO_1069 | 3 | 61,734,674 | 65,433,782 | 183 | 1.53 | PTPRG |
| MO_1069 | 3 | 5,164,069 | 18,462,351 | 1018 | 1.51 | FANCD2, PPARG, RAF1, VHL, WNT7A, XPC |
| MO_1069 | 17 | 67,181,674 | 67,501,961 | 56 | 1.51 | |
| MO_1069 | 18 | 70,205,454 | 78,005,236 | 238 | 1.51 | CADM2, ROBO2 |
| MO_1069 | 3 | 75,790,546 | 87,100,805 | 103 | 1.51 | |
| MO_1069 | 3 | 97,753,837 | 98,217,270 | 20 | 1.51 | |
| MO_1069 | 19 | 51,413,897 | 51,584,944 | 51 | 1.50 | |
| MO_1069 | 20 | 32,441,436 | 33,012,336 | 31 | 1.49 | |
| MO_1069 | 17 | 42,635,108 | 42,636,450 | 3 | 1.48 | |
| MO_1069 | 2 | 44,145,334 | 44,428,753 | 28 | 1.48 | |
| MO_1069 | 1 | 103,480,082 | 149,899,706 | 1500 | 1.48 | BCL9, CHD1L, CSF1, FAM46C, NGF, NOTCH2, NRAS, WNT2B |
| MO_1069 | 7 | 138,400,628 | 151,433,128 | 1172 | 1.48 | BRAF, EPHA1, EPHB6, EZH2, PRSS1, RHEB |
| MO_1069 | 1 | 150,912,430 | 211,654,670 | 5646 | 1.47 | ABL2, CDC73, CKS1B, DDR2, ELF3, ELK4, ETV3, ETV3L, FASLG, HAX1, IKBKE, INSRR, IQGAP3, IRF6, MDM4, NCSTN, NTRK1, PBX1, PBX1, PRRX1, RAB25, SDHC, SHC1 |
| MO_1069 | 19 | 18,218,476 | 18,391,780 | 61 | 1.46 | JUND, PIK3R2 |
| MO_1069 | 8 | 29,207,626 | 30,982,114 | 107 | 1.46 | WRN |
| MO_1069 | 1 | 211,923,224 | 231,155,638 | 1347 | 1.46 | H3F3A, PSEN2, WNT3A, WNT9A |
| MO_1069 | X | 48,463,399 | 48,689,705 | 44 | 1.45 | GATA1, WAS |
| MO_1069 | 19 | 40,514,428 | 40,589,194 | 29 | 1.44 | |
| MO_1069 | 19 | 54,632,528 | 54,659,064 | 13 | 1.44 | |
| MO_1069 | 16 | 29,001,065 | 30,393,825 | 155 | 1.44 | |
| MO_1069 | 18 | 12,008,430 | 13,105,058 | 155 | 1.44 | |
| MO_1069 | 11 | 50,003,405 | 56,237,946 | 67 | 1.43 | |
| MO_1069 | 1 | 29,385,200 | 103,385,894 | 5195 | 1.42 | ARTN, BCL10, CDKN2C, CMPK1, DPYD, FUBP1, GFI1, JAK1, JUN, LCK, MAST2, MPL, MUTYH, MYCL1, PTCH2, RAD54L, RBMXL1, ROR1, TAL1, TIE1 |
| MO_1069 | 19 | 40,095,937 | 40,225,610 | 18 | 1.42 | |
| MO_1069 | 12 | 63,541,308 | 101,873,615 | 1849 | 1.41 | BTG1, DYRK2, ELK3, FRS2, HMGA2, KITLG, MDM2, PTPRR, SPIC, YEATS4 |
| MO_1069 | 1 | 231,299,237 | 247,729,174 | 983 | 1.40 | AKT3, FH |
| MO_1069 | 5 | 137,734,039 | 138,118,040 | 51 | 1.40 | CTNNA1, KDM3B |
| MO_1069 | 16 | 31,896,454 | 34,681,986 | 29 | 1.40 | |

TABLE 4-continued

| Case ID | Chr | Loc Start | Loc End | # Exon Targets | Adj Copy Num Ratio | MiOncoSeq Panel Genes |
|---|---|---|---|---|---|---|
| MO_1069 | 17 | 33,611,080 | 33,638,804 | 4 | 0.09 | |
| MO_1069 | 7 | 100,187,314 | 100,188,694 | 4 | 0.17 | |
| MO_1069 | 17 | 32,809,035 | 32,820,286 | 5 | 0.18 | |
| MO_1069 | 21 | 41,140,492 | 41,462,159 | 3 | 0.27 | |
| MO_1069 | 19 | 11,373,858 | 11,390,874 | 8 | 0.28 | |
| MO_1069 | 9 | 113,210,718 | 113,385,698 | 37 | 0.39 | |
| MO_1069 | 5 | 70,841,173 | 70,844,815 | 6 | 0.41 | |
| MO_1069 | 13 | 109,613,925 | 109,956,892 | 79 | 0.43 | |
| MO_1069 | 5 | 137,532,229 | 137,542,289 | 8 | 0.44 | |
| MO_1069 | 17 | 40,089,486 | 40,164,050 | 18 | 0.45 | |
| MO_1069 | 1 | 39,126,286 | 39,134,277 | 3 | 0.49 | |
| MO_1069 | 1 | 25,539,630 | 29,252,385 | 552 | 0.51 | ARID1A, CD52, FGR, MAP3K6, PDIK1L, RPS6KA1 |
| MO_1069 | 17 | 32,822,782 | 33,606,210 | 68 | 0.51 | |
| MO_1069 | 17 | 33,708,893 | 36,332,740 | 564 | 0.51 | ERBB2, LASP1, MLLT6, RARA |
| MO_1069 | 17 | 40,192,184 | 40,923,970 | 167 | 0.51 | |
| MO_1069 | 19 | 10,830,006 | 11,371,818 | 157 | 0.51 | SMARCA4 |
| MO_1069 | 16 | 51,432,288 | 69,401,274 | 1621 | 0.52 | CBFB, CDH1, CDH11, CSNK2A2, HERPUD1, PSKH1 |
| MO_1069 | 17 | 6,108 | 23,543,324 | 2894 | 0.52 | AURKB, CAMKK1, FLCN, GAS7, GSG2, GUCY2D, MAP2K3, MAP2K4, MAPK7, PER1, TP53, ULK2, USP6 |
| MO_1069 | 17 | 36,928,482 | 39,936,174 | 751 | 0.52 | BRCA1, ETV4, WNK4 |
| MO_1069 | 19 | 7,512,372 | 8,392,876 | 226 | 0.52 | MAP2K7 |
| MO_1069 | 19 | 11,392,694 | 18,070,508 | 1424 | 0.52 | BRD4, JAK3, LYL1, MAST1, PKN1, PRKACA, TPM4 |
| MO_1069 | 3 | 197,579,348 | 197,614,259 | 7 | 0.54 | |
| MO_1069 | 6 | 68,655,658 | 126,361,388 | 2422 | 0.54 | EPHA7, FRK, FYN, GOPC, MAP3K7, PRDM1, ROS1, TTK |
| MO_1069 | 9 | 126,773,579 | 130,420,973 | 558 | 0.54 | CDK9 |
| MO_1069 | 16 | 45,065,780 | 49,742,682 | 362 | 0.54 | CYLD |
| MO_1069 | 16 | 69,767,130 | 87,910,942 | 1206 | 0.54 | CBFA2T3, MAF, MLKL |
| MO_1069 | 1 | 752,046 | 25,445,741 | 3061 | 0.55 | CDA, EPHA2, EPHA8, EPHB2, MTHFR, PAX7, PINK1, PRDM16, PRKCZ, RPL22, SDHB, TNFRSF14 |
| MO_1069 | 6 | 36,128,488 | 83,053,829 | 1872 | 0.55 | CCND3, ICK, MAPK13, MAPK14, PIM1, PTK7, STK38, TFEB, TTBK1 |
| MO_1069 | 9 | 70,284,154 | 94,206,698 | 1056 | 0.55 | DAPK1, GNAQ, NTRK2, PRKACG, ROR2, SYK, TRPM6 |
| MO_1069 | 9 | 94,778,540 | 112,840,718 | 1124 | 0.55 | FANCC, NR4A3, TAL2, TGFBR1, XPA |
| MO_1069 | 9 | 113,388,245 | 126,671,370 | 989 | 0.55 | NEK6 |
| MO_1069 | 17 | 23,824,874 | 32,807,220 | 1065 | 0.55 | NEK8, NF1, SUZ12, TAF15, TAOK1 |
| MO_1069 | 2 | 102,140,611 | 157,175,420 | 2049 | 0.56 | ACVR2A, BUB1, ERCC3, MERTK, PAX8, TTL, YSK4 |
| MO_1069 | 9 | 130,552,829 | 139,852,678 | 1690 | 0.56 | ABL1, BRD3, C9orf96, NOTCH1, NUP214, RALGDS, TSC1 |
| MO_1069 | 13 | 18,499,113 | 109,612,623 | 3022 | 0.56 | BRCA2, CDK8, CDX2, CSNK1A1L, ERCC5, FLT1, FLT3, LATS2, LCP1, LHFP, NEK5, RB1, STK24 |
| MO_1069 | 15 | 37,793,066 | 37,855,893 | 9 | 0.56 | |
| MO_1069 | 22 | 15,438,814 | 49,563,186 | 3901 | 0.56 | ADRBK2, BCR, CHEK2, CSNK1E, CYP2D6, EP300, EWSR1, LIMK2, MAPK1, MAPK11, MAPK12, MKL1, MN1, MYH9, NF2, PDGFB, PIM3, SMARCB1, TSSK2 |
| MO_1069 | 6 | 160,872,714 | 170,731,132 | 449 | 0.57 | FGFR1OP, MAP3K4, MLLT4, RPS6KA2 |
| MO_1069 | 19 | 50,688,434 | 50,721,098 | 15 | 0.57 | |
| MO_1069 | 3 | 214,492 | 5,000,018 | 186 | 0.59 | |
| MO_1069 | 13 | 109,958,488 | 114,108,621 | 377 | 0.59 | |
| MO_1069 | 8 | 144,312,499 | 146,250,262 | 372 | 0.61 | ADCK5, MAPK15, NRBP2 |
| MO_1069 | 16 | 88,333,032 | 88,669,718 | 118 | 0.62 | FANCA |
| MO_1129 | 11 | 78,525,452 | 78,614,830 | 8 | 10.71 | |
| MO_1129 | 11 | 76,507,253 | 77,734,336 | 152 | 10.44 | PAK1 |
| MO_1129 | 16 | 53,403,481 | 53,496,546 | 18 | 8.99 | |
| MO_1129 | 11 | 73,063,928 | 73,179,552 | 31 | 8.52 | |
| MO_1129 | 16 | 46,702,906 | 46,725,038 | 15 | 8.27 | |
| MO_1129 | 11 | 74,883,581 | 75,442,324 | 74 | 8.26 | |
| MO_1129 | 16 | 47,005,363 | 47,294,464 | 18 | 8.25 | |
| MO_1129 | 11 | 70,118,324 | 70,858,343 | 99 | 8.05 | |
| MO_1129 | 11 | 75,776,855 | 75,907,581 | 8 | 7.45 | WNT11 |
| MO_1129 | 11 | 78,775,826 | 79,113,172 | 3 | 7.42 | |
| MO_1129 | 11 | 77,820,528 | 78,523,328 | 65 | 7.34 | GAB2 |
| MO_1129 | 11 | 77,749,826 | 77,812,121 | 6 | 7.33 | |
| MO_1129 | 11 | 76,075,526 | 76,432,738 | 46 | 7.20 | C11orf30 |
| MO_1129 | 11 | 75,917,402 | 76,072,153 | 4 | 5.66 | WNT11 |
| MO_1129 | 11 | 77,814,044 | 77,817,892 | 4 | 5.36 | |
| MO_1129 | 16 | 47,345,262 | 48,643,775 | 120 | 4.92 | |

TABLE 4-continued

| Case ID | Chr | Loc Start | Loc End | # Exon Targets | Adj Copy Num Ratio | MiOncoSeq Panel Genes |
|---|---|---|---|---|---|---|
| MO_1129 | 16 | 49,823,481 | 50,402,219 | 76 | 4.80 | |
| MO_1129 | 16 | 46,597,978 | 46,695,978 | 20 | 4.79 | |
| MO_1129 | 16 | 46,726,382 | 47,001,976 | 38 | 4.58 | |
| MO_1129 | 16 | 52,874,786 | 53,358,370 | 42 | 4.51 | |
| MO_1129 | 16 | 54,317,524 | 54,967,290 | 13 | 4.35 | |
| MO_1129 | 16 | 56,672,724 | 56,839,479 | 26 | 4.22 | NUP93 |
| MO_1129 | 11 | 73,669,488 | 74,880,866 | 172 | 3.98 | |
| MO_1129 | 11 | 68,705,664 | 70,052,410 | 81 | 3.82 | CCND1, FADD, FGF19, FGF3, FGF4 |
| MO_1129 | 16 | 33,965,608 | 34,681,986 | 19 | 2.67 | |
| MO_1129 | 16 | 97,458 | 29,001,065 | 2902 | 2.54 | ABCC1, AXIN1, CIITA, CREBBP, ERCC4, GRIN2A, MKL2, MLST8, MYH11, PALB2, PDPK1, SOCS1, TNFRSF17, TSC2 |
| MO_1129 | 1 | 145,209,248 | 147,415,496 | 171 | 2.02 | BCL9, CHD1L |
| MO_1129 | 1 | 150,039,962 | 249,211,679 | 8247 | 2.00 | ABL2, AKT3, APH1A, ARNT, CDC73, CKS1B, DDR2, ELF3, ELK4, ETV3, ETV3L, FASLG, FH, H3F3A, HAX1, IKBKE, INSRR, IQGAP3, IRF6, MCL1, MDM4, NCSTN, NTRK1, PBX1, PBX1, PRRX1, PSEN2, RAB25, SDHC, SHC1, WNT3A, WNT9A |
| MO_1129 | 14 | 22,749,583 | 22,961,931 | 35 | 1.60 | |
| MO_1129 | 11 | 61,091,464 | 68,704,130 | 1737 | 1.53 | AIP, ESRRA, FOSL1, LRP5, MEN1, RBM14, SDHAF2, VEGFB |
| MO_1129 | 1 | 144,864,331 | 145,115,804 | 44 | 1.51 | |
| MO_1129 | 11 | 30,921,108 | 46,918,422 | 805 | 1.49 | CREB3L1, EHF, ELF5, EXT2, LMO2, WT1 |
| MO_1129 | 5 | 140,648 | 180,687,459 | 8736 | 1.48 | ACSL6, APC, ARHGAP26, CSF1R, CTNNA1, FER, FGF1, FGF10, FGF18, FGFR4, FLT4, GDNF, HBEGF, IL3, IL7R, IQGAP2, ITK, KDM3B, MAML1, MAP3K1, NHP2, NKX2-5, NPM1, NRG2, NSD1, ODZ2, PDGFRB, PIK3R1, RAD50, RICTOR, SKP2, SMAD5, TCF7, TERT, TLX3, UBE2D2, WNT8A |
| MO_1129 | 16 | 29,141,009 | 33,953,903 | 503 | 1.47 | FUS, PRSS8, ZNF668 |
| MO_1129 | X | 2,700,167 | 94,318,128 | 3523 | 1.47 | AR, ARAF, ATRX, BCOR, BMX, CCNB3, DDX3X, ELK1, FAM123B, FANCB, FGF16, FIGF, FOXO4, FOXP3, GATA1, KDM5C, KDM6A, MAGED1, MED12, PIM2, SSX1, SSX2, SSX3, SSX4, TBX22, TFE3, USP9X, WAS, ZRSR2 |
| MO_1129 | 16 | 70,883,704 | 71,127,808 | 66 | 1.44 | |
| MO_1129 | 11 | 48,373,888 | 50,003,636 | 30 | 1.40 | |
| MO_1129 | 11 | 75,480,074 | 75,727,920 | 20 | 0.44 | |
| MO_1129 | 11 | 81,601,827 | 134,257,653 | 3268 | 0.44 | ATM, BIRC2, BIRC3, CBL, CHEK1, DDX6, ETS1, FLI1, GUCY1A2, HMBS, MAML2, MLL, MRE11A, PDGFD, PICALM, POU2AF1, SDHD, UBE4A, YAP1, ZBTB16 |
| MO_1129 | X | 95,904,052 | 154,774,783 | 2605 | 0.45 | BTK, CUL4B, DKC1, ELF4, FGF13, GPC3, IRS4, MAMLD1, MTCP1, PAK3, PHF6, RBMX, SH2D1A, STAG2 |
| MO_1129 | 22 | 17,058,814 | 51,219,026 | 3934 | 0.45 | BCR, CHEK2, CRKL, CSNK1E, CYP2D6, EP300, EWSR1, MKL1, MN1, NF2, PATZ1, PDGFB, PIM3, RAC2, SMARCB1, SOX10, WNT7B, XBP1 |
| MO_1129 | 11 | 50,003,984 | 61,090,461 | 587 | 0.45 | |
| MO_1129 | 11 | 71,139,834 | 73,057,972 | 257 | 0.46 | |
| MO_1129 | 11 | 73,357,684 | 73,662,078 | 40 | 0.46 | |
| MO_1167 | 19 | 281,501 | 375,803 | 27 | 2.42 | |
| MO_1167 | 7 | 95,906,650 | 95,926,311 | 2 | 2.38 | |
| MO_1167 | 12 | 34,179,755 | 40,265,674 | 91 | 1.98 | |
| MO_1167 | 2 | 61,436,070 | 61,449,714 | 6 | 1.83 | |
| MO_1167 | 16 | 47,622,910 | 48,643,775 | 99 | 1.82 | |
| MO_1167 | 14 | 50,081,150 | 51,132,300 | 195 | 1.79 | |
| MO_1167 | 17 | 26,206,406 | 81,083,588 | 7129 | 1.75 | AATK, AXIN2, BIRC5, BRCA1, BRIP1, CD79B, CDC6, CDK12, ERBB2, ETV4, G6PC3, GRB2, GRB7, HLF, HOXB13, NF1, PHB, PPM1D, PRKAR1A, RAD51C, RAD51D, RARA, RHOT1, RNF213, RNF43, RPS6KB1, RPTOR, SPOP, SRSF2, STARD3, STAT3, STAT5A, STAT5B, SUZ12, TAF15, TMC6, TMC8, TOP2A, WNT3, WNT9B |

TABLE 4-continued

| Case ID | Chr | Loc Start | Loc End | # Exon Targets | Adj Copy Num Ratio | MiOncoSeq Panel Genes |
|---|---|---|---|---|---|---|
| MO_1167 | 8 | 67,356,790 | 69,699,728 | 230 | 1.74 | MYBL1, PREX2 |
| MO_1167 | 20 | 17,585,297 | 17,716,465 | 26 | 1.65 | |
| MO_1167 | 20 | 22,563,126 | 62,904,843 | 3391 | 1.62 | ARFRP1, ASXL1, AURKA, BCL2L1, CEBPB, GNAS, HCK, MAFB, MYBL2, NCOA3, NFATC2, PLCG1, PTK6, PTPRT, SRC, SRMS, STK4, TOP1, YWHAB, ZMYND8, ZNF217 |
| MO_1167 | 2 | 95,537,503 | 103,380,773 | 809 | 1.44 | AFF3, TMEM127, ZAP70 |
| MO_1167 | 2 | 239,974,737 | 242,964,616 | 471 | 1.39 | |
| MO_1167 | 12 | 25,031,453 | 34,179,497 | 529 | 1.36 | KRAS |
| MO_1167 | 9 | 38,573,205 | 38,596,389 | 2 | −0.11 | |
| MO_1185 | 1 | 196,748,491 | 196,799,835 | 7 | 3.41 | |
| MO_1185 | 7 | 95,951,322 | 100,320,578 | 611 | 2.68 | ARPC1A, LMTK2, SHFM1, SMURF1, TRRAP |
| MO_1185 | 7 | 63,506,056 | 95,864,204 | 1523 | 2.66 | ABCB1, AKAP9, CDK6, GRM3, HGF, MAGI2, SAMD9, SBDS, TYW1 |
| MO_1185 | 1 | 248,802,276 | 249,211,679 | 20 | 2.65 | |
| MO_1185 | 7 | 193,482 | 37,072,998 | 2058 | 2.57 | CARD11, ETV1, FKBP9, HOXA10, HOXA11, HOXA13, HOXA13, HOXA9, JAZF1, PDGFA, PMS2, RAC1 |
| MO_1185 | 7 | 100,344,251 | 158,937,252 | 3847 | 2.57 | BRAF, CREB3L2, EPHA1, EPHB4, EPHB6, EZH2, GRM8, MET, MLL3, MNX1, PIK3CG, PRSS1, RHEB, SHH, SMO, WNT16, WNT2 |
| MO_1185 | 1 | 145,415,489 | 151,547,427 | 614 | 2.40 | APH1A, ARNT, BCL9, CHD1L, MCL1 |
| MO_1185 | 1 | 196,857,390 | 248,685,378 | 3899, | 2.38 | AKT3, ELF3, ELK4, FH, H3F3A, IKBKE, IRF6, MDM4, PSEN2, WNT3A, WNT9A |
| MO_1185 | 1 | 151,584,804 | 196,743,924 | 3920 | 2.29 | ABL2, CDC73, CKS1B, DDR2, ETV3, ETV3L, FASLG, HAX1, INSRR, IQGAP3, NCSTN, NTRK1, PBX1, PBX1, PRRX1, RAB25, SDHC, SHC1 |
| MO_1185 | 1 | 1,221,024 | 1,231,394 | 10 | 2.13 | |
| MO_1185 | 16 | 97,456 | 34,681,986 | 3427 | 1.84 | ABCC1, AXIN1, CIITA, CREBBP, ERCC4, FUS, GRIN2A, MKL2, MLST8, MYH11, PALB2, PDPK1, PRSS8, SOCS1, TNFRSF17, TSC2, ZNF668 |
| MO_1185 | 18 | 158,542 | 15,004,215 | 819 | 1.80 | YES1 |
| MO_1185 | 1 | 142,540,225 | 145,414,742 | 50 | 1.77 | |
| MO_1185 | 3 | 138,724,967 | 138,739,359 | 5 | 1.76 | |
| MO_1185 | 10 | 225,997 | 135,381,649 | 7791 | 1.65 | BLNK, BMPR1A, CHUK, CYP17A1, FAS, FGF8, FGFR2, GATA3, GOT1, KAT6B, KLF6, LDB1, MLLT10, NCOA4, NFKB2, NRG3, PRF1, PTEN, RET, SHOC2, SUFU, TCF7L2, TLX1, TNKS2, WNT8B |
| MO_1185 | X | 33,148,306 | 33,357,442 | 3 | −0.73 | |
| MO_1185 | 12 | 115,109,830 | 117,537,171 | 80 | −0.71 | TBX3 |
| MO_1185 | 21 | 9,825,990 | 9,826,257 | 2 | −0.55 | |
| MO_1185 | 16 | 55,844,562 | 55,862,856 | 8 | −0.25 | |
| MO_1185 | 17 | 7,107,475 | 7,7,124,954 | 11 | −0.09 | |
| MO_1185 | 20 | 32,684,636 | 32,685,368 | 2 | −0.07 | |
| MO_1185 | X | 34,148,030 | 154,774,783 | 4899 | 0.12 | AR, ARAF, ATRX, BCOR, BTK, CCNB3, CUL4B, DDX3X, DKC1, ELF4, ELK1, FAM123B, FGF13, FGF16, FOXO4, FOXP3, GATA1, GPC3, IRS4, KDM5C, KDM6A, MAGED1, MAMLD1, MED12, MTCP1, PAK3, PHF6, PIM2, RBMX, SH2D1A, SSX1, SSX2, SSX3, SSX4, STAG2, TBX22, TFE3, USP9X, WAS |
| MO_1185 | 11 | 74,700,123 | 76,261,098 | 146 | 0.13 | C11orf30, WNT11 |
| MO_1185 | 16 | 46,508,278 | 55,807,285 | 552 | 0.13 | CYLD |
| MO_1185 | 17 | 7,125,469 | 22,023,536 | 1678 | 0.13 | ALOX12B, AURKB, C17orf39, CCPS3, DVL2, FGF11, FLCN, GPS2, MAP2K4, NCOR1, TNK1, TP53 |
| MO_1185 | 1 | 2,700,257 | 25,350,002 | 2584 | 0.13 | CAMTA1, CDC42, EPHA2, EPHA8, EPHB2, KJF1B, MDS2, MTOR, PAX7, PLA2G2A, PRDM16, SDHB, SPEN, WNT4 |
| MO_1185 | 18 | 18,539,877 | 78,005,236 | 2224 | 0.13 | ASXL3, BCL2, CDH2, CDH20, GATA6, KDSR, MALT1, MBD1, PIK3C3, ROCK1, SMAD2, SMAD4, SMAD7, SS18 |
| MO_1185 | 16 | 55,866,960 | 70,867,000 | 1447 | 0.13 | C16orf57, CBFB, CDH1, CDH5, CTCF, NQO1, NUP93 |
| MO_1185 | X | 2,700,167 | 33,038,217 | 1236 | 0.14 | BMX, FANCB, FIGF, ZRSR2 |

TABLE 4-continued

| Case ID | Chr | Loc Start | Loc End | # Exon Targets | Adj Copy Num Ratio | MiOncoSeq Panel Genes |
|---|---|---|---|---|---|---|
| MO_1185 | 16 | 71,209,626 | 90,142,217 | 1419 | 0.14 | FANCA, MAF, MC1R, PHLPP2, FLCG2, ZFHX3 |
| MO_1185 | 11 | 59,540,716 | 64,883,160 | 1131 | 0.16 | ESRRA, MEN1, SDHAF2, VEGFB |
| MO_1185 | 17 | 6,108 | 7,106,560 | 1144 | 0.16 | CRK, RABEP1, RPA1, USP6 |
| MO_1185 | 11 | 94,603,981 | 118,247,352 | 1413 | 0.39 | ATM, BIRC2, BIRC3, GUCY1A2, MAML2, PDGFD, POU2AF1, SDHD, UBE4A, YAP1, ZBTB16 |
| MO_1185 | 7 | 44,121,933 | 44,146,309 | 4 | 0.40 | |
| MO_1185 | 3 | 77,526,710 | 77,595,553 | 7 | 0.40 | ROBO2 |

TABLE 5

| SAMPLE ID | 5' Gene | Chr | hg19 position | 3' Gene | Chr | hg19 position | # Supporting Reads | Fusion Protein |
|---|---|---|---|---|---|---|---|---|
| MO_1031 | CDC123 | 10 | 12272994 | LOC550112 | 4 | 68582640 | 172 | NO |
| MO_1031 | SFRP1 | 8 | 41161056 | ST8SIA6-AS1 | 10 | 17441200 | 435 | NO |
| MO_1031 | PLA2G12A | 4 | 110650757 | COL15A1 | 9 | 101822170 | 76 | YES |
| MO_1031 | USP6NL | 10 | 11551593 | UNC5D | 8 | 35232883 | 182 | NO |
| MO_1031 | PPIF | 10 | 81111338 | AL359195.1 | 10 | 82012039 | 667 | NO |
| MO_1031 | RAB10 | 2 | 26257603 | SPTBN1 | 2 | 54849604 | 24 | NO |
| MO_1031 | NT5C3L | 17 | 39991321 | SPATS2L | 2 | 201324491 | 21 | NO |
| MO_1031 | RAB11FIP1 | 8 | 37727937 | CCDC3 | 10 | 13006451 | 45 | NO |
| MO_1031 | LRRC56 | 11 | 540132 | NELL1 | 11 | 21197964 | 7 | NO |
| MO_1031 | CADM2 | 3 | 85851345 | CCDC3 | 10 | 13021206 | 8 | NO |
| MO_1031 | IPO9 | 1 | 201817721 | PM20D1 | 1 | 205814684 | 13 | YES |
| MO_1031 | NLK | 17 | 26459834 | AC015849.2.1 | 17 | 34211385 | 40 | NO |
| MO_1031 | STAM | 10 | 17688377 | CADM2 | 3 | 85288106 | 72 | NO |
| MO_1031 | ARSJ(AS) | 4 | 114880675 | TBC1D9 | 4 | 141622767 | 130 | NO |
| MO_1031 | EVI5 | 1 | 93029198 | PRKACB | 1 | 84596236 | 15 | NO |
| MO_1031 | STAM | 10 | 17686377 | PROSC | 8 | 37623043 | 33 | NO |
| MO_1031 | ADIPOR2 | 12 | 1800377 | HEBP1 | 12 | 13142347 | 258 | NO |
| MO_1031 | LRP5 | 11 | 68080272 | FAT3 | 11 | 92430549 | 11 | YES |
| MO_1051 | CMAS | 12 | 22199494 | PIK3C2G | 12 | 18641380 | 73 | YES |
| MO_1051 | TBCK | 4 | 107163626 | PPA2 | 4 | 106367658 | 81 | YES |
| MO_1051 | ITFG1 | 16 | 47399692 | NETO2 | 16 | 47117706 | 53 | NO |
| MO_1051 | GPATCH8 | 17 | 42512432 | MPP2 | 17 | 41961522 | 24 | YES |
| MO_1051 | FGFR2 | 10 | 123243211 | AFF3 | 2 | 100453985 | 138 | YES |
| MO_1069 | ANKRD11 | 16 | 89484691 | VPS9D1 | 16 | 89723229 | 46 | NO |
| MO_1069 | ANKRD11 | 16 | 89484691 | ZNF276 | 16 | 89793757 | 153 | NO |
| MO_1069 | MLPH | 2 | 238451302 | COL6A3 (AS) | 2 | 238259785 | 1476 | NO |
| MO_1069 | UBN2 | 7 | 138936802 | TTC26 | 7 | 138854034 | 18 | YES |
| MO_1069 | HEXDC | 17 | 80394613 | OGFOD3 (AS) | 17 | 80371025 | 7 | NO |
| MO_1069 | TBCD | 17 | 80772809 | FOXK2 | 17 | 80544938 | 24 | YES |
| MO_1069 | CALCOCO2 | 17 | 46928989 | CEP112 (AS) | 17 | 63755705 | 43 | NO |
| MO_1069 | CTNNA1 | 5 | 138119060 | KDM3B | 5 | 137733866 | 28 | NO |
| MO_1069 | ITCH | 20 | 32957275 | ASIP | 20 | 32848170 | 6 | NO |
| MO_1129 | DDB1 | 11 | 61091450 | PAK1 | 11 | 77066886 | 208 | YES |
| MO_1129 | VPS35 | 16 | 46702841 | SLCO2B1 | 11 | 74911268 | 85 | YES |
| MO_1129 | RBL2 | 16 | 53496566 | ANKRD26P1 (AS) | 16 | 46602603 | 99 | NO |
| MO_1167 | PFFKFB3 | 10 | 6268327 | LOC399715 | 10 | 6368508 | 10 | NO |
| MO_1167 | STK38L | 12 | 27450642 | PPFIBP1 | 12 | 27677297 | 4 | NO |
| MO_1167 | JMJD1C | 10 | 65140241 | REEP3 | 10 | 65281497 | 11 | NO |
| MO_1185 | SSH2 | 17 | 28120954 | EFCAB5 | 17 | 28257176 | 3 | NO |

TABLE 6

AF-4 = AF4 domain
C2A = C2 domain
CPSF-A = CPSF A subunit domain
ENSTL = Endostatin-like domain
FH = Forkhead DNA binding domain
FHA = Forkhead associated domain
GMPK = Guanylate kinase domain
GP = G-patch domain
HAD = haloacid dehydrogenase
HRD = Hpc2-related domain
IBN-N = Importin-beta N-terminal domain
Ig = Immunoglobulin domain
Kazal = Kazal type serine protease inhibitor domain TABLE 6-continued L27 = Lin2/Lin7 domain
LamG = Laminin G domain
LDL = Low Density Lipoprotein Receptor Class A domain
LY = Low-density lipoprotein-receptor YWTD domain
M20 Dipept = M20 Dipeptidase domain
MFS = Major Facilitator Superfamily domain
MMS1-N = methyl methanesulfonate N-terminal
NeuA = NeuAc synthetase
PBD = p21 binding domain
PDZ = PDZ domain
PIK3a = PIK3 accessory domain
PIK3c = PIK3 catalytic domain
PLA2 = phospholipase A2 domain TABLE 6-continued PPase = Pyrophosphatase domain
PTKc = Protein Tyrosine kinase catalytic domain
PX = phosphoinositide binding domain
RabGAP = Rab-GTPase activating domain
RHOD = Rhodanese Homology Domain
SH3 = Src homology 3 domain
SP = Signal peptide
STKc = Serine/Threonine kinase catalytic domain
TFCD = Tubulin folding cofactor D C-terminal domain
TM = Transmembrane domain
TPR = Tetratricopeptide repeat domain
TSPN = Thrombospondin N-terminal-like domain
UBN-AB = Ubinuclein conserved middle domain
Zf = Zinc finger domain
14-3-3 = 14-3-3 phosphoserine/threonine-binding domain

TABLE 7

Variants of ESR1.

| Sample Cancer | hg19 Coord | Reference | Somatic Variant | Reference Transcript | Coding Sequence Change | Reference Protein | Amino Acid Change |
|---|---|---|---|---|---|---|---|
| Carcinoma, Invasive Ductal | 152419923 | A | C | NM_000125.3 | c.1844A > C | NP_000116.2 | p.Y537S |
| Adenocarcinoma | 152419926 | A | G | NM_000125.3 | c.1847A > G | NP_000116.2 | p.D538G |
| Adenocarcinoma | 152419920 | T | A | NM_000125.3 | c.1841T > A | NP_000116.2 | p.L536H |
| Adenocarcinoma | 152419923 | A | C | NM_000125.3 | c.1844A > C | NP_000116.2 | p.Y537S |
| Carcinoma | 152419926 | A | G | NM_000125.3 | c.1847A > G | NP_000116.2 | p.D538G |
| Carcinoma | 152419923 | A | C | NM_000125.3 | c.1844A > C | NP_000116.2 | p.Y537S |
| Carcinoma, Invasive Ductal | 152419926 | A | G | NM_000125.3 | c.1847A > G | NP_000116.2 | p.D538G |

All publications, patents, patent applications and accession numbers mentioned in the above specification are herein incorporated by reference in their entirety. Although the invention has been described in connection with specific embodiments, it should be understood that the invention as claimed should not be unduly limited to such specific embodiments. Indeed, various modifications and variations of the described compositions and methods of the invention will be apparent to those of ordinary skill in the art and are intended to be within the scope of the following claims.

We claim:

1. A method of detecting the presence of a variant estrogen receptor (ESR1) gene, comprising:
   a) i) assaying a sample for the presence of a p.Leu536Gln variation in the ESR1 gene, ii) and further assaying said sample for p.Tyr537Ser and/or p.Tyr537Asn variations, wherein said assaying comprises the use of nucleic acid molecules that detect the presence of said variations; and
   b) identifying the presence of a p.Leu536Gln variation in said sample.

2. The method of claim 1, wherein said nucleic acid molecules comprise a nucleic acid primer.

3. The method of claim 2, wherein said detecting comprises forming a complex between said ESR1 gene and said nucleic acid primer.

4. The method of claim 1, wherein the sample is breast tissue.

5. The method of claim 1, wherein said sample is from a subject diagnosed with cancer.

6. The method of claim 5, wherein said cancer is breast cancer or endometrial cancer.

7. The method of claim 1, further comprising assaying said sample for the presence of p.Tyr537Cys.

* * * * *